US007196054B1

United States Patent
Drohan et al.

(10) Patent No.: US 7,196,054 B1
(45) Date of Patent: Mar. 27, 2007

(54) METHODS FOR TREATING WOUND TISSUE AND FORMING A SUPPLEMENTED FIBRIN MATRIX

(75) Inventors: William N. Drohan, Springfield, VA (US); Martin J. MacPhee, Darnestown, MD (US); Hernan Nunez, Derwood, MD (US); Gene Liau, Wayland, MA (US); Thomas Maciag, Portland, ME (US); Wilson H. Burgess, Clifton, VA (US)

(73) Assignee: The American National Red Cross, Rockville, MD (US)

( * ) Notice: Subject to any disclaimer, the term of this patent is extended or adjusted under 35 U.S.C. 154(b) by 0 days.

(21) Appl. No.: 08/485,883

(22) Filed: Jun. 7, 1995

Related U.S. Application Data

(63) Continuation-in-part of application No. 08/351,006, filed on Dec. 7, 1994, now abandoned, which is a continuation-in-part of application No. 08/328,552, filed on Oct. 25, 1994, now abandoned, which is a continuation of application No. 08/031,164, filed on Mar. 12, 1993, now abandoned, which is a continuation-in-part of application No. 07/618,419, filed on Nov. 27, 1990, now abandoned, and a continuation-in-part of application No. 07/798,919, filed on Nov. 27, 1991, now abandoned.

(51) Int. Cl.
    *A61K 38/36* (2006.01)
(52) U.S. Cl. .............................. 514/2; 514/21
(58) Field of Classification Search .............. 530/382, 530/381; 435/214; 424/94.04, 529; 514/2
    See application file for complete search history.

(56) References Cited

U.S. PATENT DOCUMENTS

| | | | |
|---|---|---|---|
| 2,533,004 A | 12/1950 | Ferry et al. .................. 260/112 |
| 3,523,807 A | 8/1970 | Gerendas ..................... 106/124 |
| 3,723,244 A | 3/1973 | Breillatt, Jr. ................. 162/151 |
| 4,265,233 A | 5/1981 | Sugitachi et al. ........... 128/156 |
| 4,298,598 A | 11/1981 | Schwarz et al. ............. 424/101 |
| 4,321,711 A | 3/1982 | Mano ............................... 3/1.4 |
| 4,359,049 A | 11/1982 | Redl et al. ............. 128/218 PA |
| 4,362,567 A | 12/1982 | Schwarz et al. ............. 106/157 |
| 4,373,519 A | 2/1983 | Errede et al. ................ 128/156 |
| 4,377,572 A | 3/1983 | Schwarz et al. ............. 424/101 |
| 4,394,370 A | 7/1983 | Jefferies ........................ 424/15 |
| 4,407,787 A | 10/1983 | Stemberger ................... 424/28 |
| 4,414,976 A | 11/1983 | Schwarz et al. ........ 128/334 R |
| 4,427,650 A | 1/1984 | Stroetmann ................... 424/46 |
| 4,427,651 A | 1/1984 | Stroetmann ................... 424/46 |
| 4,442,655 A | 4/1984 | Stroetmann ................... 53/428 |
| 4,453,939 A | 6/1984 | Zimmerman et al. ....... 604/368 |
| 4,472,840 A | 9/1984 | Jefferies ......................... 3/1.9 |
| 4,516,276 A | 5/1985 | Mittelmeier et al. .......... 3/1.91 |
| 4,600,574 A | 7/1986 | Lindner et al. ............... 424/28 |
| 4,606,337 A | 8/1986 | Zimmermann et al. ..... 128/156 |
| 4,617,293 A | 10/1986 | Wahlig et al. ................. 514/41 |
| 4,619,913 A | 10/1986 | Luck et al. |
| 4,619,989 A | 10/1986 | Urist ........................... 530/417 |
| 4,627,879 A | 12/1986 | Rose et al. .................. 106/124 |
| 4,631,055 A | 12/1986 | Redl et al. ..................... 604/82 |
| 4,642,120 A | 2/1987 | Nevo et al. .................... 623/16 |
| 4,714,457 A | 12/1987 | Alterbaum .................... 494/37 |
| 4,717,717 A | 1/1988 | Finkenaur .................... 514/21 |
| 4,761,471 A | 8/1988 | Urist ........................... 530/350 |
| 4,789,732 A | 12/1988 | Urist ........................... 530/350 |
| 4,791,068 A * | 12/1988 | Loskutoff et al. ............ 435/7.8 |
| 4,816,339 A | 3/1989 | Tu et al. ...................... 428/421 |
| 4,820,626 A | 4/1989 | Williams et al. ............... 435/1 |
| 4,837,379 A | 6/1989 | Weinberg ................... 424/101 |
| 4,861,757 A | 8/1989 | Antoniades et al. .......... 514/21 |
| 4,874,746 A | 10/1989 | Antoniades et al. .......... 514/21 |
| 4,904,259 A | 2/1990 | Itay ............................. 623/16 |
| 4,909,251 A * | 3/1990 | Seelich ........................ 606/213 |
| 4,928,603 A | 5/1990 | Rose et al. .................. 106/124 |
| 4,952,403 A | 8/1990 | Vallee et al. ................. 424/422 |
| RE33,375 E | 10/1990 | Luck et al. ..................... 514/2 |
| 4,969,880 A | 11/1990 | Zamierowski .............. 604/305 |
| 4,983,581 A | 1/1991 | Antoniades et al. .......... 514/12 |
| 5,019,559 A | 5/1991 | Antoniades et al. .......... 514/21 |

(Continued)

FOREIGN PATENT DOCUMENTS

| | | |
|---|---|---|
| AU | B-83581/82 | 11/1982 |
| AU | B-43122/85 | 12/1985 |
| AU | 554041 | 8/1986 |

(Continued)

OTHER PUBLICATIONS

Lasa, C.I. et al., Journal of Surgical Research, vol. 54(3), pp. 202-206, Mar. 1993.*
Spinuzza Harris, E. et al., Surgical Forum, vol. 43(0), pp. 515-516, 1992.*
Cadoni et al. Endoscopy 22 (1990) p. 194-195, Jan. 1990.*
Epstein, G.H. et al., "A New Autologous Fibrinogen-Based Adhesive For Otologic Surgery," *Ann. Otol. Rhinol. Laryngol.* 95:40-45 (1986).

(Continued)

*Primary Examiner*—Jean C. Witz
(74) *Attorney, Agent, or Firm*—Sterne, Kessler, Goldstein & Fox P.L.L.C.

(57) ABSTRACT

This invention provides supplemented and unsupplemented tissue sealants as well as methods for their production and use thereof. Disclosed are tissue sealants supplemented with at least one antimicrobial composition. The composition may be further supplemented with, for example, one or more antibodies, analgesics, anticoagulants, antiproliferatives, anti-inflammatory compounds, cytokines, cytotoxins, drugs, growth factors, interferons, hormones, lipids, demineralized bone or bone morphogenetic proteins, cartilage inducing factors, oligonucleotides polymers, polysaccharides, polypeptides, protease inhibitors, vasoconstrictors or vasodilators, vitamins, minerals, stabilizers and the like.

39 Claims, 36 Drawing Sheets

U.S. PATENT DOCUMENTS

| | | | |
|---|---|---|---|
| 5,023,082 A | 6/1991 | Friedman et al. | 424/426 |
| 5,030,215 A | 7/1991 | Morse et al. | 604/410 |
| 5,034,375 A | 7/1991 | Antoniades et al. | 514/12 |
| 5,035,887 A | 7/1991 | Antoniades et al. | 424/85.2 |
| 5,059,123 A | 10/1991 | Jernberg | 433/215 |
| 5,124,155 A | 6/1992 | Reich | 424/428 |
| 5,139,527 A | 8/1992 | Redl et al. | 623/66 |
| 5,171,318 A | 12/1992 | Gibson et al. | 623/5 |
| 5,171,579 A | 12/1992 | Ron et al. | 424/486 |
| 5,219,328 A | 6/1993 | Morse et al. | 604/49 |
| 5,226,877 A | 7/1993 | Epstein | 604/35 |
| 5,260,420 A | 11/1993 | Burnouf-Radosevich et al. | 530/382 |
| 5,290,552 A * | 3/1994 | Sierra et al. | 424/94.64 |
| 5,368,858 A | 11/1994 | Hunziker | 424/423 |
| 5,407,671 A | 4/1995 | Heimburger et al. | 424/94.1 |
| 5,411,894 A * | 5/1995 | Cotter et al. | 436/174 |
| 5,420,250 A * | 5/1995 | Lontz | 530/381 |
| 5,549,904 A * | 8/1996 | Juergensen et al. | 424/423 |
| 5,607,694 A * | 3/1997 | Marx | 424/450 |
| 5,962,420 A * | 10/1999 | Edwardson et al. | 514/21 |
| 6,197,325 B1 * | 3/2001 | MacPhee et al. | 424/400 |

FOREIGN PATENT DOCUMENTS

| | | |
|---|---|---|
| AU | B-75097/87 | 1/1988 |
| AU | 576365 | 8/1988 |
| AU | B-91093/91 | 6/1992 |
| CA | 1119516 | 9/1982 |
| CA | 1 168 982 | 12/1984 |
| DE | 3037270 | 5/1982 |
| DE | 231 987 | 1/1986 |
| EP | 0 081 990 | 6/1983 |
| EP | 0 312 208 | 9/1988 |
| EP | 0 341 007 A2 | 11/1989 |
| EP | 0 443 724 | 8/1991 |
| EP | 0 485 210 A2 | 5/1992 |
| EP | 0 562 864 | 9/1993 |
| GB | 1 584 080 | 12/1977 |
| GB | 2 041 942 | 2/1979 |
| GB | 2 042 556 | 2/1979 |
| GB | 2 102 811 | 2/1983 |
| GB | 2 102 811 A | 2/1983 |
| GB | 2 137 209 | 10/1984 |
| GB | 2 102 811 | 1/1985 |
| GB | 2 185 747 | 7/1987 |
| JP | 55-110556 | 8/1980 |
| JP | 57-153645 | 9/1982 |
| JP | 58-026821 | 2/1983 |
| JP | 58-38216 | 3/1983 |
| JP | 58-38217 | 3/1983 |
| JP | 59-192364 | 10/1984 |
| JP | 60-204725 | 10/1985 |
| JP | 61-171429 | 8/1986 |
| JP | 62-246370 | 10/1987 |
| JP | 63-24951 | 2/1988 |
| JP | 63-115564 | 5/1988 |
| JP | 64-86974 | 3/1989 |
| JP | 1-99565 | 4/1989 |
| JP | 2-114 | 1/1990 |
| JP | 2-71750 | 3/1990 |
| JP | 2-167234 | 6/1990 |
| JP | 55-110557 | 8/1990 |
| JP | 5-970 | 1/1993 |
| WO | 81/00516 | 3/1981 |
| WO | 86/00526 | 1/1986 |
| WO | 86/03122 | 6/1986 |
| WO | WO 88/03409 | 5/1988 |
| WO | WO 89/05656 | 6/1989 |
| WO | WO 89/11293 | 11/1989 |
| WO | WO 90/01331 | 2/1990 |
| WO | WO 91/00046 | 1/1991 |
| WO | WO 91/00046 A2 | 1/1991 |
| WO | WO 91/00046 A3 | 1/1991 |
| WO | 91/09573 | 7/1991 |
| WO | 91/17744 | 11/1991 |
| WO | 92/09697 | 6/1992 |
| WO | WO 92/09301 | 6/1992 |
| WO | WO 92/13547 | 8/1992 |
| WO | WO 92/13565 | 8/1992 |
| WO | 92/22312 | * 12/1992 |
| WO | WO 93/05067 | 3/1993 |
| WO | WO 94/20133 | 9/1994 |
| WO | WO 96/17633 | 6/1996 |

OTHER PUBLICATIONS

Gersdorff, M.C.H. et al., "A New Procedure For Bone Reconstruction In Oto-Microsurgery: A Mixture Of Bone Dust And Fibrinogen Adhesive," *Laryngosc.* 95:1278-1280 (1985).

Härting, F. et al., "Glued Fixation of Split-Skin Graft to the Bony Orbit Following Exenteration," *Plas. Reconstruc. Surg.* 76(4):633-635 (1985).

Ikossi-O'Connor, M.G. et al., "The Role of Fibrin Adhesive in Vascular Surgery," *J. Surg. Oncol.* 23:151-152 (1983).

Petrelli, N.J. et al., "The Application of Tissue Adhesives in Small Bowel Anastomoses," *J. Surg. Oncol.* 19:59-61 (1982).

Thompson, D.F. et al., "Fibrin Glue: A Review Of Its Preparation, Efficacy, And Adverse Effects As A Topical Hemostat," *Dr. Intell. Clin. Pharm.* 22:946-952 (1988).

Throson, G.K. et al., "The Role of the Tissue Adhesive Fibrin Seal (FS) in Esophageal Anastomoses," *J. Surg. Oncol.* 24:221-223 (1983).

Adelmann-Grill et al., "Chemotactic Migration of Normal Dermal Fibroblasts Towards Epidermal Growth Factor and Its Modulation by Platelet-Derived Growth Factor and Transforming Growth Factor-Beta," *European J. Cell. Biol.* 51:322-326 (Apr. 1990).

Akrami et al., "Replacement of the Thoracic Aorta by Sealed Dacron Prostheses," *Thoraxchirurgie* 26:144-147 (1978).

Albrektsson et al., "Fibrin Adhesive System (FAS) Influence on Bone Healing Rate," *Acta Orthop. Scand.* 53:757-763 (1982).

Allen et al., "Influence of Endothelial Cell Seeding on Platelet Deposition and Patency in Small-Diameter Dacron Arterial Grafts," *J. Vasc. Surg.* 1:224-233 (1984).

Arbes et al., "First Clinical Experience with Heterologous Cancellous Bone Grafting Combined with the Fibrin Adhesive System (F.A.S.)," *Arch. Orthop. Traumat. Surg.* 98:183-188 (1981).

Baird et al., "Fibroblast Growth Factors," *British Medical Bulletin* 45(2): 438-452 (1989).

Berger et al., "Healing of Arterial Prostheses in Man: Its Incompleteness," *Ann. Surg.* 175(1):118-127 (1972).

Borst et al., "Fibrin Adhesive: An Important Hemostatic Adjunct in Cardiovascular Operations," *J. Thorac. Cardiovasc. Surg.* 84:548-553 (1982).

Bösch, V.P., "Autologous Cancellous Bone Grafting in Rabbits Using a Fibrinogen Adhesive System," *Wiener klinische Wochenschrift* 91(18) :628-633 (1979).

Bösch, V.P., "Bone Grafting with Fibrin Glue," *Wein Klin. Wochenschr.* 93 (Suppl. 124):3-26 (1981).

Bösch, V.P., "Experimental Investigations of the Effect of the Fibrin Adhesive on the Kiel Heterologous Bone Graft," *Arch. Orthop. Traumat. Surg.* 96:177-185 (1980).

Bösch et al., "The Technic of Fibrin Glue in Cancellous Bone Transplants," *Arch. Orthop. Unfall-Chir.* 90:63-75 (1977).

Burgess et al., "The Heparin-Binding (Fibroblast) Growth Factor Family of Proteins," *Annual Rev. Biochem.* 58:575-606 (1989).

Byrne et al., "Effect of Fibrin Glues on the Mechanical Properties of Healing Wounds," *Br. J. Surg.* 78:841-843 (Jul. 1991).

Carter et al., "Clinical Experience with Crude Preparations of Growth Factors in Healing of Chronic Wounds in Human Subjects," in: Growth Factors and Other Aspects of Wound Healing: Biological and Clinical Implications, pp. 303-317 (1988).

Clowes et al., "Graft Endothelialization: The Role of Angiogenic Mechanisms," *J. Vascular Surgery* 13(5):734-736 (May 1991).

Clowes et al., "Mechanisms of Arterial Graft Healing," *Am. J. Pathol.* 123(2):220-230 (1986).

Conant et al., "Treatment of Condylomata Acuminata with Intralesional 5-Fluorouracil Therapeutic Implant (MPI 5003)," *Clinical Res.* 39(4):818A (Dec. 1991).

Cziperle et al., "Enhanced Endothelialization of Expanded Polytetrafluoroethylene Grafts by Heparin Binding Growth Factor-Type I (HBGF-1) Pretreatment," *Presented at the Society of University Surgeons* (Feb. 1992).

Davidson et al., "Mechanisms of Accelerated Wound Repair Using Epidermal Growth Factor and Basic Fibroblast Growth Factor," in: Growth Factors and Other Aspects of Wound Healing: Biological and Clinical Implications, Alan R. Liss, Inc., pp. 63-75 (1988).

Deyerling et al., "A Suspension of Fibrin Glue and Antibiotic for Local Treatment of Myocotic Aneurysms in Endocarditis—An Experimental Study," *Thorac. Cardiovasc. Surgeon* 32:369-372 (1984).

Dresdale et al., "Hemostatic Effectiveness of Fibrin Glue Derived from Single-Donor Fresh Frozen Plasma," *Annals of Thoracic Surgery* 40(4):385-387 (1985).

Dresdale et al., "Preparation of Fibrin Glue from Single-Donor Fresh-Frozen Plasma," *Surgery* 97(6):750-755 (1985).

Durham et al., "A Method for Preparation of Fibrin Glue," *J. Laryngology and Otology* 101:1182-1186 (1987).

Dvorak et al., "Fibrin Containing Gels Induce Angiogenesis," *Lab. Invest.* 57(6):673-686 (1987).

Foxall et al., "Adult Human Endothelial Cell Coverage of Small-Caliber Dacron and Polytetrafluoroethylene Vascular Prosthesis in Vitro," *J. Surg. Res.* 41:158-172 (1986).

Froesch et al., "Actions of Insulin-Like Growth Factors," *Ann. Rev. Physiol.* 47:443-467 (1985).

Gibble et al., "Fibrin Glue: The Perfect Operative Sealant," *Transfusion* 30(8):741-747 (Aug. 1990).

Gospodarowicz et al., "Structural Characterization and Biological Functions of Fibroblast Growth Factor," *Endocrine Reviews* 8(2):95-114 (1987).

Goudarzi, Y.M. "Clinical Experiences with a Fibrin-Nebacetin Bone Marrow Combination in the Treatment of Chronic Bone Infections and as Local Infection Prophylaxis in Non-Infected Bone Diseases," *Akt. Traumatol.* 13:205-209 (1983).

Graham et al., "Expanded Polytetrafluoroethylene Vascular Prostheses Seeded with Enzymatically Derived and Cultured Canine Endothelial Cells," *Surgery* 91(5):550-559 (1982).

Greco et al., "Fibrin-Antibiotic Mixtures: An *in Vitro* Study Assessing the Possibility of Using a Biologic Carrier for Local Drug Delivery," *J. Biomedical Materials Res.* 25:39-51 (Jan. 1991).

Greenhalgh et al., "PDGF and FGF Stimulate Wound Healing in the Genetically Diabetic Mouse," *Am. J. Path.* 136(6):1235-1246 (Jun. 1990).

Greisler et al., "Biomaterial Pretreatment with ECGF to Augment Endothelial Cell Proliferation," *J. Vasc. Surg.* 5(2):393-399 and 402 (1987).

Greisler et al., "Endothelial Cell Growth Factor Attachment to Biomaterials," *Trans. Am. Soc. Artif. Intern. Organs. XXXII*:346-349 (1986).

Greisler et al., "Enhanced Endothelialization of Expanded Polytetrafluoroethylene Grafts by Fibroblast Growth Factor Type 1 Pretreatment," *Surgery* 112(2):244-255 (Aug. 1992).

Greisler et al., "Enhancement of Polytetrafluoroethylene Endothelialization by Pretreatment with Fibrin Glue Containing Heparin Binding Growth Factor-Type I (HBGF-1)," *Proc. Cardiovascular Science and Technology Conf.,* p. 50 (Dec. 2-4, 1991).

Gundry et al., "A Quantitative and Qualitative Comparison of Fibrin Glue, Albumin, and Blood as Agents to Pretreat Porous Vascular Grafts," *J. of Surgical Res.* 43:75-77 (1987).

Harker et al., "Platelet Consumption by Arterial Prostheses: The Effects of Endothelialization and Pharmacologic Inhibition of Platelet Function," *Ann. Surg.* 186(5):594-601 (1977).

Harrison et al., "Osteogenin Promotes Reexpression of Cartilage Phenotype by Dedifferentiated Articular Chondrocytes in Serum-Free Medium," *Exp. Cell Res.* 192:340-345 (Fall, 1991).

Hattori, T., "Experimental Investigations of Osteogenesis and Chondrogenesis by Implant of BMP-Fibrin Glue Mixture," *J. Jpn. Orthop. Assoc.* 64:824-834 (after Jun. 1990).

Haverich et al., "Histopathological Evaluation of Woven and Knitted Dacron Grafts for Right Ventricular Conduits: A Comparative Experimental Study," *Annals of Thoracic Surgery* 37(5):404-411 (1984).

Haverich et al., "Pericardial Flap-Plasty for Protection of the Tracheal Anastomosis in Heart-Lung Transplantation," *J. Cardiac Surgery* 4(2):136-139 (1989).

Haverich et al., "Prevention of Graft Infection by Bonding of Gentamycin to Dacron Prostheses," *J. Vasc. Surg.* 15(1):187-193 (Jan. 1992).

Haverich et al., "The Use of Fibrin Glue for Sealing Vascular Prostheses of High Porosity," *Thorac. Cardiovasc. Surgeon* 29:252-254 (1981).

Hayek et al., "An *in Vivo* Model for Study of the Angiogenic Effects of Basic Fibroblast Growth Factor," *Biochem. Biophys. Res. Commun.* 147(2):876-880 (1987).

Herring et al., "Endothelial Seeding of Polytetrafluoroethylene Popliteal Bypasses," *J. Vasc. Surg.* 6:114-118 (1987).

Jarrell et al., "Human Adult Endothelial Cell Growth in Culture," *J. Vasc. Surg.* 1:757-764 (1984).

Jonas et al., "Biological Sealants and Knitted Dacron Conduits: Comparison of Collagen and Fibrin Glue Pretreatments in Circulatory Models," *Annals of Thoracic Surgery* 44:283-290 (1987).

Jonas et al., "Biological Sealants and Knitted Dacron: Porosity and Histological Comparisons of Vascular Graft Materials With and Without Collagen and Fibrin Glue Pretreatments," *Annals of Thoracic Surgery* 41:657-663 (1986).

Karck et al., "Pretreatment of Prosthetic Valve Sewing-Ring with the Antibiotic/Fibrin Sealant Compound as a Prophylactic Tool Against Prosthetic Valve Endocarditis," *Eur. J. Cardio-Thorac. Surg.* 4:142-146 (Mar. 1990).

Kawamura et al., "Human Fibrin is a Physiologic Delivery System for Bone Morphogenetic Protein," *Clinical Orthopaedics and Related Res.* 235:302-310 (1988).

Kempczinski et al., "Endothelial Cell Seeding of a New PTFE Vascular Prosthesis," *J. Vasc. Surg.* 2:424-429 (1985).

Kesler et al., "Enhanced Strength of Endothelial Attachment on Polyester Elastomer and Polytetrafluoroethylene Graft Surfaces with Fibronectin Substrate," *J. Vasc. Surg.* 3:58-64 (1986).

Knighton et al., "Classification and Treatment of Chronic Nonhealing Wounds," *Ann. Surg.* 204(3):332-330 (1986).

Knighton et al., "Regulation of Cutaneous Wound Healing by Growth Factors," *Clinical Materials* 8:229-242 (1991 received in the National Library of Medicine in Feb. 1992).

Knighton et al., "The Use of Platelet Derived Wound Healing Formula in Human Clinical Trials," in: Growth Factors and Other Aspects of Wound Healing: Biological and Clinical Implications, pp. 319-329 (1988).

Kovács et al., "Biolplast® Fibrin Coagulum in Large Cystic Defects of the Jaw," *Intl. J. Oral Surg.* 5:111-116 (1976).

Köveker, G., "Clinical Application of Fibrin Glue in Cardiovascular Surgery," *Thorac. Cardiovasc. Surgeon* 30:228-229 (1982).

Köveker et al., "Clinical Experience with Fibrin Glue in Cardiac Surgery," *Thorac. Cardiovasc. Surgeon* 29:287-289 (1981).

Köveker et al., "Reduction of Thrombogenicity in Small-Diameter Vascular Prostheses Seeded with Autologous Endothelial Cells," *Thorac. Cardiovasc. Surgeon* 34:49-51 (1986).

Kram et al., "Antibacterial Effects of Fibrin Glue-Antibiotic Mixtures," *J. Surgical Res.* 50:175-178 (1991—presented Apr. 28-May 2, 1989).

Kram et al., "Fibrin Glue Sealing of Polytetrafluoroethylene Vascular Graft Anastomoses: Comparison with Oxidized Cellulose," *J. Vasc. Surg.* 8(5):563-568 (1988).

Kratzat et al., "Clinical Experiences with the Fibrin-Antibiotic Combination in Infections of the Bones and Soft Parts," *Akt. Chir.* 17:58-62 (1982).

Kratzat et al., "Erste Klinische Enfahrungen mit dem Fibrin-Antibiotikum-Verbund beider osteomyelitis," *Orthop. Praxis* 17:852-855 (1981).

Kratzat et al., "Klinische Erfahrungen mit dem Fibrin-Antibiotikum-Verbund bei Knochen-und Weichteilinfektionen," in: Fibrinkleber in Orthopadie und Traumatologie Cotta et al., eds., Thieme Verlag, Stuttgart, pp. 200-204 (1982).

Kreider et al., "Concordance of Condylomata Acuminata Responses to Treatment with Intralesional MPI 5003 and Papailoma Responses in the Shope Rabbit Papilloma Model System," *Skin Pharmacol.* 5(4):201-202 (Oct. 1992).

Ksander et al., "The Effect of Platelet Releasate on Wound Healing in Animal Models," *J. Am. Acad. Dermatol.* 22(No. 5, Part I): 781-791 (May 1990).

Lasa et al., "Osteoregeneration Using a Fibrin Sealant Delivery Vehicle for Demineralized Bone Matrix," *J. Cell. Biochem. Suppl. O*(17 Part E):162 Abstract No. RZ 217 (Mar. 29-Apr. 25, 1993).

Lerner et al., "Current Status of Surgical Adhesives," *J. Surg. Res.* 48:165-181 (Feb. 1990).

Lindner et al., "Basic Fibroblast Growth Factor Stimulates Endothelial Regrowth and Proliferation in Denuded Arteries," *J. Clin. Invest.* 85:2004-2008 (Jun. 1990).

Lobb, R.R., "Clinical Applications of Heparin-Binding Growth Factors," *Eur. J. Clin. Invest.* 18:321-336 (1988).

Lucht et al., "Fibrin Sealant in Bone Transplantation," *Acta. Orthop. Scand.* 57:19-24 (1986).

Luyten et al., "Purification and Partial Amino Acid Sequence of Osteogenin, a Protein Initiating Bone Differentiation," *J. Biol. Chem.* 264(23): 13377-13380 (1989).

Lynch et al., "Growth Factors in Wound Healing," *J. Clin. Invest.* 84:640-646 (1989).

Mark et al., "Repair of Calvarial Nonunions by Osteogenin, A Bone-Inductive Protein," *Plastic and Reconstructive Surgery,* 86(4):623-630 (Oct. 1990).

Massagué, J., "The TGF-β Family of Growth and Differentiation Factors," *Cell* 49:437-438 (1987).

Matras, H., "Fibrin Seal: The State of the Art," *J. Oral Maxillofac. Surg.* 43:605-611 (1985).

McGee et al., "Recombinant Basic Fibroblast Growth Factor Accelerates Wound Healing," *J. Surg. Res.* 45:145-153 (1988).

Miller et al., "Basal Cell Carcinomas Histologically Resolved After Treatment with Intralesional 5-Fluorouracil Therapeutic Implant," *Proc. of the Amer. Assoc. for Cancer Res.* 32:420 Abstract No. 2496 (Mar. 1991).

Montesano et al., "Basic Fibroblast Growth Factor Induces Angiogenesis *In Vitro,*" *PNAS USA* 83:7297-7301 (1986).

Moore et al., "Development of an Infection-Resistant Vascular Prosthesis," *Arch. Surg.* 116:1403-1407 (1981).

Mustoe et al., "Accelerated Healing of Incisional Wounds in Rats Induced by Transforming Growh Factor-β," *Science* 237:1333-1336 (1987).

Orenberg et al., "The Effect of Intralesional 5-Fluorouracil Therapeutic Implant (MPI 5003) for Treatment of Basal Cell Carcinoma," *J. Am. Acad. Dermatol.* 27:723-728 (Nov. 1992).

Yu and Palecek et al., "Pharmacokinetics and Clinical Application of the Intralesional Methotrexate Therapeutic Implant," *Proc. Annu. Meet. Am. Soc. Clin. Oncol.* 11:100 Abstract No. 222 (Mar. 1992).

Pierce et al., "*In Vivo* Incisional Wound Healing Augmented by Platelet-Derived Growth Factor and Recombinant *c-sis* Gene Homodimeric Proteins," *J. Exp. Med.* 167:974-987 (1988).

Pop et al., "Experimental Covering of the Dental Pulp in the Dog with Biological Substances," *Chemical Abstracts* 72:209 Abstract No. 119944n (1970).

Presta et al., "Basic Fibroblast Growth Factor Requires a Long-Lasting Activation of Protein Kinase C to Induce Cell Proliferation in Transformed Fetal Bovine Aortic Endothelial Cells," *Cell Regulation* 2:719-726 (Sep. 1991).

Puumala et al., "Intraventricular Infusion of HBGF-2 Promotes Cerebral Angiogenesis in Wistar Rat," *Brain Res.* 534:283-286 (Nov. 1990).

Radomski et al., "Initial Adherence of Human Capillary Endothelial Cells to Dacron," *J. Surgical Res.* 42:133-140 (1987).

Ramalanjaona et al., "The Effect of Fibronectin Coating on Endothelial Cell Kinetics in Polytetrafluoroethylene Grafts," *J. Vasc. Surg.* 3:264-272 (1986).

Redl et al., "Fibrinkleber-Antibiotika-Gemische—Festigkeit und Elutionsverhalten," in: Fibrinkleber in Orthopadie und Traumatologie, Cotta et al., eds., Thieme Verlag, Stuttgart, pp. 178-181 (1982).

Redl et al., "*In Vitro* Properties of Mixtures of Fibrin Seal and Antibiotics," *Biomaterials* 4:29-32 (1983).

Roberts et al., "Transforming Growth Factor β," *Advances in Cancer Res.* 51:107-141 (1988).

Rothe et al., "Growth Factors: Their Biology and Promise in Dermatologic Diseases and Tissue Repair," *Arch. Dermatol.* 125:1390-1398 (1989).

Rovee, D.T., "Evolution of Wound Dressings and Their Effects on the Healing Process," in: Clinical Materials, Elsevier Science Publishers Ltd., England, pp. 183-188 (1991).

Sakurai et al., "Controlled Release of Sisomicin from Fibrin Glue," *J. Controlled Release* 18:39-44 (Jan. 1992).

Sauvage et al., "Interspecies Healing of Porous Arterial Prostheses," *Arch. Surg.* 109:698-705 (1974).

Schlag et al., "Fibrin Sealant in Orthopedic Surgery," *Clinical Orthopaedics and Related Res.* 227:269-285 (1988).

Schrenk et al., "Fibrin Glue Coating of e-PTFE Prostheses Enhances Seeding of Human Endothelial Cells," *Thorac. Cardiovasc. Surgeon* 35:6-10 (1987).

Schultz et al., "Epithelial Wound Healing Enhanced by Transforming Growth Factor-α and Vaccinia Growth Factor," *Science* 235:350-352 (1987).

Schwarz et al., "The Influence of Fibrin Sealant on Demineralized Bone Matrix-Dependent Osteoinduction," *Clinical Orthopaedics and Related Res.* 238:282-287 (1989).

Shindo et al., "Improved Patency of Collagen-Impregnated Grafts After *In Vitro* Autogenous Endothelial Cell Seeding," *J. Vasc. Surg.* 6:325-332 (1987).

Shoemaker et al., "Effects of Fibrin Sealant on Incorporation of Autograft and Xenograft Tendons Within Bone Tunnels," *Am. J. Sports Med.* 17(3):318-324 (1989).

Silbermann, M., "*In Vitro* Systems for Inducers of Cartilage and Bone Development," *Biomaterials* 11:47-49 (Jul. 1990).

Silberstein et al., "An Autologous Fibrinogen-Based Adhesive for Use in Otologic Surgery," *Transfusion* 28 (4):319-321 (1988).

Spotnitz et al.. "Fibrin Glue from Stored Human Plasma," *The American Surgeon* 53(8):460-462 (1987).

Sprugel et al., "The Effects of Different Growth Factors in Subcutaneous Wound Chambers," in: Growth Factors and Other Aspects of Wound Healing: Biological and Clinical Implications, pp. 77-91 (1988).

Stark et al., "Experience with Fibrin Seal (Tisseel) in Operations for Congenital Heart Defects," *Annals of Thoracic Surgery* 38 (4):411-413 (1984).

Sugie et al., "The Chemical Modification of Fibrin Film as Artificial Skin," *Chemical Abstracts* 85:318 Abstract No. 182381k (1976).

Thompson et al., "Heparin-Binding Growth Factor 1 Induces the Formation of Organoid Neovascular Structures *In Vivo,*" *PNAS USA* 86:7928-7932 (1989).

Thompson et al., "Site-Directed Neovessel Formation *In Vivo,*" *Science* 241:1349-1352 (1988).

Tsuboi et al., "Recombinant Basic Fibroblast Growth Factor Stimulates Wound Healing in Healing-Impaired db/db Mice," *J. Exp. Med.* 172:245-251 (Jul. 1990).

Ulatowski et al., "A Biological Adhesive System and Antibiotics for the Enhancement of Wound Healing," *Fortschr. Med.* 99:864-868 (1981).

Ulatowski et al., "Neue Aspekte der Anwendung eines erweiterten Fibrinklebesystems (FKS)," *Orthop. Praxis* 15:795-799 (1979).

Ulatowski et al., "Pharmacokinetik eines Fibrinantibiotikumverbundes," in: Fibrinkleber in Orthopadie und Traumatologie, Cotta et al., eds., Thieme Verlag, Stuttgart, pp. 196-199 (1982).

Urist et al., "Bone Formation in Implants of Partially and Wholly Demineralized Bone Matrix," *Clinical Orthopaedics and Related Res.* 71:271-278 (1970).

Urist et al., "Bone Morphogenesis in Implants of Insoluble Bone Gelatin," *PNAS USA* 70(12 Part I):3511-3515 (1973).

Walterbusch et al., "Clinical Experience with Fibrin Glue for Local Bleeding Control and Sealing of Vascular Prostheses," *Thorac. Cardiovasc. Surgeon* 30:234-235 (1982).

Wang et al., "Bone Morphogenetic Proteins and Bone Repair," *J. Cell. Biochem. Suppl.* 0(15 Part F):161 (Jan. 1991).

Watkins et al., "Adult Human Saphenous Vein Endothelial Cells: Assessment of Their Reproductive Capacity for Use in Endothelial Seeding of Vascular Prostheses," *J. Surg. Res.* 36:588-596 (1984).

Weisman et al., "Biochemical Characterization of Autologous Fibrinogen Adhesive," *Laryngoscope* 97:1186-1190 (1987).

Williams et al., "Adult Human Endothelial Cell Compatibility with Prosthetic Graft Material," *J. Surgical Res.* 38:618-629 (1985).

Yu et al., "Comparison of Antitumor Effects of Treatment Sequence of Fluorouracil (FU) and Cisplatin (Pt) Therapeutic Implants in a Mouse Tumor Model," *Proc. Annu. Meet. Am. Soc. Clin. Oncol.* 11:100 Abstract No. 223 (Mar. 1992).

Zilch et al., "Diffusionsverhalten von Cefotaxim aus der Fibrin-Antibiotika-Plombe im Tierversuch," in: Fibrinkleber in Orthopadie und Traumatologie, Cotta et al., eds., Thieme Verlag, Stuttgart, pp. 191-195 (1982).

Zilch et al., "The Sustained Release of Cefotaxim from a Fibrin-Cefotaxim Compound in Treatment of Osteitis," *Arch. Orthop. Trauma Surg.* 106:36-41 (1986).

Zilla et al., "Use of Fibrin Glue as a Substrate for *in Vitro* Endothelialization of PTFE Vascular Grafts," *Surgery* 105(4):515-522 (1989).

B.M. Alving et al. "Fibrin sealant: summary of a conference on characteristics and clinical uses," *The Journal of The American Association of Blood Banks* 35: (9) 783-790 (Sep. 1995).

Larson, M.J. et al., "Efficacy of a Fibrin Hemostatic Bandage in Controlling Hemorrhage From Experimental Arterial Injuries," *Arch. Surg.* 130:420-422 (1995).

MacPhee, M., "Fibrin Sealant Based Bandages and Foam: Hemostatic Devices for Treatment of Combat Casualties on the Battlefield," Presented at the Advanced Technology Applications to Combat Casualty Care (ATACCC) conference (May 1995).

MacPhee, M., "Field-Ready Fibrin Sealant Based Hemostatic Devices," Presented at the 29th Penner Blood Conference (May 1995).

Stemberger, A. and Blümel, G., "Fibrinogen-Fibrin Conversion and Inhibition of Fibrinolysis," *Thorac. Cardiovasc. Surgeon* 30:209-214 (1982).

Martin-Zanca, D. et al., "Molecular and Biochemical Characterization of the Human trk Proto-Oncogene," *Mol. Cell. Biol.* 9:24-33, American Society for Microbiology (1989).

English language abstract of JP2167234, Furukawa Masao et al., data supplied from the esp@cenet database—I2. (1990).

English language abstract of JP1099565, Nishimaki Hideo et al., data supplied from the esp@cenet database—I2 (1989).

Afra, D. et al., "Experimentelle Untersuchung der Resorption von Fibrinfilmen und ihre Anwendung in der neurochirurgischen Praxis", *Acta Med. Acad. Sci. Hung.* 11:1-29, Hungarian Academy of Sciences (1958).

Bagdy, D. et al., "Application of Bovine Fibrin Foam and of a Mixture of Thrombin and Fibrin Powders as Haemostatic Agents," *Acto Physiol. Acad. Sci. Hung.* 2:493-504, Magyar Tudomanyos Akademia (1951).

Bagdy, D. et al., "Experimentelle und klinische Anwendung der aus Rinderplasma hergesteliten Fibrinprodukte," *Zentralblatt für Chirurgie* 77:848-852, Vereinigung Mittelrheinischer Chirurgen (1952).

Bagdy D. et al., in *Trombin-Fibrinprodukte und Ihre Therapeutische Anwendung*, pp. 152-159, 184-187, Veb Gustav Fischer Verlag Jena (1963).

Bailey, O. T. and Ingraham, F. D., "The Use of Fibrin Foam as Hemostatic Agent in Neurosurgery: Clinical and Pathological Studies," *J. Clin. Invest.* 23:591-596, The American Society for Clinical Investigation (1944).

Bailey, O. T. and Ingraham, F. D., "Fibrin Films in Neurosurgery, with Special Reference to Their Use in the Repair of Dural Defects and in the Prevention of Meningocerebral Adhesions," *J. Clin. Invest.* 23:597-600, The American Society for Clinical Investigation (1944).

Bailey, O. T. et al., "Fibrin Film in Neurosurgery, Further Studies: The Insertion of Fibrin Film Between the Sutured Dura and The Intact Leptomeninges; The Effect of Roentgen Therapy on Tissue Reactions to Fibrin Film," *J. Neurosurg.* 4:465-471, American Association of Neurological Surgeons (1947).

Bishara, S.E. et al., "Effects of a Fibrin-Sealant Wound Dressing on the Healing of Full-Thickness Wounds of the Hard Palate: Preliminary Report," *Cleft Palate Journal* 23:144-152, Allen Press Inc. (1986).

Clark, A. M. et al., "Fixation of Skin-Grafts with Human Plasma and Thrombin," *Lancet* 1:498-500, The Lancet Ltd (1945).

Cronkite, E. P. et al., "Use of Thrombin and Fibrinogen in Skin Grafting: Preliminary Report," *JAMA* 124:976-978, The American Medical Association (1944).

Dees, J. E., "The Use of Intrapelvic Coagulum in Pyelolithotomy: Preliminary Report," *South Med. J.* 36:167-175, The Southern Medical Association (1943).

Dees, J. E. and Fox, H., "The Properties of Human Fibrinogen Coagulum: Preliminary Report," *J. Urol.* 49:503-511, The Williams & Wilkins Company (1943).

Dees, J. E., "Fibrinogen Coagulum as an Aid in the Operative Removal of Renal Calculi," *J. Clin. Invest.* 23:576-579, The American Society for Clinical Investigation (1944).

Dees, J. E., "The Use of Fibrinogen Coagulum in Pyelolithotomy," *J. Urol.* 56:271-283, The Williams & Wilkins Company (1946).

Ferry, J. D. and Morrison, P. R., "Fibrin Clots, Fibrin Films, and Fibrinogen Plastics," *J. Clin. Invest.* 23:566-572, The American Society for Clinical Investigation (1944).

Frucht-Perry, J. et al., "Fibrin-Enmeshed Tobramycin Liposomes: Single Application Topical Therapy of *Pseudomonas* Keratitis," *Cornea* 11:393-397, Raven Press, Ltd. (1992).

Gerendás, M., "Fibrin Products as Aids in Hemostasis and Wound Healing," chap. 13 in *Fibrinogen*. Laki, K., Ed., Marcel Dekker, New York, pp. 277-316 (1968).

Glynn, J. H. and Richardson, J. H., "The Antigenic Properties of Fibrin Films and Foams Prepared from Human and from Bovine Blood Plasma," *J. Immunol.* 53:143-150, The Williams & Wilkins Company (1946).

Harris, H. I, "Heterogenous Skin Grafts by Coagulum Contact Method," *Am. J. Surg.* 65:315-320, The American Journal of Surgery, Inc. (1944).

Harrison, J. H. and Trichel, B. E., "Experiences with Fibrin Coagulum in Pyelolithotomy," *J. Urol.* 62:1-12, The Williams & Wilkins Company (1949).

Hawn, C.v.Z. et al., "A Note on the use of Fibrinogen and Thrombin in the Surface Treatment of Burns," *J. Clin. Invest.* 23:580-585, The American Society for Clinical Investigation (1944).

Ho, Hsiu-O et al., "Drug Release From Glutaraldehyde-Treated Fibrin Gels," *Drug Design and Delivery* 7:65-73, Harwood Academic Publishers GmbH (1990).

Hoffman, H. A., "Coagulum Pyeloithotomy," *Am. J. Surg.* 79:598-602, Excerpta Medica, Inc. (1950).

Ingraham, F. D. and Bailey, O. T., "Clinical Use of Products of Human Plasma Fractionation: The use of Products of Fibrinogen and Thrombin in Surgery," *JAMA* 126:680-685, The American Medical Association (1944).

Ingraham, F. D. and Bailey, O. T., "The Use of Products Prepared from Human Fibrinogen and Human Thrombin in Neurosurgery: Fibrin Foams as Hemostatic Agents; Fibrin Films in Repair of Dural Defects and in Prevention of Meningocerebral Adhesions," *J. Neurosurg.* 1:23-39, American Association of Neurological Surgeons (1944).

Ingraham, F. D. et al., "Studies on Fibrin Foam as a Hemostatic Agent in Neurosurgery, with Special Reference to its Comparison with Muscle," *J. Neurosurg.* 1:171-181, American Association of Neurological Surgeons (1944).

Ingraham, F. D. et al., "The Use of Fibrin Film as Dural Substitute and in the Prevention of Meningocerebral Adhesions; Further Studies and Clinical Results," *JAMA* 128:1088-1091, The American Medical Association (1945).

István, L. et al., "Gastrointestinalis várzések csillapítása thrombin-fibrin kászítménnyel," *Orv. Hetil.* 105:219-223, Markusovszky Lajos Foundation (1964).

Kaehler, J. et al., "Precoating substrate and surface configuration determine adherence and spreading of seeded endothelial cells on polytetrafluoroethylene grafts," *J. Vasc. Surg.* 9:535-541, The Society for Vascular Surgery and International Society for Cardiovascular Surgery, North American Chapter (1989).

Knöbl, P.N. et al., "The protein C system in patients undergoing cardiopulmonary bypass," *J. Thorac. Cardiovasc. Surg.* 94:600-605, American Association for Thoracic Surgery (1987).

McEvitt, W. G., "Experiences with Fibrin Fixation Methods of Skin Grafting: A Clinical Evaluation," *J. MSMS* 44:1347-1351, Michigan State Medical Society (1945).

Michael, P. and Abbot, W., "The Use of Human Fibrinogen in Reconstructive Surgery," *JAMA* 123:279, The American Medical Association (1943).

Moore, T. D. and Sweetser, T. H., Jr., "Coagulum Pelviolithotomy; an Improved Technique," *J. Urol.* 67:579-584, The Williams & Wilkins Company (1952).

Morrison, P. R. and Singer, M., A Note on Absorption Rates of Fibrin Films in Tissue, *J. Clin. Invest.* 23:573-575, The American Society for Clinical Investigation (1944).

Senderoff, R.L. et al., "Fibrin Based Drug Delivery Systems," *J. Parenteral. Sci. Tech.* 45:2-6, Parenteral Drug Association (PDA) (1991).

Sheehan, J.E., "Plasma Fixation of Skin Grafts," *Am. J. Surg.* 65:74-78, The American Journal of Surgery, Inc. (1944).

Stoll, v.H.G., "Koagulum-Pyelolithotomie," *Zeitschrift für Urologie* 52:610-615, Veb Georg Thieme Leipzig (1959).

Sugitachi, A. et al., "A Newly Designed Anticancer Tumor Immunity Drug Delivery System," *Trans. Am. Soc. Artif. Intern. Organs* 37:M177-M178, J.B. Lippincott Co. (1991).

Tidrick, R.T. and Warner, E.D., "Fibrin Fixation of Skin Transplants," *Surg.* 15:90-95, The C.V. Mosby Company (1944).

Weiner, L. and Wald, A.H., "Fibrin Foam and Thrombin as Used in the Surgical Removal of a Large Fibromyxoma of the Mandible," *J. Am. Dent. Assoc.* 33:731-735, American Dental Association (1946).

Winter, L. et al., "Experimentelle und klinische Anwendung der aus Rinderplasma hergestellten Fibrinprodukte. III. Klinische Verwendung von hämostatischen Fibrinprodukten," *Zentralblatt für Chirurgie* 78:469-479, Vereinigung Mittelrheinischer Chirurgen (1953).

Woodhall, B., "Fibrin Foam as Hemostatic Agent in Rehabilitation Neurosurgery," *JAMA* 126:469-471, The American Medical Association (1944).

"Growth Factor-Supplemented Fibrin Glue," in *The American Red Cross Biomedical Research and Development Report*, p. 21, The American Red Cross (1989).

"Growth Factor-Supplemented Fibrin Glue," in *The American Red Cross Biomedical Research Development Report*, p. 20, The American Red Cross (1990).

English Translation of JP 62-246370, translated by Translation Services PTY Ltd, translation dated Mar. 6, 2001.

English Translation of JP 63-115564, translated by Translation Services PTY Ltd, translation dated Mar. 13, 2001.

English Translation of the first full paragraph at p. 28 of Afra, D. et al., "Experimentelle Untersuchung der Resorption von Fibrinfilmen und ihre Anwendung in der neurochirurgischen Praxis", *Acta Med. Acad. Sci. Hung.* 11:1-29, Hungarian Academy of Sciences (1958), translated by McElroy Translation Company, translation dated Aug. 24, 2001.

English Translation of the second-fifth paragraphs at p. 852 of Bagdy, D. et al., "Experimentelle und klinische Anwendung der aus Rinderplasma hergesteliten Fibrinprodukte," *Zentralblatt für Chirurgie* 77:848-852, Vereinigung Mittelrheinischer Chirurgen (1952), translated by McElroy Translation Company, translation dated Aug. 24, 2001.

English Translation of the fourth-sixth paragraphs at p. 152 and the sixth paragraph at p. 184 of Bagdy D. et al., in *Trombin-Fibrinprodukte und Ihre Therapeutische Anwendung*, pp. 152-159, 184-187, Veb Gustav Fischer Verlag Jena (1963), translated by McElroy Translation Company, translation dated Aug. 24, 2001.

English Translation of the first full column at p. 219 of István, L. et al., "Gastrointestinalis vérzések csillapítása thrombin-fibrin készítménnyel," *Orv. Hetil.* 105:219-223, Markusovszky Lajos Foundation (1964), translated by McElroy Translation Company, translation dated Aug. 24, 2001.

English translation of the second-fourth paragraphs at p. 615 of Stoll, v,H.G., "Koagulum-Pyelolithotomie," *Zeitschrift für Urologie* 52:610-615, Veb Georg Thieme Leipzig (1959), translated by McElroy Translation Company, translated dated Aug. 24, 2001.

English Translation of the fourth-eighth paragraphs at p. 479 of Winter, L. et al., "Experimentelle und klinische Anwendung der aus Rinderplasma hergestellten Fibrinprodukte. III. Klinische Verwendung von hämostatischen Fibrinprodukten," *Zentralblatt für Chirurgie* 78:469-479, Vereinigung Mittelrheinischer Chirurgen (1953), translated by McElroy Translation Company, translation dated Aug. 24, 2001.

Berge, S.M., et al., "Pharmaceutical Salts," *J. Pharm. Sci.* 66:1-19, American Pharmaceutical Association (1977).

Desai, S.J., et al., "Investigation of Factors Influencing Release of Solid Drug Dispersed in Inert Matrices," *J. Pharm. Sci.* 54:1459-1464, American Pharmaceutical Association (1965).

Desai, S.J., et al., "Investigation of Factors Influencing Release of Solid Drug Dispersed in Inert Matrices II. Quantitaion of Procedures," *J. Pharm. Sci.* 55:1224-1229, American Pharmaceutical Association (1966).

Desai, S.J., et al., "Investigation of Factors Influencing Release of Solid Drug Dispersed in Inert Matrices III. Quantitative Studies Involving the Polyethylene Plastic Matrix," *J. Pharm. Sci.* 55:1230-1234, American Pharmaceutical Association (1966).

Desai, S.J., et al., "Investigation of Factors Influencing Release of Solid Drug Dispersed in Inert Matrices IV. Some Studies Involving the Polyvinyl Chloride Matrix," *J. Pharm. Sci.* 55:1235-1239, American Pharmaceutical Association (1966).

Higuchi, T., "Mechanism of Sustained-Action Medication. Theoretical Analysis of Rate of Release of Solid Drugs Dispersed in Solid Matrices," *J. Pharm. Sci.* 52:1145-1149, American Pharmaceutical Association (1963).

McKay, I., and Leigh, I., "A1. Growth Factors," in *Growth Factors: A Practical Approach*, McKay, I., and Leigh, I., eds., Oxford University Press, New York, NY, pp. 237-243 (1993).

Pinholt, E.M., et al., "Bone Induction by Composites of Bioresorbable Carriers and Demineralized Bone in Rats: A Comparative Study of Fibrin-Collagen Paste, Fibrin Sealant, and Polyorthoester With Gentamicin," *J. Oral Maxillofac. Surg.* 50:1300-1304, W.B. Saunders Co. (1992).

Greisler, H.P., et al., "Effects of class I heparin binding growth factor and fibronectin on platelet adhesion and aggregation," *J. Vasc. Surg.* 11;665-674, Mosby Year Book, Inc. (1990).

Sugie, I., "Procedure of a new Fibrin film," *Burn Injury* 1:76-83 (1976) (English abstract only).

U.S. Appl. No. 08/328,552, filed Oct. 25, 1994.

Genzyme Biotherapeutic Formulation & Delivery Research Report entitled "Research Report on TGF-β2 Formulated in Fibrin Glue" (dated Jun. 29, 1995).

Bowersox, J.C., Mission Plan of the Division of Military Trauma Research, Letterman Army Institute of Research, pp. 1-16 (Oct. 1992).

Larson, M.J., et al., "Efficacy of a Fibrin Hemostatic Bandage in Controlling Hemorrhage From Experimental Arterial Injuries," *Arch. Surg.* 130:420-422, American Medical Association (Apr. 1995).

Hess, J., "Hemorrhage Control With a Dry Powdered Thrombin and Fibrinogen Bandage," *Nederl. Milit. Geneesk* 49:120-122, (Aug. 1996).

Holcomb, J., et al., "Efficacy of a Dry Fibrin Sealant Dressing for Hemorrhage Control After Ballistic Injury," *Arch. Surg.* 133:32-35, American Medical Association, (1998).

Holcomb, J.B., et al., "New technologies for hemorrhage control," *Curr. Opin. Crit. Care* 3:488-493, Rapid Science Publishers, (1997).

Holcomb, J.B., et al., "Effect of Dry Fibrin Sealant Dressings versus Gauze Packing on Blood Loss in Grade V Liver Injuries in Resuscitates Swine," *J. Trauma: Injury, Infection, Critical Care* 46:49-57, Lippincott Williams & Wilkins, (1999).

Holcomb, J.B., et al., "Dry Fibrin Sealant Dressings Reduce Blood Loss, Resuscitation Volume, and Improve Survival in Hypothermic Coagulopathic Swine with Grade V Liver Injuries," *J. Trauma Injury, Infection and Critical Care* 47:233-242, Lippincott Williams & Wilkins, Inc., (Aug. 1999).

Ingraham, F.C. and Bailey, O.T., "Clinical Use of Products of Human Plasma Fractionation," *J.A.M.A.* 126:680-685, The American Medical Association (1944).

Haudenschild, C., "Vascular Grafts and Organoids" at the Chemical Society, Cells at Interfaces Symposium, Chicago (Aug. 1993).

Larsen, T., "In vitro release of doxycycline from bioabsorbable materials and acrylic strips," *J. Periodontol.* 61:30-34, American Academy of Periodontology (Jan. 1990).

Sugitachi, A., et al., "Locoregional Therapy in Patients with Malignant Pleural Effusion-Experiments on Two Types of 'BAC Therapy'," *Gan To Kagaku Ryoho* (*Cancer and Chemotherapy*) 19:1640-1643, Gan to Kagaku Ryohosha (Aug. 1992).

Unverified English Language Translation of Document AT84, Sugitachi, A., et al., "Locoregional Therapy in Patients with Malignant Pleural Effusion-Experiments on Two Types of 'BAC Therapy'", *Gan To Kagaku Ryoho* (*Cancer and Chemotherapy*) 19:1640-1643, Gan To Kagaku Ryohosha (Aug. 1992).

Unverified English Language Translation of Japanese Patent No. 61-171429, Document AL13.

Unverified English Language Translation of Japanese Patent No. 5-970, Document AM13.

Kim, N.-H., et al., "Effect of Porcine Bone Morphogenetic Protein on Healing of Bone Defect in the Rabbit Radius," *Yonsei Med. J.* 33:54-63, Yonsei University (Mar. 1992).

Ney, A.L., et al., "Fibrin Glue-Antibiotic Suspension in the Prevention of Prosthetic Graft Infection," *J. Trauma* 30:1000-1006, The Williams & Wilkins Co. (Aug. 1990).

* cited by examiner 10 u/ml heparin 20 u/ml heparin 50 u/ml heparin

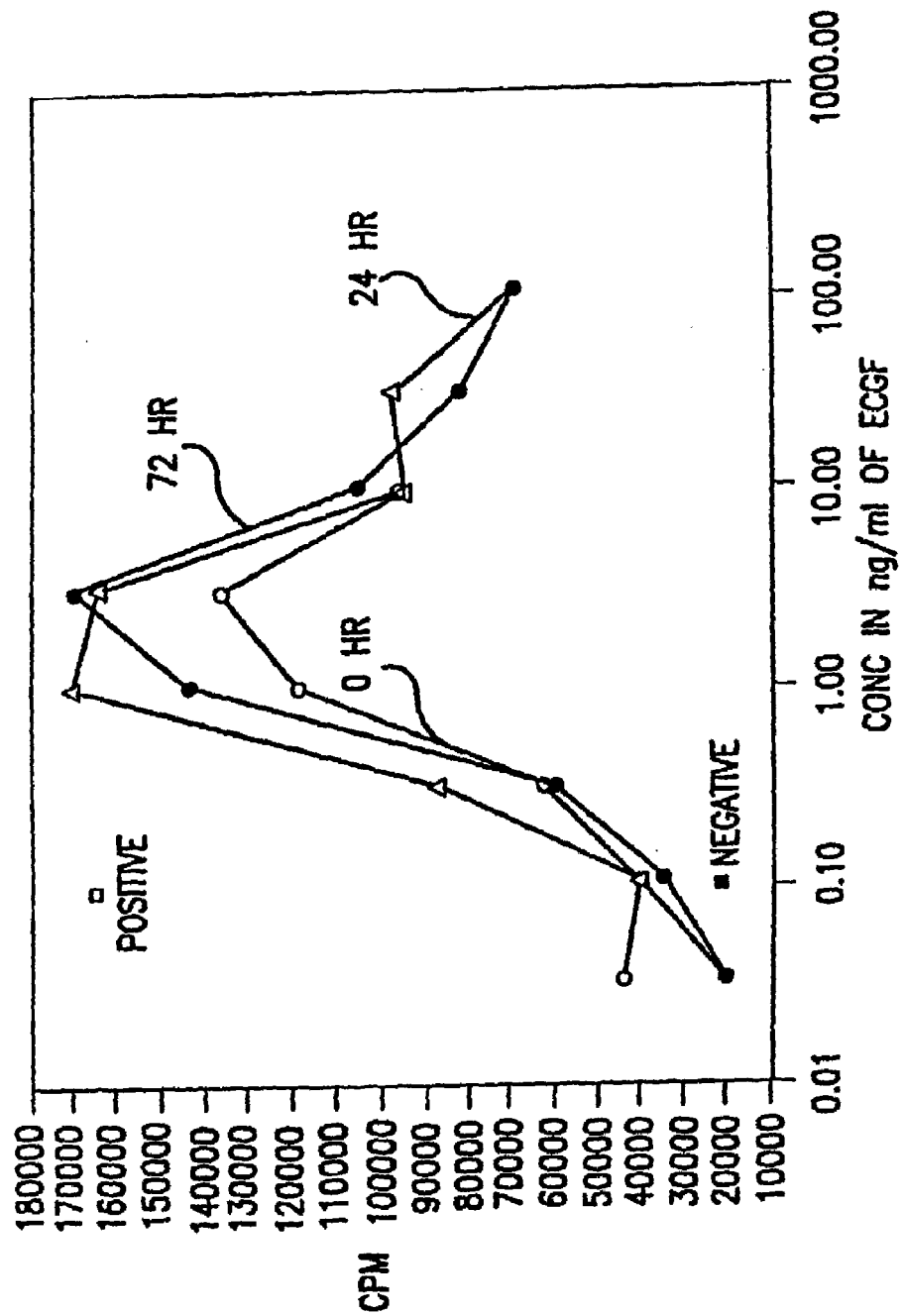

Panel A
Panel B
Panel C
Panel D
Panel E
Panel F
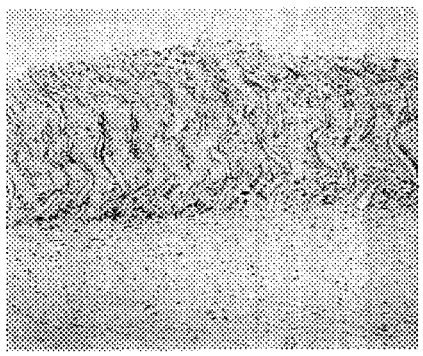
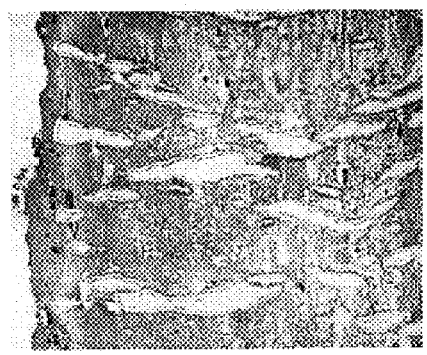
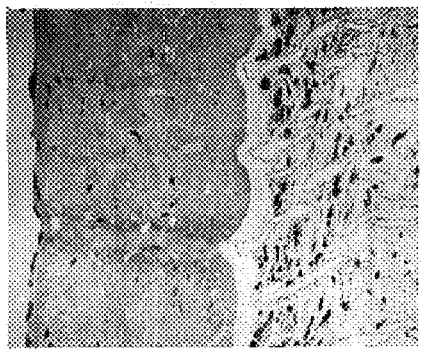
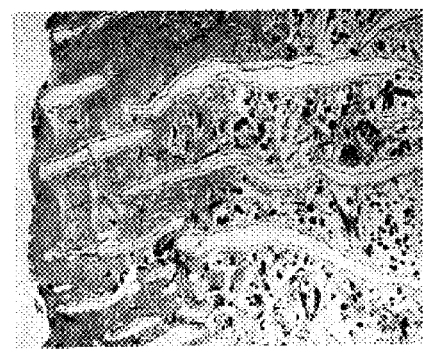
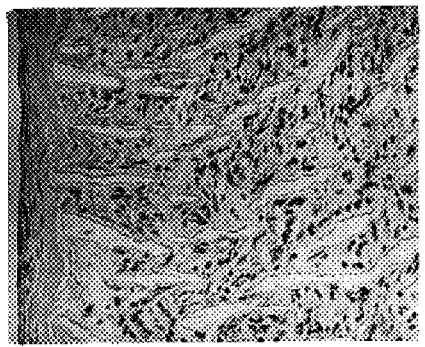
FIG.11

Panel G
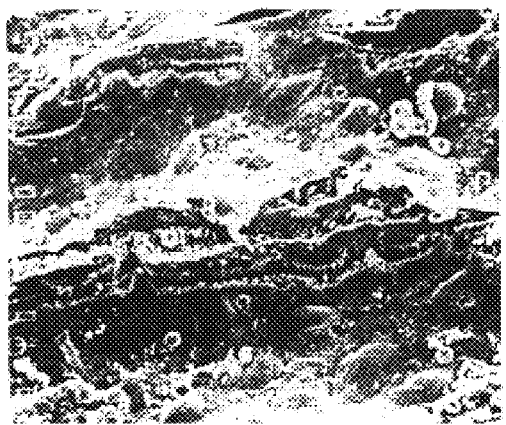
Panel H
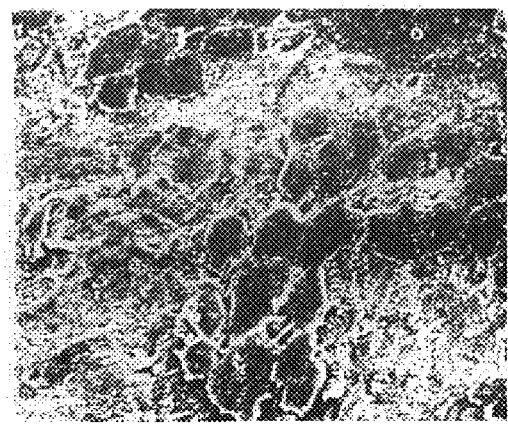
Panel I
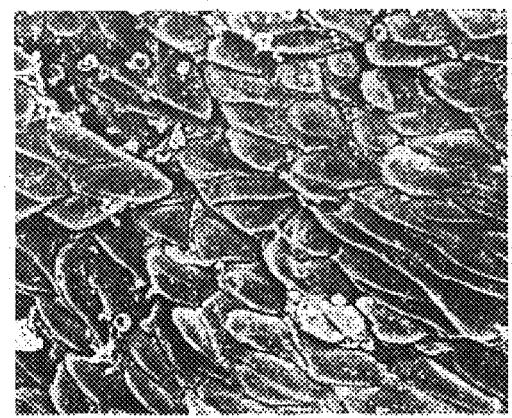
FIG.12

METHODS FOR TREATING WOUND TISSUE AND FORMING A SUPPLEMENTED FIBRIN MATRIX

CROSS REFERENCE TO RELATED APPLICATIONS

This application is a Continuation-in-Part Application of U.S. application Ser. No. 08/351,006, filed Dec. 7, 1994, abandoned, which is a Continuation-in-Part Application of U.S. application Ser. No. 08/328,552, filed Oct. 5, 1994, abandoned, which is a Continuation Application of U.S. application Ser. No. 08/031,164, filed Mar. 12, 1993, abandoned, which is a Continuation-in-Part Application of U.S. application Ser. Nos. 07/618,419 and 07/798,919, filed Nov. 27, 1990, and Nov. 27, 1991, respectively, both of which are abandoned, all of which are herein incorporated by reference.

RIGHTS OF THE UNITED STATES GOVERNMENT IN THIS INVENTION

Under a Cooperative Research and Development Agreement between The American National Red Cross and The U.S. Army Institute of Dental Research, the U.S. Government may have a non-exclusive, irrevocable, paid-up license in one or more embodiments of this invention.

FIELD OF INVENTION

This invention is directed to unsupplemented and supplemented Tissue Sealants (TS), such as fibrin glue (FG), as well as to methods of their production and use. In one embodiment, this invention is directed to TSs which do not inhibit full-thickness skin wound healing. In another embodiment, this invention is directed to TSs which have been supplemented with a growth factor(s) and/or a drug(s), as well as to methods of their production and use. The particular growth factor(s) or drug(s) that is selected is a function of its use.

BACKGROUND OF THE INVENTION

A. Wound Healing and Growth Factors

Wound healing, the repair of lesions, begins almost instantly after injury. It requires the successive coordinated function of a variety of cells and the close regulation of degradative and regenerative steps. The proliferation, differentiation and migration of cells are important biological processes which underlie wound healing, which also involves fibrin clot formation, resorption of the clot, tissue remodeling, such as fibrosis, endothelialization and epithelialization. Wound healing involves the formation of highly vascularized tissue that contains numerous capillaries, many active fibroblasts, and abundant collagen fibrils, but not the formation of specialized skin structures.

The process of wound healing can be initiated by thromboplastin which flows out of injured cells. Thromboplastin contacts plasma factor VII to form factor X activator, which then, with factor V and in a complex with phospholipids and calcium, converts prothrombin into thrombin. Thrombin catalyzes the release of fibrinopeptides A and B from fibrinogen to produce fibrin monomers, which aggregate to form fibrin filaments. Thrombin also activates the transglutaminase, factor XIIIa, which catalyzes the formation of isopeptide bonds to covalently cross-link the fibrin filaments. Alpha$_2$-antiplasmin is then bound by factor XIII onto the fibrin filaments to thereby protect the filaments from degradation by plasmin (see, for example, Doolittle et al., *Ann. Rev. Biochem.* 53:195–229 (1984)).

When a tissue is injured, polypeptide growth factors, which exhibit an array of biological activities, are released into the wound where they play a crucial role in healing (see, e.g., *Hormonal Proteins and Peptides* (Li, C. H., ed.) Volume 7, Academic Press, Inc., New York, N.Y. pp. 231–277 (1979) and Brunt et al., *Biotechnology* 6:25–30 (1988)). These activities include recruiting cells, such as leukocytes and fibroblasts, into the injured area, and inducing cell proliferation and differentiation. Growth factors that may participate in wound healing include, but are not limited to: platelet-derived growth factors (PDGFs); insulin-binding growth factor-1 (IGF-1); insulin-binding growth factor-2 (IGF-2); epidermal growth factor (EGF); transforming growth factor-α (TGF-α); transforming growth factor-β (TGF-β); platelet factor 4 (PF-4); and heparin binding growth factors one and two (HBGF-1 and HBGF-2, respectively).

PDGFs are stored in the alpha granules of circulating platelets and are released at wound sites during blood clotting (see, e.g., Lynch et al., *J. Clin. Invest.* 84:640–646 (1989)). PDGFs include: PDGF; platelet derived angiogenesis factor (PDAF); TGF-β; and PF-4, which is a chemoattractant for neutrophils (Knighton et al., in *Growth Factors and Other Aspects of Wound Healing: Biological and Clinical Implications*, Alan R. Liss, Inc., New York, N.Y., pp. 319–329 (1988)). PDGF is a mitogen, chemoattractant and a stimulator of protein synthesis in cells of mesenchymal origin, including fibroblasts and smooth muscle cells. PDGF is also a nonmitogenic chemoattractant for endothelial cells (see, for example, Adelmann-Grill et al., *Eur. J. Cell Biol.* 51:322–326 (1990)).

IGF-1 acts in combination with PDGF to promote mitogenesis and protein synthesis in mesenchymal cells in culture. Application of either PDGF or IGF-1 alone to skin wounds does not enhance healing, but application of both factors together appears to promote connective tissue and epithelial tissue growth (Lynch et al., *Proc. Natl. Acad. Sci.* 76:1279–1283 (1987)).

TGF-β is a chemoattractant for macrophages and monocytes. Depending upon the presence or absence of other growth factors, TGF-β may stimulate or inhibit the growth of many cell types. For example, when applied in vivo, TGF-β increases the tensile strength of healing dermal wounds. TGF-β also inhibits endothelial cell mitosis, and stimulates collagen and glycosaminoglycan synthesis by fibroblasts.

Other growth factors, such as EGF, TGF-α, the HBGFs and osteogenin are also important in wound healing. EGF, which is found in gastric secretions and saliva, and TGF-α, which is made by both normal and transformed cells, are structurally related and may recognize the same receptors. These receptors mediate proliferation of epithelial cells. Both factors accelerate reepithelialization of skin wounds. Exogenous EGF promotes wound healing by stimulating the proliferation of keratinocytes and dermal fibroblasts (Nanney et al., *J. Invest. Dermatol.* 83:385–393 (1984) and Coffey et al., *Nature* 328:817–820 (1987)). Topical application of EGF accelerates the rate of healing of partial thickness wounds in humans (Schultz et al., *Science* 235:350–352 (1987)). Osteogenin, which has been purified from demineralized bone, appears to promote bone growth (see, e.g., Luyten et al., *J. Biol. Chem.* 264:13377 (1989)). In addition, platelet-derived wound healing formula, a platelet extract which is in the form of a salve or ointment for topical application, has been described (see, e.g., Knighton et al., *Ann. Surg.* 204:322–330 (1986)).

The Heparin Binding Growth Factors (HBGFs), also known as Fibroblast Growth Factors (FGFs), which include acidic HBGF (aHBGF also known as HBFG-1 or FGF-1) and basic HBGF (bHBGF also known as HBGF-2 or FGF-2), are potent mitogens for cells of mesodermal and neuroectoderrnal lineages, including endothelial cells (see, e.g., Burgess et al., *Ann. Rev. Biochem.* 58:575–606 (1989)). In addition, HBGF-1 is chemotactic for endothelial cells and astroglial cells. Both HBGF-1 and HBGF-2 bind to heparin, which protects them from proteolytic degradation. The array of biological activities exhibited by the HBGFs suggests that they play an important role in wound healing.

Basic fibroblast growth factor (FGF-2) is a potent stimulator of angiogenesis and the migration and proliferation of fibroblasts (see, for example, Gospodarowicz et al., *Mol. Cell. Endocinol.* 46:187–204 (1986) and Gospodarowicz et al., *Endo. Rev.* 8:95–114 (1985)). Acidic fibroblast growth factor (FGF-1) has been shown to be a potent angiogenic factor for endothelial cells (Burgess et al., supra, 1989). However, it has not been established if any FGF growth factor is chemotactic for fibroblasts.

Growth factors are, therefore, potentially useful for specifically promoting wound healing and tissue repair. However, their use to promote wound healing has yielded inconsistent results (see, e.g., Carter et al., in *Growth Factors and Other Aspects of Wound Healing: Biological and Clinical Implications*, Alan R. Liss, Inc., New York, N.Y., pp. 303–317 (1988)). For example, PDGF, IGF-1, EGF, TGF-α, TGF-β and FGF (also known as HBGF) applied separately to standardized skin wounds in swine had little effect on the regeneration of connective tissue or epithelium in the wounds (Lynch et al., *J. Clin. Invest.* 84:640–646 (1989)). Of the factors tested, TGF-β stimulated the greatest response alone. However, a combination of factors, such as PDGF-bb homodimer and IGF-1 or TGF-α produced a dramatic increase in connective tissue regeneration and epithelialization. (Id.) Tsuboi et al. have reported that the daily application of bFGF to an open wound stimulated wound healing in healing-impaired mice but not in normal mice (*J. Exp. Med.* 172:245–251 (1990)). On the other hand, the application to human skin wounds of crude preparations of porcine or bovine platelet lysate, which presumably contained growth factors, increased the rate at which the wounds closed, the number of cells in the healing area, the growth of blood vessels, the total rate of collagen deposition and the strength of the scar tissue (Carter et al., supra).

The reasons for such inconsistent results are not known, but might be the result of difficulty in applying growth factors to a wound in a manner in which they can exhibit their normal array of biological activities. For example, it appears that some growth factor receptors must be occupied for at least 12 hours to produce a maximal biologic effect (Presta et al., *Cell Regul.* 2:719–726(1991) and Rusnati et al., *J. Cell Physiol.* 154:152–161(1993)). Because of such inconsistent results, the role played by exogenously applied growth factors in stimulating wound healing is not clear. Further, a means by which growth factors might be applied to wounds to produce prolonged contact between the wound and the growth factor(s) is not presently known.

B. TSs

Surgical adhesives and TSs which contain plasma proteins are used for sealing internal and external wounds, such as in bones and skin, to reduce blood loss and maintain hemostasis. Such TSs contain blood clotting factors and other blood proteins. FG, also called fibrin sealant, is a gel similar to a natural clot which is prepared from plasma. The precise components of each FG are a function of the particular plasma fraction which is used as a starting material. Fractionation of plasma components can be effected by standard protein purification methods, such as ethanol, polyethylene glycol, and ammonium sulfate precipitation, ion exchange, and gel filtration chromatography. Typically FG contains a mixture of proteins including traces of albumin, fibronectin and plasminogen. In Canada, Europe and possibly elsewhere, commercially available FG typically also contains aprotinin as a stabilizer.

FGs generally are prepared from: (1) a fibrinogen concentrate, which contains fibronectin, Factor XIII, and von Willebrand factor; (2) dried human or bovine thrombin; and (3) calcium ions. Commercially prepared FGs generally contain bovine components. The fibrinogen concentrate can be prepared from plasma by cryoprecipitation followed by fractionation, to yield a composition that forms a sealant or clot upon mixture with thrombin and an activator of thrombin such as calcium ions. The fibrinogen and thrombin concentrates are prepared in lyophilized form and are mixed with a solution of calcium chloride immediately prior to use. Upon mixing, the components are applied to a tissue where they coagulate on the tissue surface and form a clot that includes cross-linked fibrin. Factor XIII, which is present in the fibrinogen concentrate, catalyzes the cross-linking.

Australian Patent 75097/87 describes a one-component adhesive, which contains an aqueous solution of fibrinogen, factor XIII, a thrombin inhibitor, such as antithrombin III, prothrombin factors, calcium ions, and, if necessary, a plasmin inhibitor. Stroetmann, U.S. Pat. Nos. 4,427,650 and 4,427,651, describes the preparation of an enriched plasma derivative in the form of a powder or sprayable preparation for enhanced wound closure and healing that contains fibrinogen, thrombin and/or prothrombin, and a fibrinolysis inhibitor, and may also contain other ingredients, such as a platelet extract. Rose et al., U.S. Pat. Nos. 4,627,879 and 4,928,603, disclose methods for preparing cryoprecipitated suspensions that contain fibrinogen and Factor XIII and their use to prepare a FG. JP 1-99565 discloses a kit for the preparation of fibrin adhesives for wound healing. Alterbaum (U.S. Pat. No. 4,714,457) and Morse et al. (U.S. Pat. No. 5,030,215) disclose methods to produce autologous FG. In addition, improved FG delivery systems have been disclosed elsewhere (Miller et al., U.S. Pat. No. 4,932,942 and Morse et al., PCT Application WO 91/09641).

IMMUNO A G (Vienna, Austria) and BEHRINGWERKE A G (Germany) (Gibble et al., *Transfusion* 30:741–747 (1990)) presently have FGs on the market in Europe and elsewhere (see, e.g., U.S. Pat. Nos. 4,377,572 and 4,298,598, which are owned by IMMUNO A G). TSs are not commercially available in the U.S. However, the American National Red Cross and BAXTER/HYLAND (Los Angeles, Calif.) have recently co-developed a FG (ARC/BH FG) which is now in clinical studies.

The TSs which are used clinically outside of the U.S. pose certain clinical risks and have not been approved by the Food and Drug Administration for use in the USA. For example, the TSs available in Europe contain proteins of non-human origin such as aprotinin and bovine thrombin. Since these proteins are of non-human origin, people may develop allergic reactions to them. In Europe heat inactivation is used to inactivate viruses which may be present in the components of the FG. However, this heat inactivation method may produce denatured proteins in the FG which may also be allergenic. In addition, there is concern that this inactivation method will not inactivate prions which cause bovine spongiform encephalopathy, "mad cow disease," which may be present in the TS due to the use of bovine proteins therein. Since this disease appears to have already crossed from sheep, in which it is called "scrapies," to cows, it is not an insignificant concern that it could infect humans.

The ARC/BH FG has advantages over the TSs available in Europe because it does not contain bovine proteins. For example, the ARC/BH TS contains human thrombin instead of bovine thrombin and does not contain aprotinin. Since the ARC/BH FG does not contain bovine proteins it should be less allergenic in humans than those TSs available in Europe. In addition, the ARC/BH FG is virally inactivated by a solvent detergent method which produces fewer denatured proteins and thus is less allergenic than those available in Europe. Therefore, the ARC/BH FG possesses advantages over the TSs which are now commercially available in other countries.

FG is primarily formulated for clinical topical application and is used to control bleeding, maintain hemostasis and promote wound healing. The clinical uses of FG have recently been reviewed (Gibble et al., *Transfusion* 30:741–747 (1990); Lerner et al., *J. Surg. Res.* 48:165–181 (1990)). By sealing tissues FG prevents air or fluid leaks, induces hemostasis, and may contribute to wound healing indirectly by reducing or preventing events which may interfere with wound healing such as bleeding, hematomas, infections, etc. Although FG maintains hemostasis and reduces blood loss, it has not yet been shown to possess true wound healing properties. Because FG is suitable for both internal and external injuries, such as bone and skin injuries, and is useful to maintain hemostasis, it is desirable to enhance its wound healing properties.

FG with a fibrinogen concentration of approximately 39 μl and a thrombin concentration of 200–600 U/ml has produced clots with significantly increased stress, energy absorption and elasticity values (Byrne et al., *Br. J. Surg.* 78:841–843 (1991)). Perforated Teflon cylinders filled with fibrin clot (5 mg/ml) and implanted subcutaneously stimulated the formation of granulation tissue, including an increased precipitation of collagen, when compared to empty cylinders (Hedelin et al., *Eur. Surg. Res.* 15:312 (1983)).

C. Bone Wounds and Their Repair

The sequence of bone induction was first described by Urist et al. using demineralized cortical bone matrix (*Clin. Orthop. Rel. Res.* 71:271 (1970) and *Proc. Natl. Acad. Sci. USA* 70:3511 (1973)). Implanted subcutaneously in allogeneic recipients, demineralized cortical bone matrix releases factors which act as local mitogens to stimulate the proliferation of mesenchymal cells (Rath et al., *Nature* (Lond.) 278:855 (1979)). New bone formation occurs between 12 and 18 days postimplantation. Ossicle development replete with hematopoietic marrow lineage occurred by day 21 (Reddi, A., In *Extracellular Matrix Biochemistry* (Piez et al., ed.) Elsevier, New York, N.Y., pp. 375–412 (1984)).

Demineralized bone matrix (DBM) is a source of osteoinductive proteins known as bone morphogenetic proteins (BMP), and growth factors which modulate the proliferation of progenitor bone cells (see, e.g., Hauschka et al., *J. Biol. Chem.* 261:12665–12674 (1986) and Canalis et al., *J. Clin. Invest.* 81:277–281 (1988)). Eight BMPs have now been identified and are abbreviated BMP-1 through BMP-8. BMP-3 and BMP-7 are also known as osteogenin and osteogenic protein-1 (OP-1), respectively.

Unfortunately, DBM materials have little clinical use unless combined with particulate marrow autografts. There is a limit to the quantity of DBM that can be surgically placed into a recipient's bone to produce a therapeutic effect. In addition, resorption has been reported to be at least 49% (Toriumi et al., *Arch. Otolaryngo. Head Neck Surg.* 116: 676–680 (1990)).

DBM powder and osteogenin may be washed away by tissue fluids before their osteoinductive potential is expressed. In addition, seepage of tissue fluids into DBM-packed bone cavities or soft-tissue collapse into the wound bed are two factors that may significantly affect the osteoinductive properties of DBM and osteogenin. Soft-tissue collapse into the wound bed may likewise inhibit the proper migration of osteocompetent stem cells into the wound bed.

Human DBM in powder form is currently used by American dentists to pack jaw bone cavities created during oral surgery. However, DBM in powder form is difficult to use.

Purified BMPs have osteoinductive effects in animals when delivered by a variety of means including FG (Hattori, T., Nippon. Seikeigeka. Gakkai. Zasshi. 64:824–834 (1990); Kawamura et al., *Clin. Orthop. Rel. Res.* 235:302–310 (1988); Schlag et al., *Clin. Orthop. Rel. Res.* 227:269–285 (1988) and Schwarz et al., *Clin. Orthop. Rel. Res.* 238: 282–287 (1989)) and whole blood clots (Wang et al., *J. Cell. Biochem.* 15 F:Q20 Abstract (1990)). However, Schwarz et al. (supra.) demonstrated neither a clear positive or negative effect of FG on ectopic osteoinduction or BMP-dependent osteoregeneration. Kawamura et al. (supra.) found a synergistic effect when partially purified BMP in FG was tested in an ectopic non-bony site. Therefore, these results are inconsistent and confusing.

TS also can serve as a "scaffold" which cells can use to move into a wounded area to generate new tissues. However, commercially available preparations of FG and other TSs are too dense to allow cell migration into and through them. This limits their effectiveness in some in vivo uses.

In one type of bone wound, called bone nonunion defects, there is a minimal gap above which no new bone formation occurs naturally. Clinically, the treatment for these situations is bone grafting. However, the source of bone autografts is usually limited and the use of allogeneic bones involves a high risk of viral contamination. Because of this situation, the use of demineralized, virally inactivated bone powder is an attractive solution.

D. Vascular Prostheses

Artificial vascular prostheses are frequently made out of polytetrafluoroethylene (PTFE) and are used to replace diseased blood vessels in humans and other animals. To maximize patency rates and minimize the thrombogenicity of vascular prostheses various techniques have been used including seeding of nonautologous endothelial cells onto the prothesis. Various substrates which adhere both to the vascular graft and endothelial cells have been investigated as an intermediate substrate to increase endothelial cell seeding. These substrates include preclotted blood (Herring et al., *Surgery* 84:498–504 (1978)), F G (Rosenman et al., *J. Vasc. Surg.* 2:778–784 (1985); Schrenk et al., *Thorac. Cardiovasc. Surg.* 35:6–10 (1986); Köveker et al., *Thorac. Cardiovasc. Surgeon* 34: 49–51 (1986) and Zilla et al., *Surgery* 105:515–522 (1989)), fibronectin (see, e.g., Kesler et al., *J. Vasc. Surg.* 3:58–64 (1986); Macarak et al., *J. Cell Physiol.* 116.76–86 (1983) and Ramalanjeona et al., *J. Vasc. Surg.* 3:264–272 (1986)), or collagen (Williams et al., *J. Surg. Res.* 38:618–629 (1985)). However, one general problem with these techniques is that nonautologous cells were used for the seeding (see, e.g., Schrenk et al., supra) thus raising the possibility of tissue rejection. In addition, a confluent endothelium is usually never established and requires months to do so if it is. As a result of this delay, there is a high occlusion rate of vascular prostheses (see, e.g., Zilla et al., supra).

E. Angiogenesis

Angiogenesis is the induction of new blood vessels. Certain growth factors such as HBGF-1 and HBGF-2 are angiogenic. However, their in vivo administration attached to: collagen sponges (Thompson et al., *Science* 241:1349–1352 (1988)); beads (Hayek et al., *Biochem. Biophys. Res. Commun.* 147:876–880 (1987)); solid PTFE fibers coated with collagen arranged in a sponge-like structure (Thompson et al., *Proc. Natl. Acad. Sci. USA* 86:7928–7932 (1989)); or by infusion (Puumala et al., *Brain Res.* 534:283–286 (1990)) resulted in the generation of random, disorganized blood vessels. These growth factors have not been used successfully to direct the growth of a new blood vessel(s) at a given site in vivo. In addition, fibrin gels (0.5–10 mg/ml) implanted subcutaneously in plexiglass chambers induce angiogenesis within 4 days of implantation, compared to empty chambers, or chambers filled with sterile culture medium (Dvorak et al., *Lab. Invest.* 57:673 (1987)).

F. Site-Directed, Localized Drug Delivery

An efficacious, site-directed, drug delivery system is greatly needed in several areas of medicine. For example, localized drug delivery is needed in the treatment of local infections, such as in periodontitis, where the systemic administration of antimicrobial agents is ineffective. The problem after systemic administration usually lies in the low concentration of the antimicrobial agent which can be achieved at the target site. To raise the local concentration a systemic dose increase may be effective but also may produce toxicity, microbial resistance and drug incompatibility. To circumvent some of these problems, several alternative methods have been devised but none are ideal. For example, collagen and/or fibrinogen dispersed in an aqueous medium as an amorphous flowable mass, and a proteinaceous matrix composition which is capable of stable placement, have also been shown to locally deliver drugs (Luck et al., U.S. Reissue Patent 33,375; Luck et al., U.S. Pat. No. 4,978,332).

A variety of antibiotics (AB) have been reported to be released from FG, but only at relatively low concentrations and for relatively short periods of time ranging from a few hours to a few days (Kram et al., *J. Surg. Res.* 50:175–178 (1991)). Most of the ABs have been in freely water soluble forms and have been added into the TS while it was being prepared. However, the incorporation of tetracycline hydrochloride tetracycline hydrochloride (TET HCl) and other freely water soluble forms of ABs into FG has interfered with fibrin polymerization during the formation of the AB-supplemented FG (Schlag et al., *Biomaterials* 4:29–32 (1983)). This interference limited the amount and concentration of the TET HCl that could be achieved in the AB-FG mixture and appeared to be AB concentration dependent. The relatively short release time of the AB from the FG may reflect the relatively short life of the AB-supplemented TS or the form and/or quantity of the AB in the AB-TS.

G. Controlled Drug Release From TSs

For some clinical applications controlled, localized drug release is desirable. As discussed above, some drugs, especially ABs, have been incorporated into and been released from TSs such as FG. However, there is little or no control over the duration of the drug release which apparently is at least partially a reflection of the relatively short life of the drug-supplemented FG. Therefore, a means to stabilize FG and other TSs to allow for extended, localized drug release is desirable and needed, as are new techniques for the incorporation and extended release of other supplements from TS.

H. The Disclosed TS Preparations Provide Life-Saving Emergency Treatment for Trauma Wounds Despite continued advances in trauma care, a significant percentage of the population, both military and civilian, suffer fatal or severe hemorrhage every year. An alarming number of fatalities are preventable since the occur in the presence of those who could achieve life-saving control of their wounds given adequate tools and training. The availability of the herein-disclosed TS satisfies the long-felt need for a advanced, easy-to-use, field-ready hemostatic preparation, to permit not only trained medical personnel, but even untrained individuals to rapidly reduce bleeding in trauma victims. Utilization of the disclosed TS preparations will result in a two-fold benefit: the reduction of trauma death, and the decreased demand upon the available blood supply.

The disclosed technology would also be available for the treatment of massed casualties in disaster situation. When severe natural or man-made disasters occur, local hospitals and clinics may be overwhelmed by the number of individuals requiring trauma care. Combined with the isolating effects of such disasters, the resulting demand for blood and blood products often exceeds the locally available supplies. In many cases, the demand upon the local medical personnel also exceeds the availed number of trained individuals. As a result, less seriously injured persons may be turned-away or given sub-optimal care. The availability of the easy-to-use, self-contained TS preparations disclosed below will permit local medical personnel and disaster relief workers to provide the injured with temporary treatment until definitive care becomes available. Moreover, the disclosed TS preparations will permit self-treatment in disaster victims, until medical assistance can be provided.

Often the only form of medical treatment that can be applied under such circumstances to prevent death due to blood loss is pressure dressings, tourniquets and pressure points. Unfortunately, however, each of these treatments requires continuous monitoring and attention. Since such attention is not always possible in emergency or disaster situations, there is a clear need in the art for a simple, fast-acting, first-aid treatment which can successfully control excessive blood loss.

The application of the disclosed TS preparations to the military is readily apparent, particularly in isolated battlefield situations. The single greatest cause of death on the battlefield is exsanguination, which until now has accounted for up to 50% of all combat casualties.

SUMMARY OF THE INVENTION

In one embodiment, this invention provides a composition of matter, comprising a TS, wherein the sealant does not inhibit full-thickness skin wound healing.

In another embodiment, this invention provides a composition of matter, comprising: a TS, wherein the total protein concentration of the sealant is less than 30 mg/ml.

In another embodiment, this invention provides a composition of matter comprising a supplemented TS wherein the total protein concentration is less than 30 mg/ml and the supplement is a growth factor(s) and/or a drug(s).

In another embodiment, this invention provides a composition of matter comprising a supplemented TS wherein the total protein concentration is greater than 30 mg/ml and the supplement is a growth factor(s) and/or a drug(s).

In another embodiment, this invention provides a composition of matter that promotes the directed migration of animal cells, comprising: a TS; and an effective concentration of at least one growth factor, wherein the concentration of the growth factor is effective in promoting the directed migration of the animal cells.

In another embodiment, the present invention provides a composition of matter that promotes wound healing, comprising: a TS; and an effective concentration of at least one growth factor, wherein the concentration is effective in promoting wound healing.

In another embodiment, the present invention provides a composition of matter that promotes the endothelialization of a vascular prosthesis, comprising: a TS; and an effective concentration of at least one growth factor, wherein the concentration is effective in promoting the endothelialization of a vascular prosthesis.

In another embodiment, the present invention provides a composition of matter that promotes the proliferation and/or differentiation of animal cells, comprising: a TS; and an effective concentration of at least one growth factor, wherein the concentration is effective in promoting proliferation and/or differentiation of animal cells.

In another embodiment, the present invention provides a composition of matter that promotes the localized delivery of at least one drug, comprising: a TS; and at least one drug.

In another embodiment, the present invention provides a composition of matter that promotes the localized delivery of at least one growth factor, comprising: a TS; and at least one growth factor.

In another embodiment, the present invention provides a process for promoting the healing of wounds, comprising applying to the wound, a composition that contains a TS and an effective concentration of at least one growth factor, wherein the concentration is effective to promote wound healing.

In another embodiment, the present invention provides a process for promoting the endothelialization of a vascular prosthesis, comprising applying to the vascular prosthesis a composition that contains a TS and an effective concentration of at least one growth factor, wherein the concentration is effective to promote the endothelialization of a vascular prothesis.

In another embodiment, the present invention provides a process for promoting the proliferation and/or differentiation of animal cells, comprising placing the cells in sufficient proximity to a TS which contains an effective concentration of at least one growth factor, wherein the concentration is effective in promoting the proliferation and/or differentiation of the cells.

In a further embodiment, the present invention provides a process for the localized delivery of at least one drug to a tissue, comprising applying to the tissue a TS which contains at least one drug.

In another embodiment, the present invention provides a process for the localized delivery of at least one growth factor to a tissue, comprising applying to the tissue a TS which contains at least one growth factor.

In another embodiment, this invention provides a process for producing the directed migration of animal cells, comprising: placing in sufficient proximity to the cells, a TS which contains an effective concentration of at least one growth factor, wherein the concentration is effective to produce the desired directed migration of said cells.

In another embodiment, this invention provides a simple to use, fast acting, field-ready fibrin bandage for applying a tissue sealing composition to wounded tissue in a patient, comprising an occlusive backing, affixed to which is a layer of dry materials comprising an effective amount, in combination, of (a) dry, virally-inactivated, purified fibrinogen, (b) dry, virally-inactivated, purified thrombin, and as necessary (c) effective amounts of calcium and/or Factor XIII to produce a tissue-sealing fibrin clot upon hydration.

In a further embodiment, this invention provides a method of treating wounded tissue in a patient by applying to said wound a fibrin bandage, comprising: (1) a occlusive backing, affixed to which is a layer of dry materials comprising an effective amount, in combination, of (a) dry, virally-inactivated, purified fibrinogen, (b) dry, virally-inactivated, purified thrombin, and as necessary (c) effective amounts of calcium and/or Factor XIII to produce a tissue-sealing fibrin clot upon hydration.

In yet another embodiment, this invention provides a simple to use, fast acting, field-ready fibrin dressing for treating wounded tissue in a patient, is formulated as an expandable foam comprising an effective amount, in combination, of (1) virally-inactivated, purified fibrinogen, (2) virally-inactivated, purified thrombin, and as necessary (3) calcium and/or Factor XIII; wherein said composition does not significantly inhibit full-thickness skin wound healing.

While in a further embodiment, this invention provides a method of treating wounded tissue in a patient by applying to said wound a tissue sealant expandable foam dressing, comprising an effective amount, in combination, of (1) virally-inactivated, purified fibrinogen, (2) virally-inactivated, purified thrombin, and as necessary (3) calcium and/or Factor XIII; wherein said composition does not significantly inhibit full-thickness skin wound healing.

In the embodiments of this invention, the TS may be FG.

In the various embodiments of the invention FG may be made from the mixing of topical fibrinogen complex (TFC), human thrombin and calcium chloride. Varying the concentration of the TFC has the most significant effect upon the density of the final FG matrix. Varying the concentration of the thrombin has an insignificant effect upon the total protein concentration of the final FG, but has a profound effect upon the time required for the polymerization of the fibrinogen component of the TFC into fibrin. While this effect is well known, it is not generally appreciated that it may be used to maximize the effectiveness of the FG, when it is used alone or supplemented. Because of this effect one can alter the time between the mixing of the FG components and the setting of the FG. Thus, one can allow the FG to flow more freely into deep crevices in a wound, permitting it to fill the wound completely before the FG sets. Alternatively, one can allow the FG to set quickly enough to prevent it from exiting the wound site, especially if the wound is leaking fluid under pressure (i.e., blood, lymph, intercellular fluid, etc). This property is also important to keep the FG from clogging delivery devices with long passages, i.e., catheters, endoscopes, etc., which is important to allow the application of the FG or supplemented FG to sites in the body that are only accessible by surgery. This effect is also important in keeping the insoluble supplements in suspension and preventing them from settling in the applicator or in the tissue site.

As used herein, TFC is a lyophilized mixture of human plasma proteins which have been purified and virally inactivated. When reconstituted TFC contains:

Total Protein: 100–130 mg/ml
Fibrinogen: (as clottable protein) 80% of total protein (minimum)
Albumin (Human): 5–25 mg/ml
Plasminogen: 5 mg/ml
Factor XIII: 10–40 Units/ml
Polysorbate-80: 0.3% (maximum)
pH: 7.1–7.5.

The reconstituted TFC may also contain trace amounts of fibronectin.

As used herein, human thrombin is a lyophilized mixture of human plasma proteins, which have been purified and virally inactivated. When reconstituted it contains:
Thrombin Potency: 300±50 International Units/ml
Albumin (Human): 5 mg/ml
Glycine: 0.3 M±05 M
pH: 6.5–7.1.

Calcium chloride is added in sufficient concentration to activate the thrombin. As long as there is sufficient calcium, its concentration is not important.

In the compositions of this invention containing a growth factor, the composition may contain an inhibiting compound(s) and/or potentiating compound(s), wherein the inhibiting compound(s) inhibit the activities of the sealant that interfere with any of the biological activities of the growth factor, the potentiating compound(s) potentiate, mediate or enhance any of the biological activities of the growth factor, and wherein the concentration of the inhibiting or potentiating compound is effective for achieving the inhibition, potentiation, mediation or enhancement.

The growth factor-supplemented TSs of this invention are useful for promoting the healing of wounds, especially those that do not readily heal, such as skin ulcers in diabetic individuals, and for delivering growth factors including, but not limited to, FGF-1, FGF-2, FGF-4, PDGFs, EGFs, IGFs, PDGF-bb, BMP-1, BMP-2, OP-1, TGF-β, cartilage-inducing factor-A (CIF-A), cartilage-inducing factor-B (CIF-B), osteoid-inducing factor (OIF), angiogenin(s), endothelins, hepatocyte growth factor and keratinocyte growth factor, and providing a medium for prolonged contact between a wound site and the growth factor(s). The growth factor-supplemented TS may be used to treat burns and other skin wounds and may comprise a TS and, in addition to the growth factor(s), an antibiotic(s) and/or an analgesic(s), etc. The growth factor-supplemented TS may be used to aid in the engraftment of a natural or artificial graft, such as skin to a skin wound. They may also be used cosmetically, for example in hair transplants, where the TS might contain FGF, EGF, antibiotics and minoxidil, as well as other compounds. An additional cosmetic use for the compositions of this invention is to treat wrinkles and scars instead of using silicone or other compounds to do so. In this embodiment, for example, the TS may contain FGF-1, FGF-4, and/or PDGFs, and fat cells. The growth factor-supplemented TSs may be applied to surgical wounds, broken bones or gastric ulcers and other such internal wounds in order to promote healing thereof. The TSs of this invention may be used to aid the integration of a graft, whether artificial or natural, into an animal's body as for example when the graft is composed of natural tissue. The TSs of this invention can be used to combat some of the major problems associated with certain conditions such as periodontitis, namely persistent infection, bone resorption, loss of ligaments and premature re-epithelialization of the dental pocket.

In another embodiment, this invention provides a mixture of FG, DBM and/or purified BMP's. This mixture provides a matrix that allows the cellular components of the body to migrate into it and thus produce osteoinduction where needed. The matrix composition in terms of proteins (such as fibrinogen and Factor XIII), enzymes (such as thrombin and plasmin), BMPs, growth factors and DBM and their concentrations are adequately formulated to optimize the longevity of this temporal scaffolding structure and the osteoinduction which needs to occur. All the FG components are biodegradable but during osteogenesis the mixture provides a non-collapsible scaffold that can determine the shape and location of the newly formed bone. Soft tissue collapse into the bony nonunion defect, which is a problem in bone reconstructive surgery, will thus be avoided. The use of TS supplemented with growth factors such as CIF-A and CIF-B, infra, which promote cartilage development, will be useful in the reconstruction of lost or damaged cartilage and/or damaged bone.

In a preferred embodiment, an effective concentration of HBGF-1 is added to a FG in order to provide a growth factor-supplemented TS that possesses the ability to promote wound healing. In another preferred embodiment, an effective amount of a platelet-derived extract is added to a FG. In other preferred embodiments, an effective concentration of a mixture of at least two growth factors are added to FG and an effective amount of the growth factor(s)-supplemented FG is applied to the wounded tissue.

In addition to growth factors, drugs, polyclonal and monoclonal antibodies and other compounds, including, but not limited to, DBM and BMPs may be added to the TS. They accelerate wound healing, combat infection, neoplasia, and/or other disease processes, mediate or enhance the activity of the growth factor in the TS, and/or interfere with TS components which inhibit the activities of the growth factor in the TS. These drugs may include, but are not limited to: antibiotics, such as tetracycline and ciprofloxacin; antiproliferative/cytotoxic drugs, such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as α- or β- or γ-Interferon, α- or β-tumor necrosis factor, and interleukins; colony stimulating factors; erythropoietin; antifungals, such as diflucan, ketaconizole and nystatin; antiparasitic agents, such as pentamidine; anti-inflammatory agents, such as α-1-anti-trypsin and α-1-antichymotrypsin; steroids; anesthetics; analgesics; and hormones. Other compounds which may be added to the TS include, but are not limited to: vitamins and other nutritional supplements; hormones; glycoproteins; fibronectin; peptides and proteins; carbohydrates (both simple and/or complex); proteoglycans; antiangiogenins; antigens; oligonucleotides (sense and/or antisense DNA and/or RNA); BMPs; DBM; antibodies (for example, to infectious agents, tumors, drugs or hormones); and gene therapy reagents. Genetically altered cells and/or other cells may also be included in the TSs of this invention. The osteoinductive compounds which can be used in practicing this invention include, but are not limited to: osteogenin (BMP3); BMP-2; OP-1; BMP-2A, -2B, and -7; TGF-β, HBGF-1 and -2; and FGF-1 and -4. In addition, anything which does not destroy the TS can be added to the TSs of this invention.

The studies reported herein unexpectedly demonstrate that the inclusion of compounds such as the free base TET or ciprofloxacin (CIP) HCl, in FG or the treatment of FG therewith confers extended longevity to the supplemented FG. This phenomenon can be exploited to increase the duration of a drug's release from the TS. Alternatively, this phenomenon can be exploited to modulate the release of another drug(s) other than the compound used to stabilize the FG, which is (are) also incorporated into the TET-FG, and/or to cause the FG to persist for a greater period in vivo or in vitro.

In general, poorly water soluble forms of a drug, such as the free base of TET, increase the delivery of the drug from the TS more than freely water soluble forms thereof. Therefore, the drug may be bound to an insoluble carrier, such as fibrinogen or activated charcoal, within the TS to prolong the delivery of the drug from the supplemented TS.

In another embodiment, the supplemented TS can be used in organoids and could contain, for example, growth factors such as FGF-1, FGF-2, FGF-4 and OP-1.

In another embodiment, this invention provides a composition that promotes the localized delivery of a poorly water soluble form of an antibiotic(s), such as the free base form of TET, and other drug(s), comprising a TS and an effective concentration of at least one poorly water soluble form of an antibiotic. Similar delivery methods are also applied to other drugs, antibodies, oligonucleotides, cytotoxins, cell proliferation inhibitors, osteogenic or cartilage inducing compounds, growth factors or other supplements herein disclosed.

The present invention has several advantages over the previously used TS compositions and methods. The first advantage is that the growth factor-and/or drug-supplemented TSs of the present invention have many of the characteristics of an ideal biodegradable carrier, namely: they can be formulated to contain only human proteins thus eliminating or minimizing immunogenicity problems and foreign-body reactions; their administration is versatile; and their removal from the host's tissues is not required because they are degraded by the host's own natural fibrinolytic system.

A second advantage is that the present invention provides a good way to effectively deliver growth factors and/or drugs for a prolonged period of time to an internal or external wound. It appears that some growth factor receptors must be occupied for at least 12 hours to produce a maximal biological effect. Previously, there was no way to do this. The present invention allows for prolonged contact between the growth factor and its receptors to occur, and thus allows for the production of strong biological effects.

A third advantage of the present invention is that animal cells can migrate into and through, and grow in the TSs of the present invention. This aids engraftment of the cells to neighboring tissues and prostheses. Based on the composition of the TSs which are available in Europe, it is expected that this is not possible with these formulations. Instead, animal cells must migrate around or digest commercially available TS. Since the importation into the U.S. of commercially available TSs from Europe is illegal (their use in the USA has not been approved by the U.S. FDA).

A fourth advantage is that because of its initial liquid nature, the TS of the present invention can cover surfaces more thoroughly and completely than many previously available delivery systems. This is especially important for the use of the present invention in coating biomaterials and in the endothelialization of vascular prostheses because the growth factor-supplemented FG will coat the interior, exterior and pores of the vascular prosthesis. As a result of this, plus the ability of endothelial cells to migrate into and through the TS, engraftment of autologous endothelial cells will occur along the whole length of the vascular prosthesis, thereby decreasing its thrombogenicity and antigenicity. With previously used TSs, engraftment started at the ends of the vascular prosthesis and proceeded, if at all, into the interior of the same, thus allowing a longer period for thrombogenicity and antigenicity to develop. Previously used TSs for vascular prostheses also primarily were seeded with nonautologous cells which could be rejected by the body and could be easily washed off by the shearing force of blood passing through the prosthesis.

A fifth advantage is that the supplemented and unsupplemented TS of this invention can be molded and thus can be custom made into almost any desired shape. For example, TS such as FG can be supplemented with BMPs and/or DBM and can be custom made into the needed shape to most appropriately treat a bone wound. This cannot be done with DBM powder alone because DBM powder will not maintain its shape.

A sixth advantage is that the AB-supplemented FG of this invention, such as TET-FG, has unexpectedly increased the longevity and stability of the FG compared to that of the unsupplemented FG. This increased stability continues even after appreciable quantities of the AB are no longer remaining in the FG. For example, soaking a newly formed FG clot in a saturated solution of TET produced from free base TET, or in a solution of CIP HCl, produces a FG clot which is stable and preserved even after substantially all the TET or CIP has left the FG clot. While not wishing to be bound by any theory as to how this effect is produced, it is believed that the AB, such as TET or CIP, inhibits plasminogen which is in the TFC and breaks down the FG. Once the plasminogen is inhibited, its continued inhibition does not appear to depend on appreciable quantities of the TET or CIP remaining in the FG. As a result of this stabilizing effect, one can expect an increased storage shelf life of the TS, and possibly an increased persistence in vivo.

The seventh advantage of the present invention is a direct result of the prolonged longevity and stability of the TS. As a result of this unexpected increase in stability of the TS, AB-supplemented FG can be used to produce localized, long term delivery of a drug(s) and/or a growth factor(s). This delivery will continue even after the stabilizing drug, such as TET or CIP, has substantially left the TS. Inclusion of a solid form, preferably a poorly water soluble form of a drug such as free base, into a TS that has been stabilized by, for example, TET or CIP, then allows the stabilized TS to deliver that drug (or growth factor) locally for an extended period of time. Some forms of drugs, such as free base TET, allow for both stabilization of the TS and for prolonged drug delivery. Other drugs may do one or the other but not both. A compound used for the stabilization of a TS to produce prolonged, localized drug delivery is not previously known in the art.

An eighth advantage of the present invention is that it allows site-directed angiogenesis to occur in vivo. While others have demonstrated localized non-specific angiogenesis, supra, no one else has used a TS to promote site-directed angiogenesis.

A ninth advantage of the present invention is that because the components of the TS can be formulated into several forms of simple to use, fast-acting field dressings, it is now possible to control bleeding from hemorrhaging trauma wounds, thereby saving numerous lives that previously would have been lost. Although life-saving methods of treating such wounds are possible by trained medical personal or in fully-equipped clinics and hospitals, the present invention satisfies society's long-felt need for an easy-to-use, first-aid (or even self-applied) treatment that will, in emergency or disaster situations, allow an untrained indi-

Figure 1A:
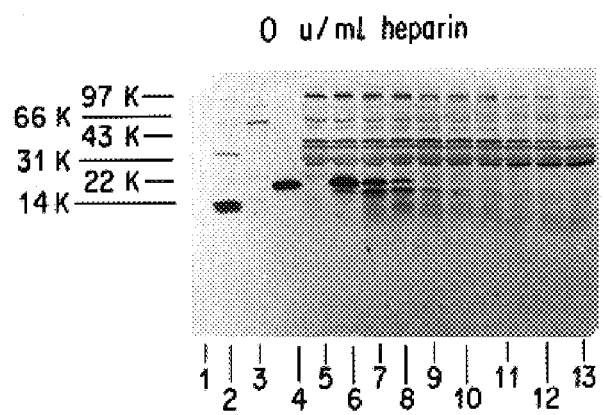
FIGS. 1A–1F show Western blots of gels on which samples containing HBGF-1β had been incubated with 250 U/ml thrombin in the presence of increasing concentrations of heparin. Solutions containing HBGF-1β (10 µg/ml), thrombin (250 µg/ml), and increasing concentrations of heparin (0, 0.5, 5, 10, 20, and 50 units/ml) were incubated at 37° C. for 72 hours. Aliquots were periodically removed from each of the incubating mixtures and were loaded onto 8% SDS polyacrylamide gels that were prepared and run as described by Laemmli (*Nature* 22 7:680 (1970)). The gel was then electroblotted onto nitrocellulose and the band corresponding to HBGF-1β was identified using an affinity-purified polyclonal rabbit antiserum to HBGF-1β.
Figure 1B:
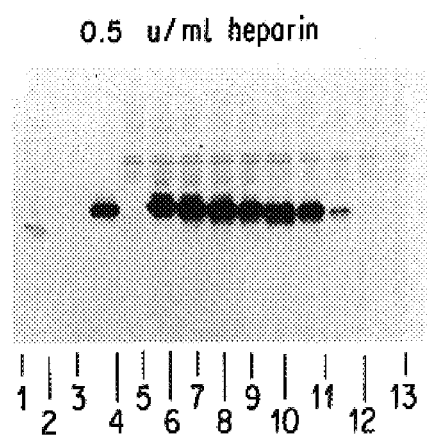
Figure 1C:
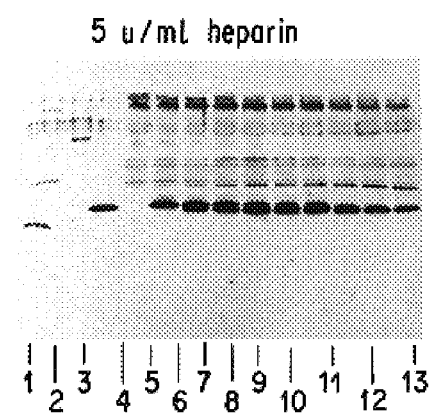
Figure 1D:
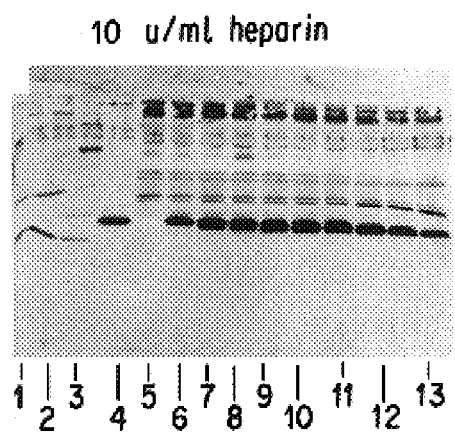
Figure 1E:
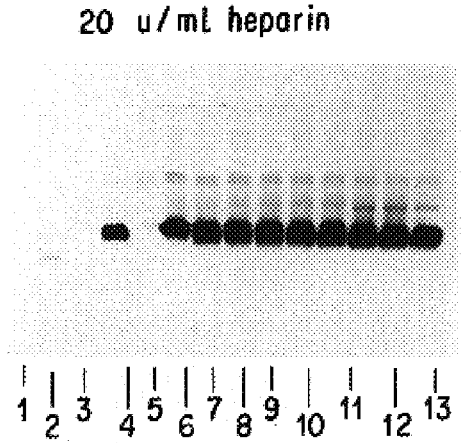
Figure 1F:
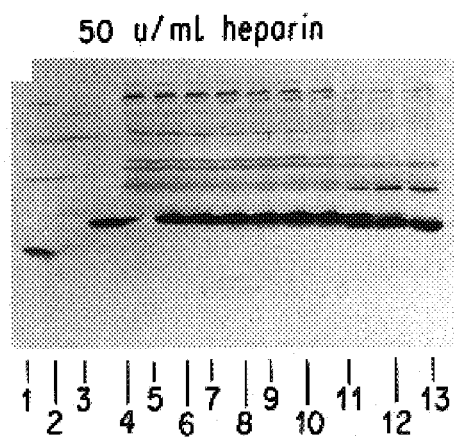

The concentrations of heparin in the incubating mixtures were: panel A) 0 units/ml (u/ml); panel B) 0.5 u/ml; Panel C) 5 u/ml; panel D) 10 u/ml; panel E) 20 u/ml; and panel F) 50 u/ml. In the gels pictured in each of panels A-F, each lane contains the following: lane 1 contains SDS-PAGE low molecular weight standards; lane 2 contains biotinylated standards; lane 3 contains 10 µg/ml HBGF-1β; lane 4 contains 250 u/ml thrombin; and lanes 5–13 contain samples removed from the incubating mixtures at times 0, 1, 2, 4, 6, 8, 24, 48, and 72 hours.

FIG. 2 Graph showing the incorporation of $^3$H-thymidine as a function of relative HBGF-1β concentration. Samples of the HBGF-1β were incubated, as described in FIG. 1 and Example 2, in the presence of 250 U/ml thrombin and 5 U/ml heparin for 0, 24 or 72 hours. Dilutions of these samples were then added to NIH 3T3 cells, which were plated as described in Example 3. CPM is plotted v. HBGF-1β concentration.

Figure 3:
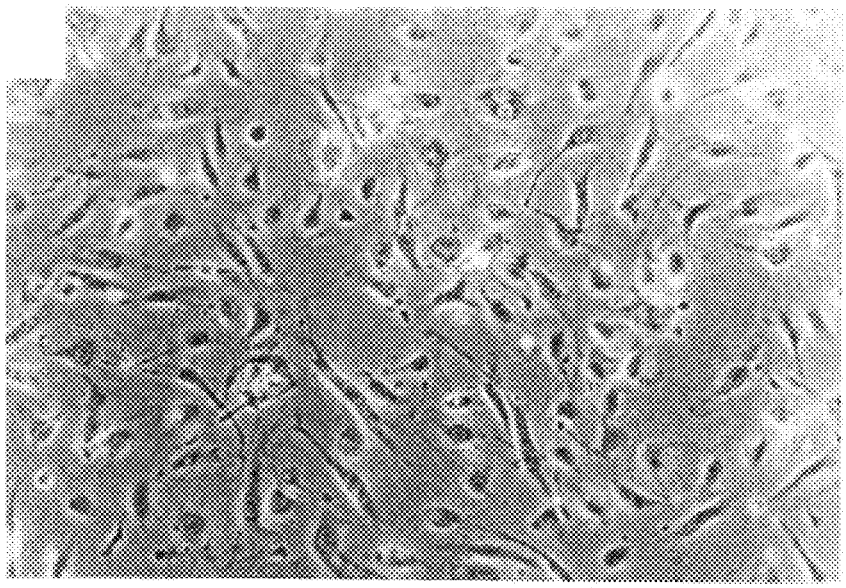

FIG. 3. Photograph showing the typical pattern of human umbilical vein endothelial cells after 7 days' growth on FG supplemented with 100 ng/ml of active, wild-type FGF-1. Note the large number of cells and their elongated shape. Compare with the paucity of cells grown on unsupplemented FG (FIG. 5).

Figure 4:
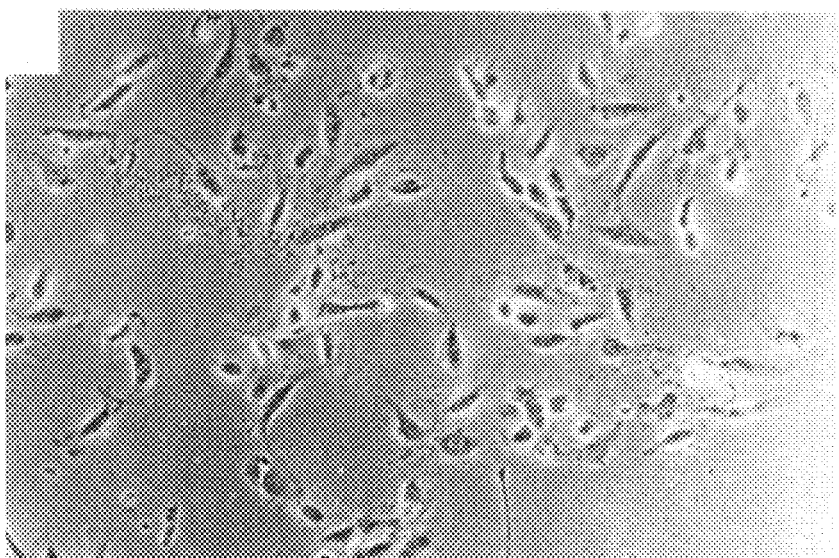

FIG. 4. Photograph showing the typical pattern of human umbilical vein endothelial cells after 7 days' growth on FG supplemented with 10 ng/ml of active, wild-type FGF-1. Note the large number of cells and their elongated shape. Compare with the paucity of cells grown on unsupplemented FG (FIG. 5).

Figure 5:
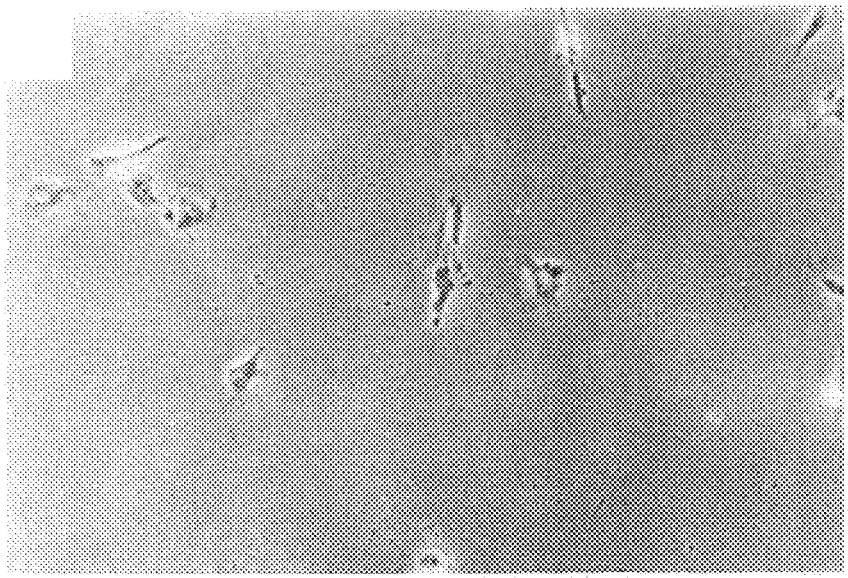

FIG. 5. Photograph showing the typical pattern of human umbilical vein endothelial cells after 7 days' growth on unsupplemented FG. Note the small number of cells, compared to the number of cells in FIGS. 3 and 4, which indicates a slower proliferation rate.

Figure 6:

FIG. 6. Photograph showing the typical pattern of human umbilical vein endothelial cells after 7 days' growth on FG supplemented with 100 ng/ml of inactive, mutant FGF-1. Note the small number of cells, compared to the number of cells in FIGS. 3 and 4, which indicates a slower proliferation rate.

Figure 7:
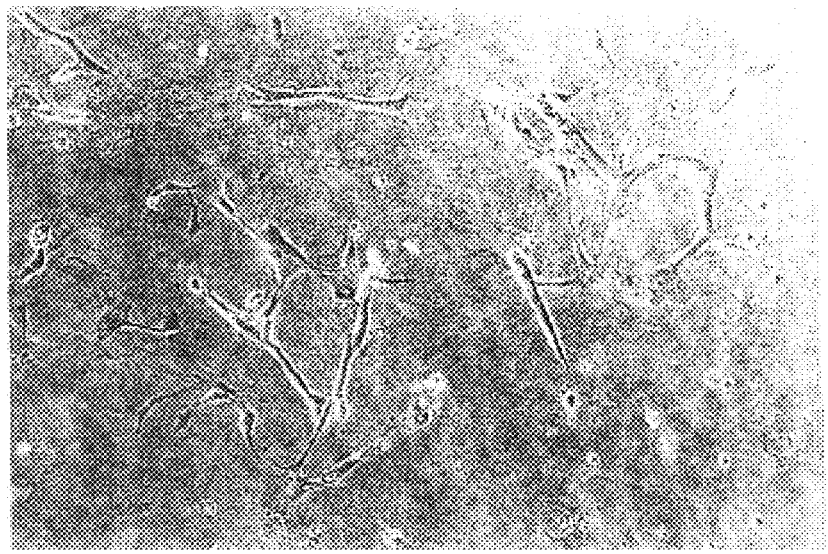

FIG. 7. Photograph showing the typical pattern of human umbilical endothelial cells 24 hours after having been embedded in FG at a concentration of $10^5$ cells per ml of FG. The protein and thrombin concentrations of the FG were 4 mg/ml and 0.6 NIH units/ml, respectively. Note, their elongated, multipodial morphology and that they formed a cellular network where they came in contact with each other. Compare with the cobblestone shape of similar cells grown in fibronectin (FIG. 9.)

Figure 8:

FIG. 8. Photograph showing the typical pattern of human umbilical endothelial cells 48 hours after having been embedded in FG at a concentration of $10^5$ cells per ml of FG. The culture conditions were as described in FIG. 7. Note the further accentuated, elongated and multipodial morphology and increasing development of cellular networks. Compare with the cobblestone shaped cells grown in fibronectin (FIG. 10) and note the lack of a cellular network in the latter.

Figure 9:
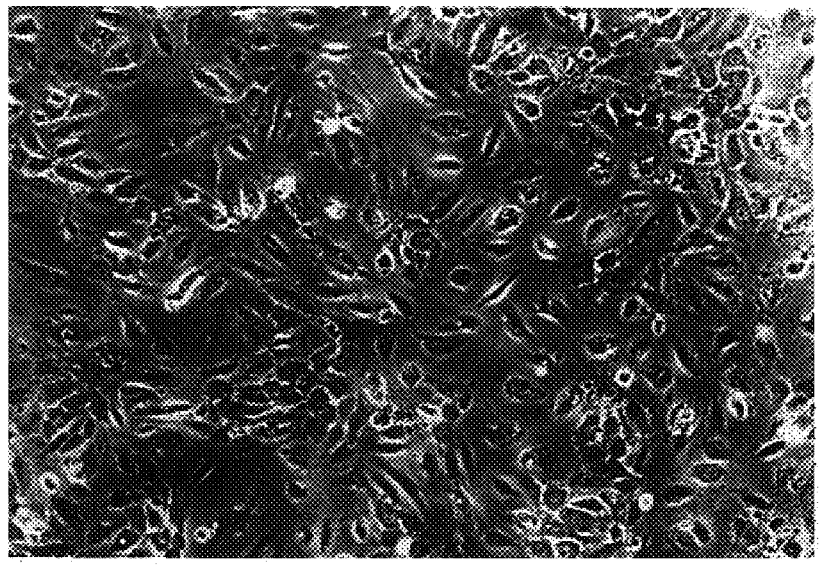

FIG. 9. Photograph showing the typical pattern of human umbilical endothelial cells 24 hours after having been cultured on a surface coated with fibronectin. Note the cobblestone shape of the cells and the lack of cellular networks. Compare to FIG. 7.

Figure 10:
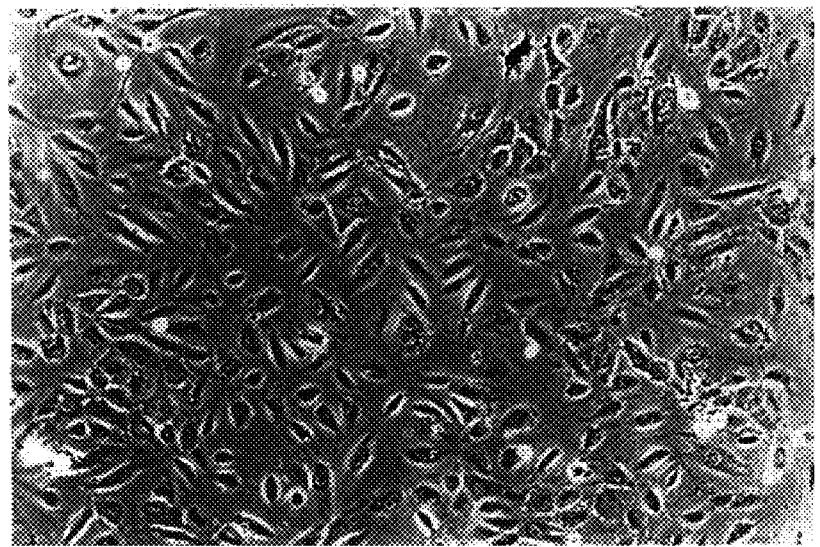

FIG. 10. Photograph showing the typical pattern of human umbilical endothelial cells 48 hours after having been cultured in a commonly used film of fibronectin. Note the cobblestone shape of the cells and the lack of cellular networks. Compare to FIG. 8.

FIG. 11. Micrographs of cross sections of PTFE vascular grafts that were explanted from dogs after 7 days (panels A, C, E) or 28 days (panels B, D, F). Prior to implantation, the grafts were either untreated (A and B), coated with FG alone (C and D), or coated with FG supplemented with heparin and HBGF-1 (E and F).

Untreated controls (A & B) showed minimal mesenchymal tissue ingrowth, with both their interstices filled with, and their luminal surfaces coated with fibrin coagulum. The FG-treated grafts showed mesenchymal tissue ingrowth in only the outer half of the grafts' interstices, with the rest being filled with fibrin coagulum. Very few interstitial capillaries were present. In contrast, the grafts treated with FG containing FGF-1 showed more abundant interstitial ingrowth and by 28 days showed numerous capillaries, myofibroblasts and macrophages, with inner capsules consisting of several layers of myofibroblasts beneath confluent endothelial cell layers. Results of similar grafts after 128 days of implantation were similar, with greater numbers of capillaries in the FG+FGF-1 group (data not shown).

FIG. 12. Scanning electron micrographs of the inner lining of the vascular grafts described in FIG. 11 after 28 days of implantation. The grafts were either untreated (G), coated with FG alone (H), or coated with FG supplemented with heparin and HBGF-1 (I). Untreated control grafts (G) showed sparse areas of endothelial cell coverage amidst areas of thrombus containing red blood cells, platelets, and areas of exposed PTFE graft material (visible in the center and top of the picture). Grafts coated with FG alone (H) showed islands of endothelial cells amidst areas of fibrin coagulum. In contrast, grafts treated with FG+HBGF-1 (I) showed confluent endothelial cells oriented along the direction of blood flow.

Figure 13:
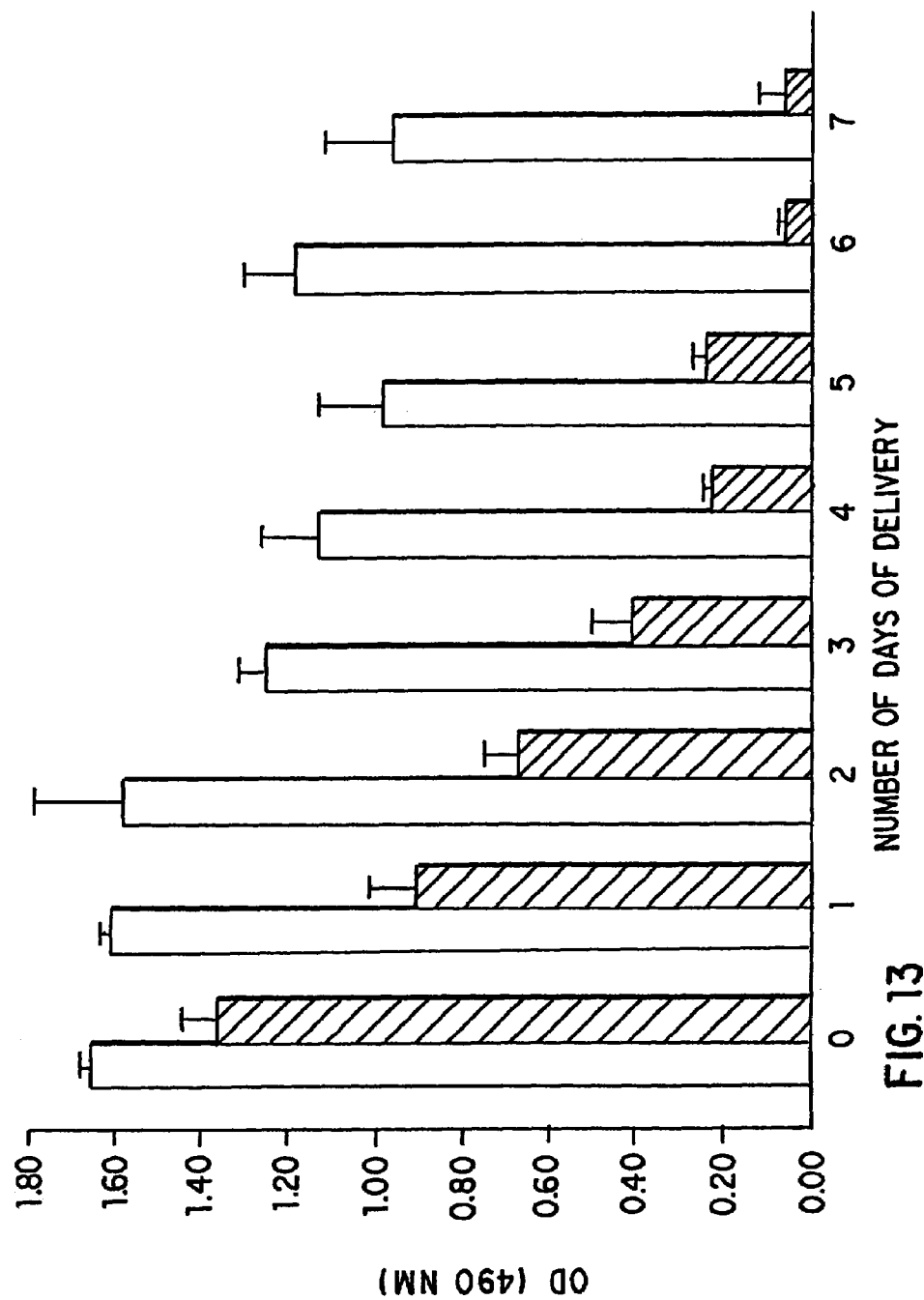

FIG. 13. Graph showing the inhibition of smooth muscle cell proliferation by the release of tributyrin from supplemented fibrin sealant. Unsupplemented fibrin sealant=(□); tributyrin-supplemented fibrin sealant=(cross-hatched).

Figure 14:
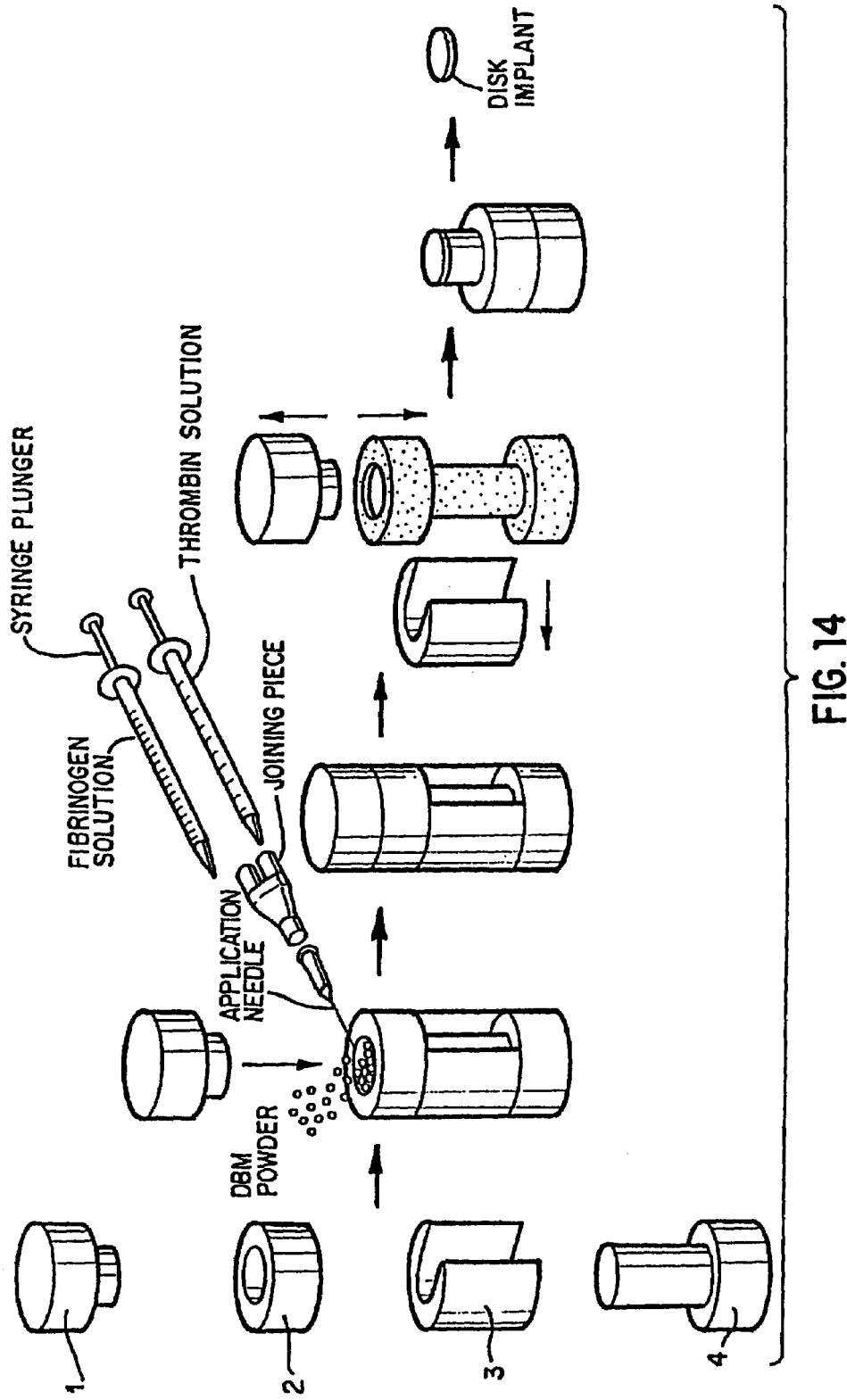

FIG. 14. Diagram showing the preparation of disc-shaped implants 1 mm thick and 8 mm in diameter prepared using an aluminum mold.

Figure 15:
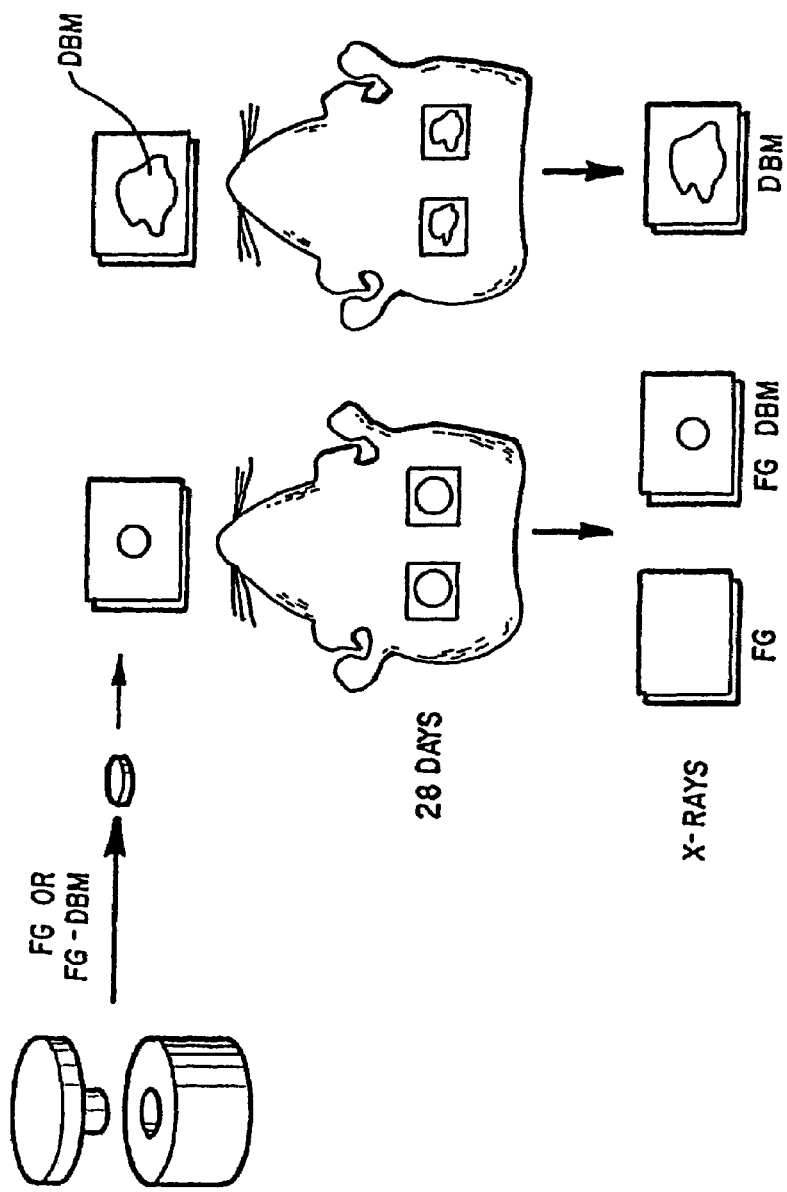

FIG. 15. Diagram illustrating intramuscular bioassay for the induction of bone formation in rats by DBM alone, by FG implants or by DBM-FG.

Figure 16:
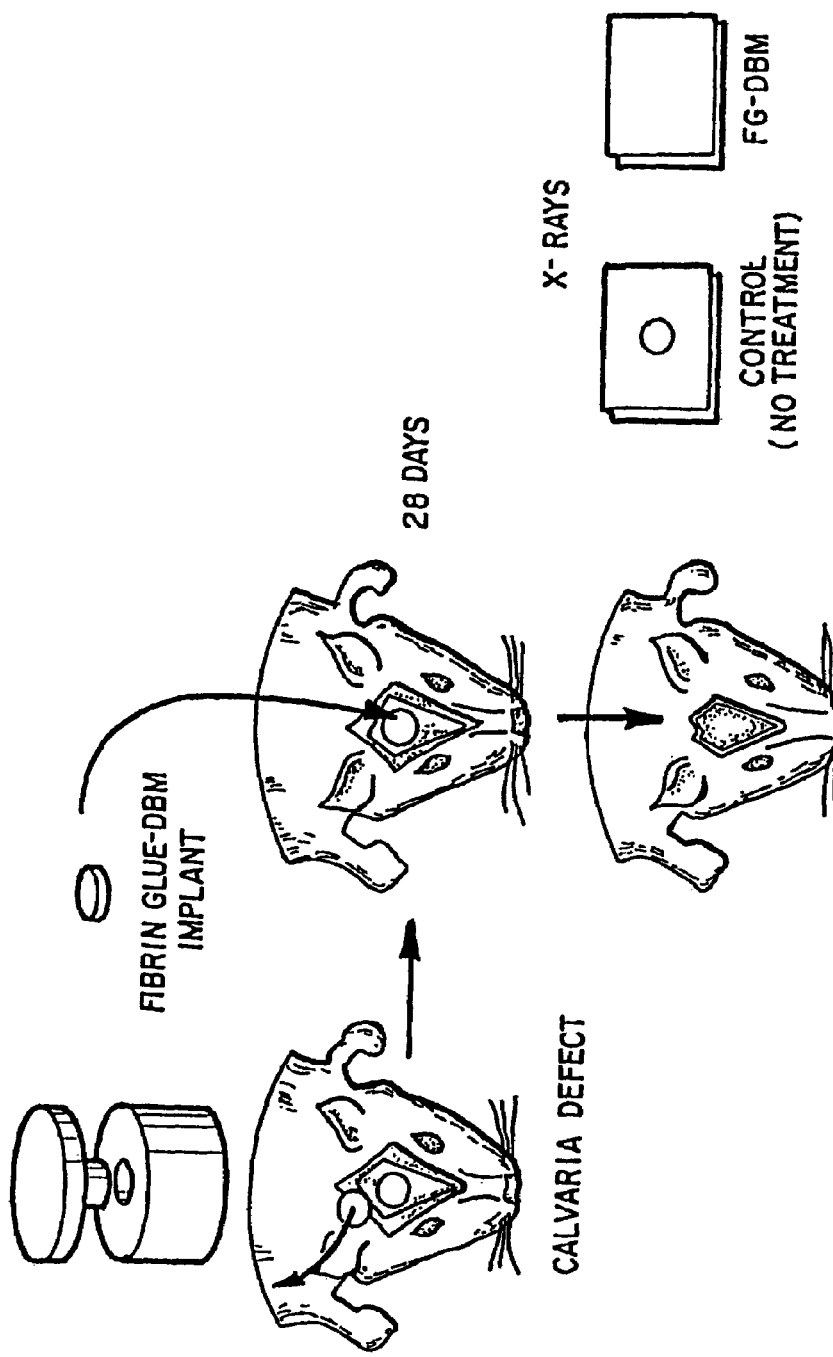

FIG. 16. Diagram illustrating the induction of bone formation in calvarial implants by DBM-FG.

Figure 17:
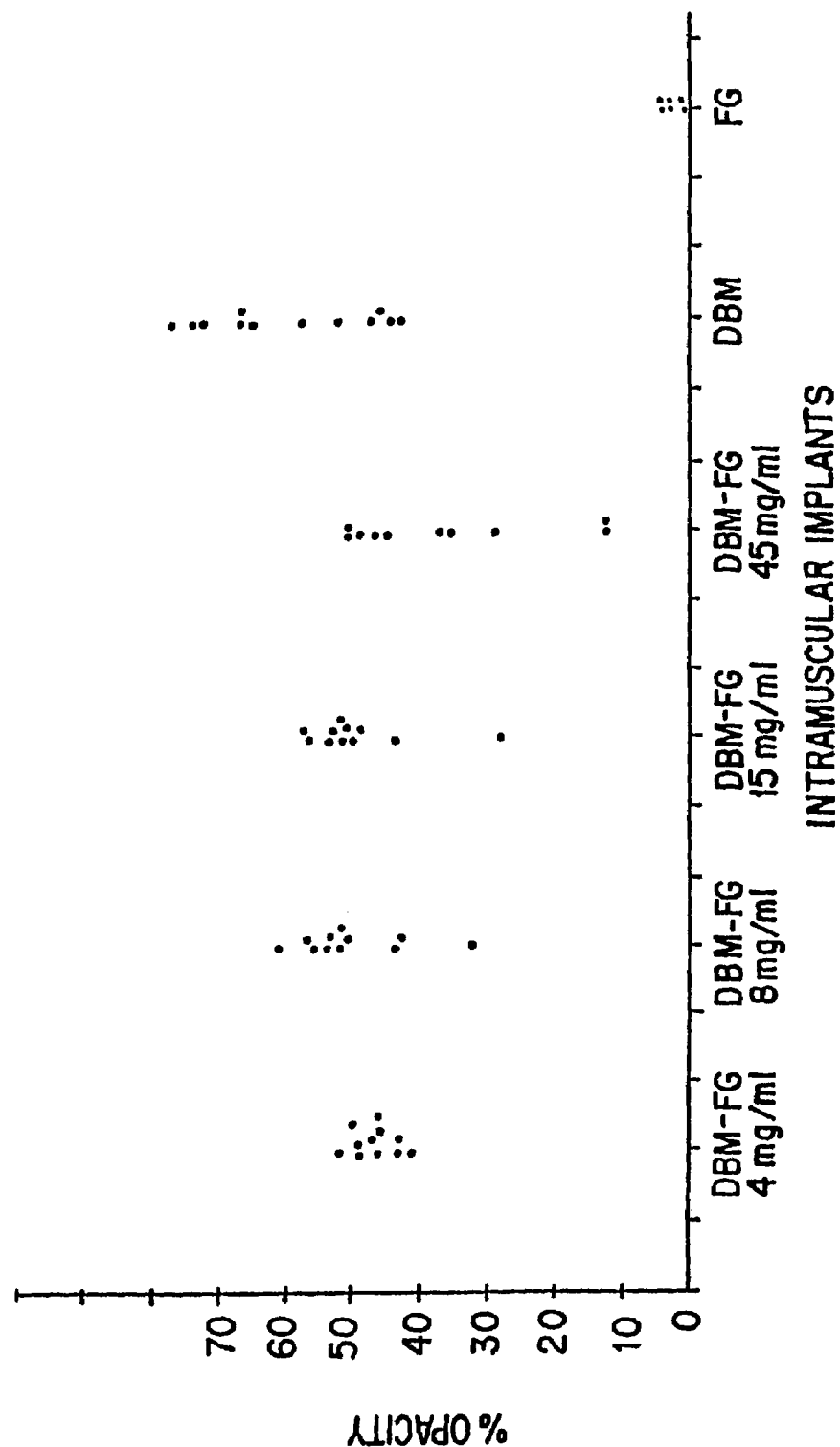

FIG. 17. Graph showing the radio-opacity data at 28 days postoperative from intramuscular implants of DBM-FG, DBM or FG.

Figure 18:
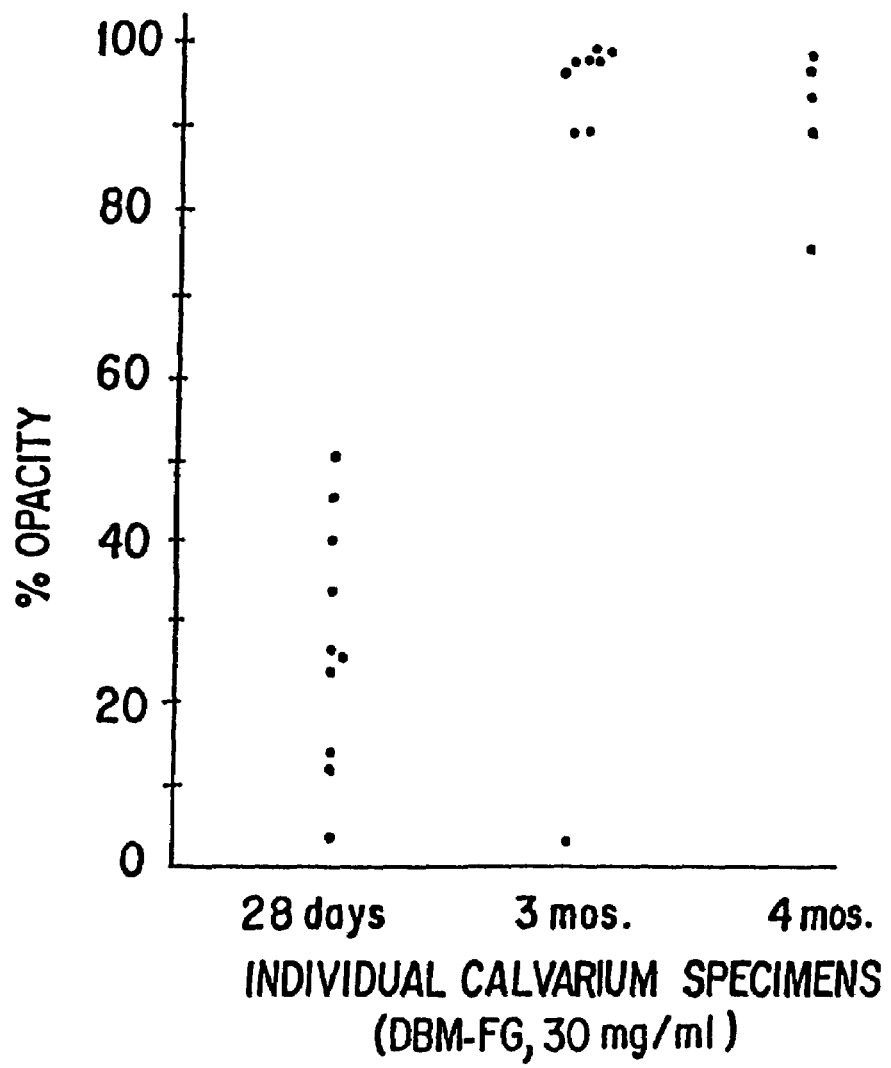

FIG. 18. Graph showing the radio-opacity data from DBM-FG (30 mg/ml) calvarial implants at 28 days, 3 months and 4 months postoperative.

Figure 19A:
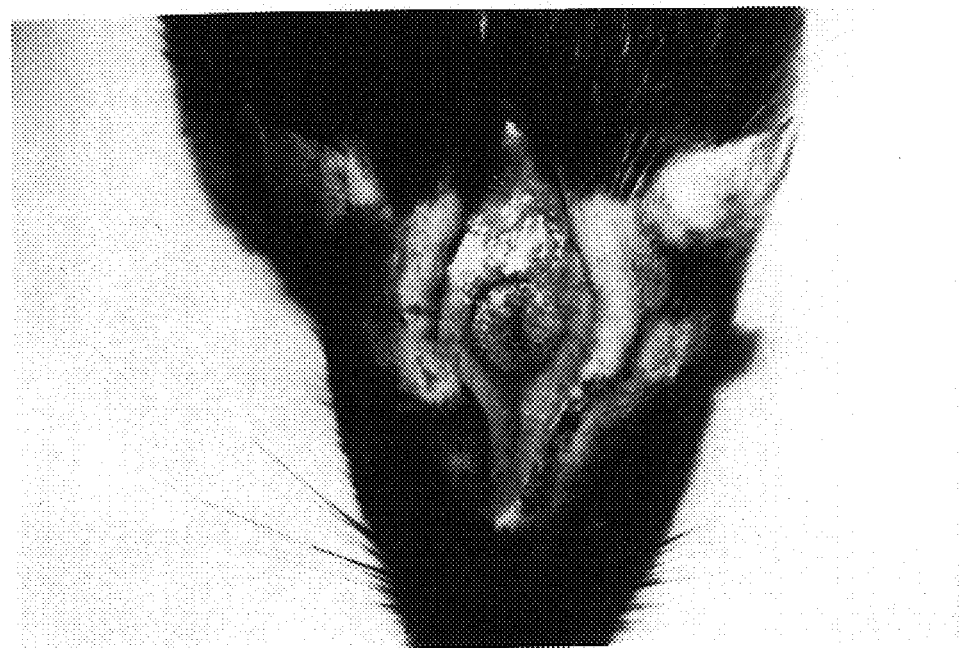
Figure 19B:
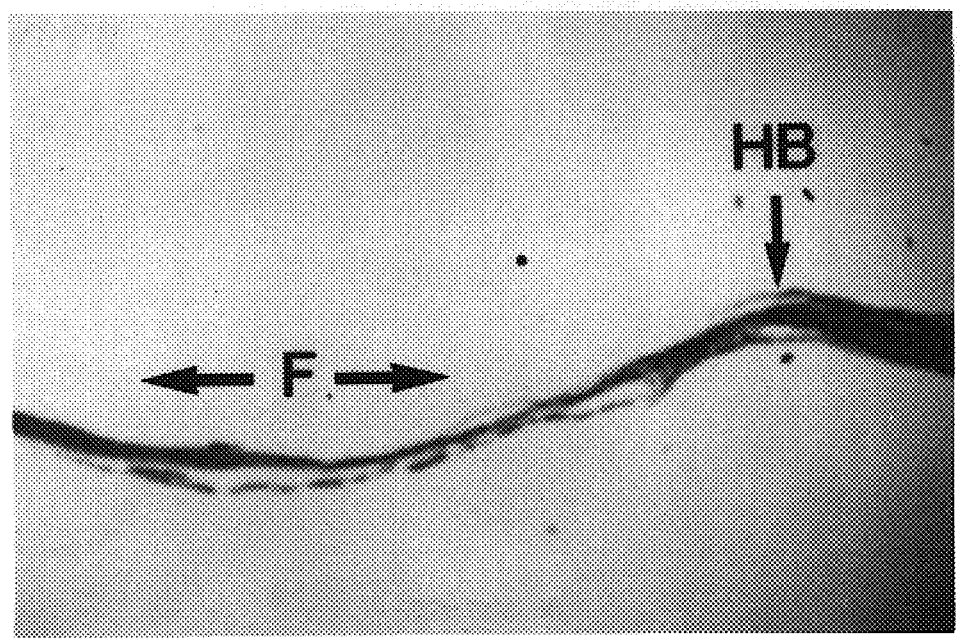

FIG. 19. FIG. 19A is a photograph of a craniotomy site at 28 days post surgery in a treated animal. FIG. 19B is a photograph of the calvarial wound from an untreated control at 28 days postoperative. Note that only fibrous connective tissue has developed across the craniotomy wound.

Figure 20:
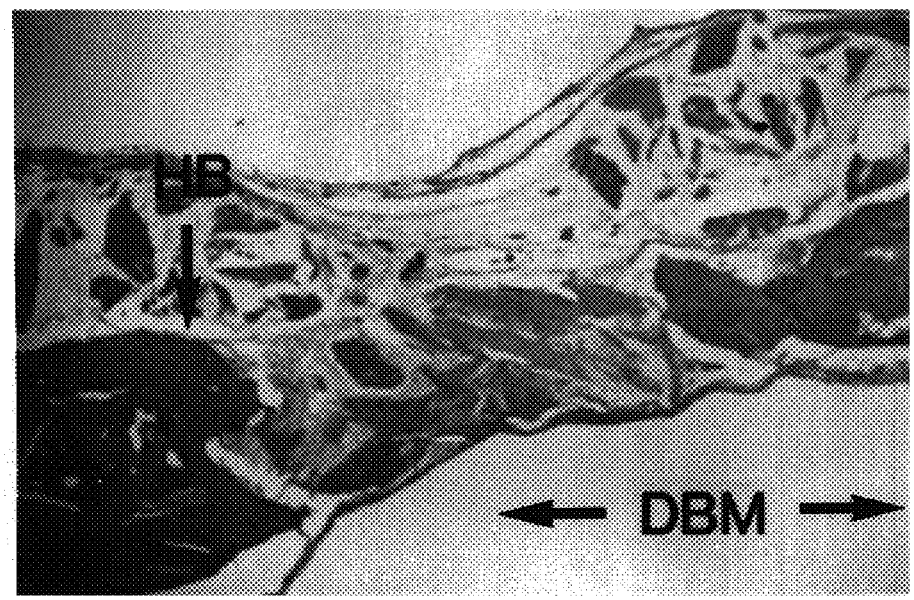

FIG. 20. Photograph from the craniotomy wounds of animals which were treated with DBM particles only.

Figure 21:
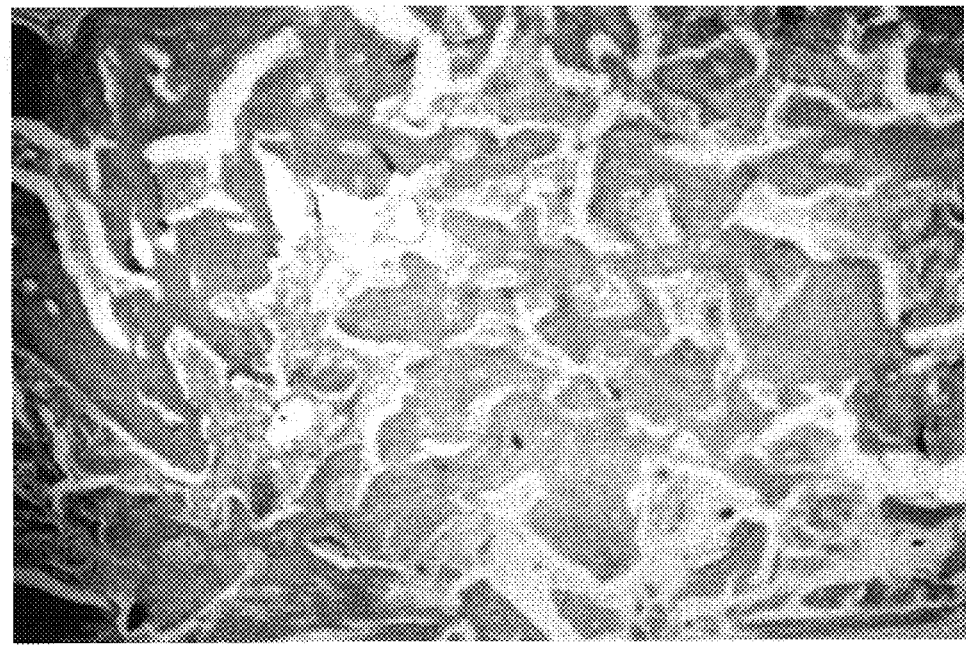

FIG. 21. Photograph of new bone formed in the craniotomy site in response to DBM-FG (15 mg/ml).

Figure 22:
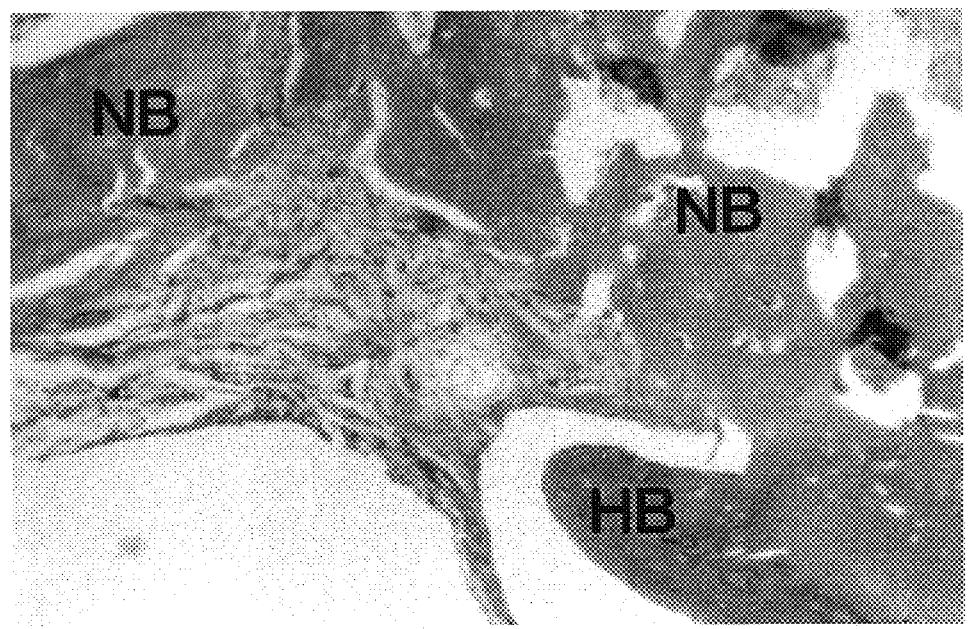

FIG. 22. Photograph of new bone formed in the craniotomy site in response to DBM-FG (15 mg/ml). Note that typically more bone marrow formed in craniotomy wounds that had been implanted with DBM-FG disks than with DBM implants alone.

Figure 23:
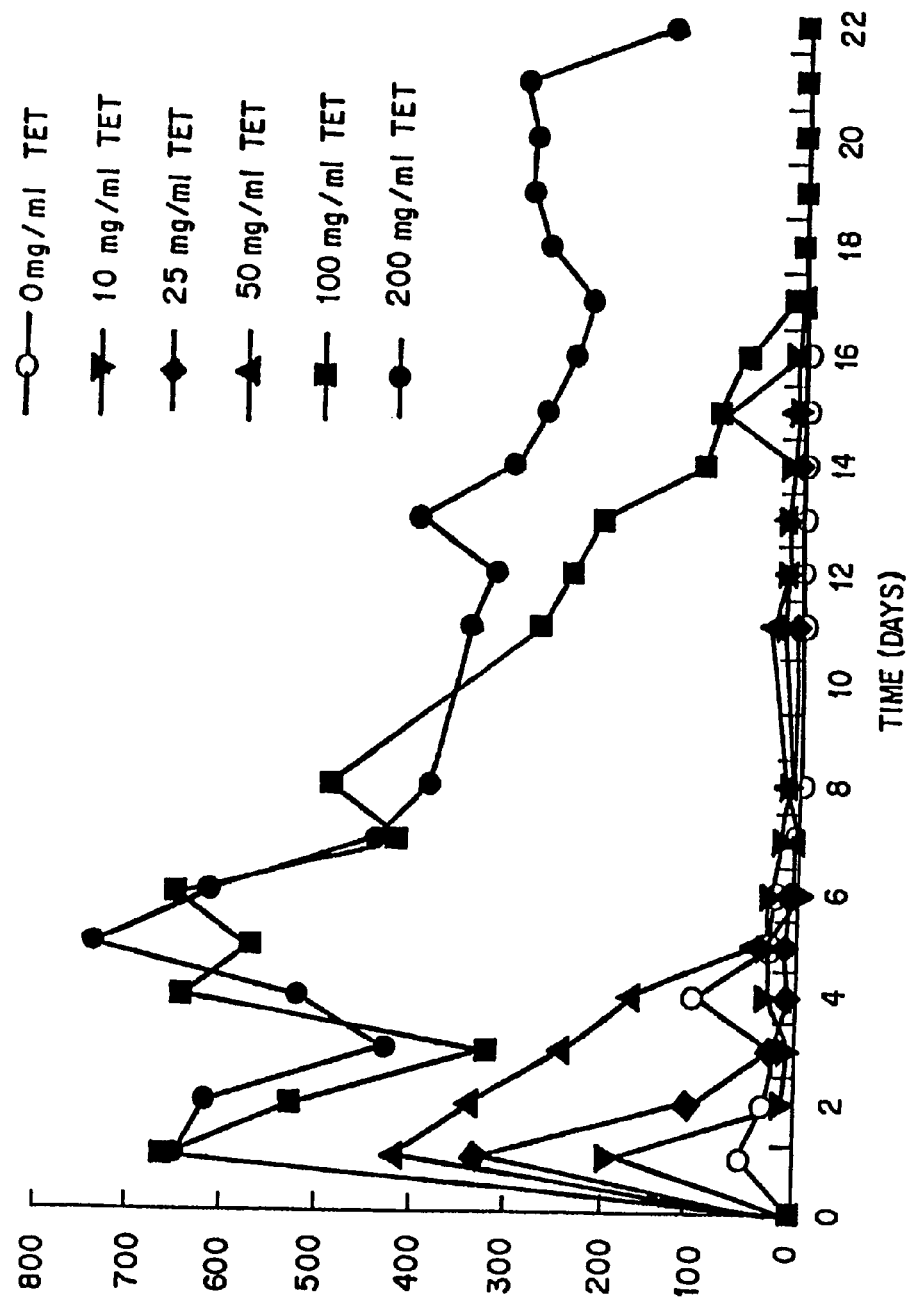

FIG. 23. Graph showing the release of TET from 3×6 mm diameter disks of FG at 37° C. The concentration of the released TET was measured spectrophotometrically in 2 ml of PBS supernatant that had been replaced daily. Two of these "static" in vitro experiments were carried out with identical results. The results of one of them is shown here.

Figure 24:
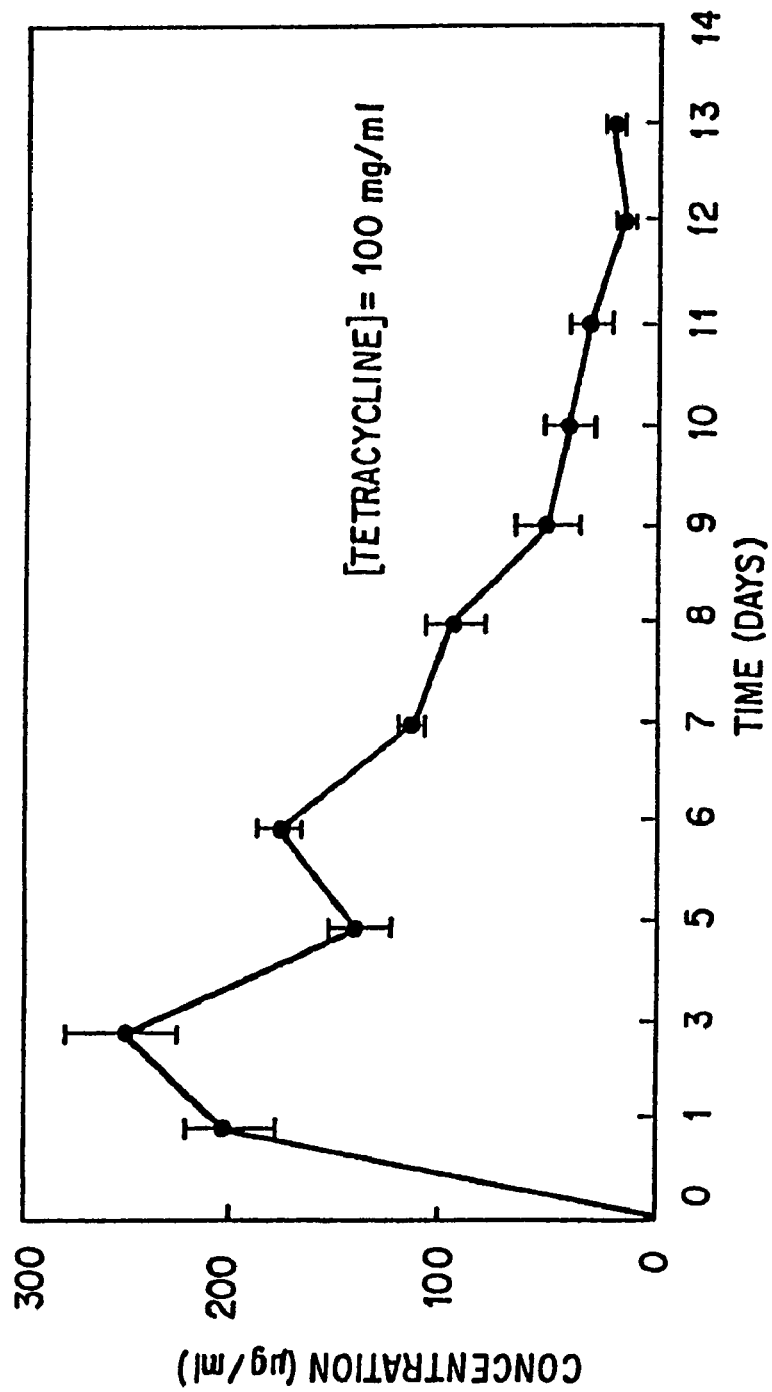

FIG. 24. Graph showing the release of TET from 3×6 mm diameter disks of FG at 37° C. The disks contained 100 mg/ml of TET and were placed in closed vessels filled with 2 ml of PBS. The TET concentration was measured spectrophotometrically in the PBS effluent which had been continuously exchanged at a rate of 3 ml/day. The volume of the PBS supernatant had been kept constant at approximately 2 ml. The data are the average of two experiments.

Figure 25:
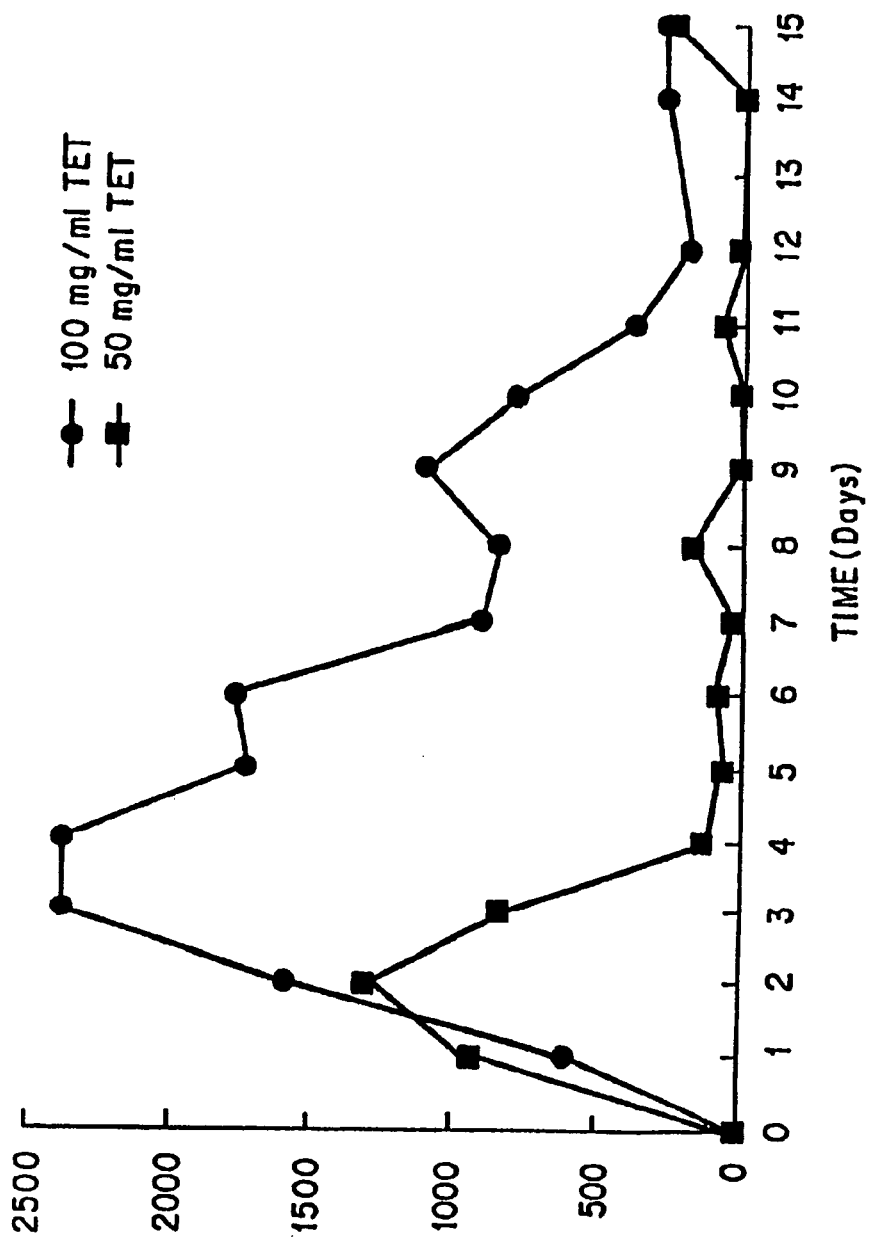

FIG. 25. Graph showing the release of TET into saliva from 3×6 mm diameter disks containing 50 or 100 TET mg/ml FG at 37° C. The TET concentration was measured spectrophotometrically in 0.75 ml of saliva supernatant that had been replaced daily. The saliva used in these experiments had been pooled from ten donors, centrifuged, filtered and kept at 4° C.

Figure 26:
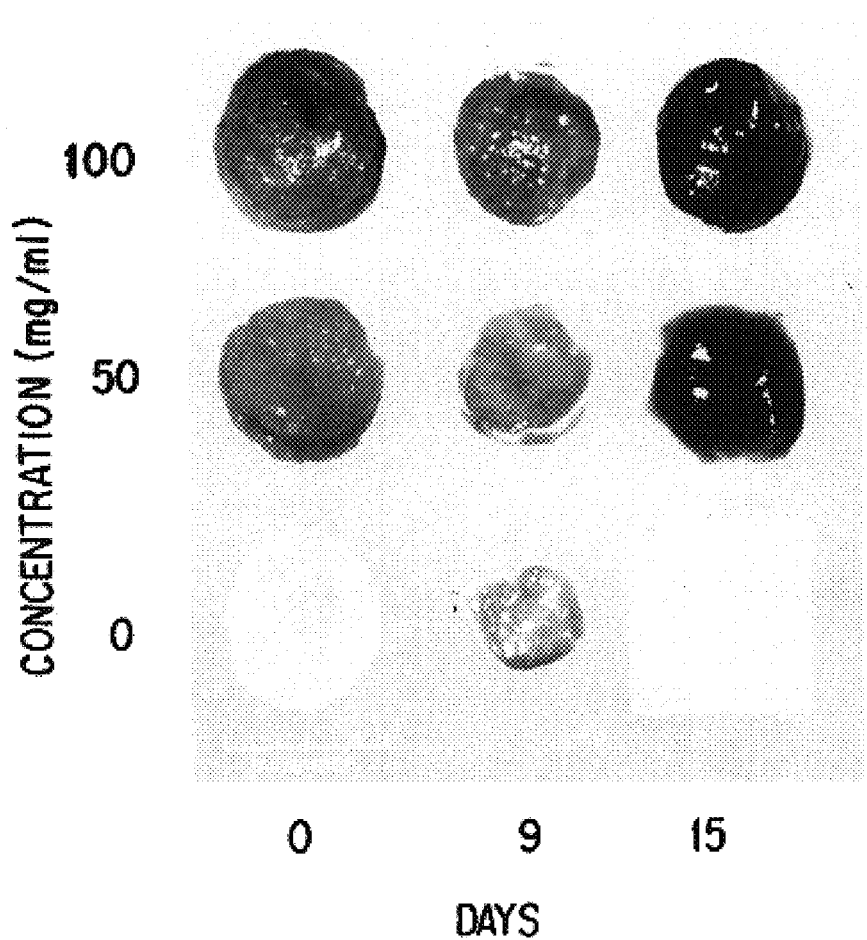

FIG. 26. Photograph showing the stability of TET-supplemented FG was increased compared to that of control FG. Photographs of 3×6 mm diameter FG matrices without TET and with 50 and 100 mg/ml TET over a period of 15 days. The disks had been kept in 0.75 ml of saliva which had been changed daily. The saliva had been pooled from 10 donors. It had then been centrifuged, filtered and stored at 4° C. before use in this experiment. Note that at nine days, the FG matrix which did not contain TET had decayed more than the matrices which contained either 50 or 100 mg/ml of TET Also note that at days, the FG matrix which did not contain TET had almost totally decayed, whereas the FG matrices which contained 50 or 100 mg/ml of TET were almost unchanged. Therefore, the inclusion of 50 or 100 mg/ml of TET dramatically prolonged the longevity of FG matrices in saliva in vitro.

Figure 27:
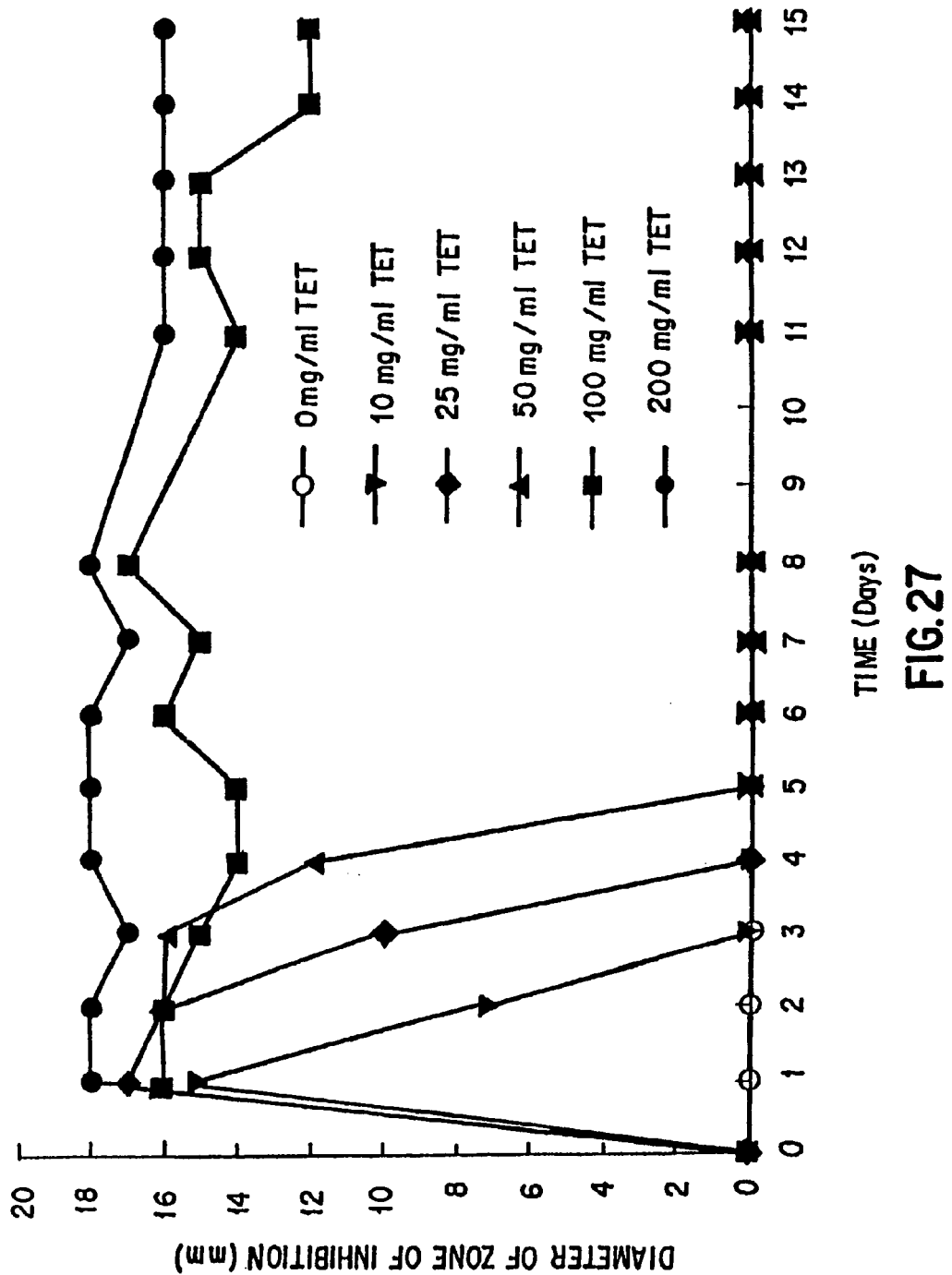

FIG. 27. Graph showing the antibacterial activity of TET released from TET-supplemented FG. Two ml PBS surrounding the 3×6 mm TET-supplemented FG disks was replaced daily. For testing the antimicrobial activity of the released TET, 6 mm paper disks impregnated with the collected eluates were incubated for 18 hours at 37° C. on agar plates containing *E. coli*. Then the diameter of the zone of inhibition was measured.

Figure 28:
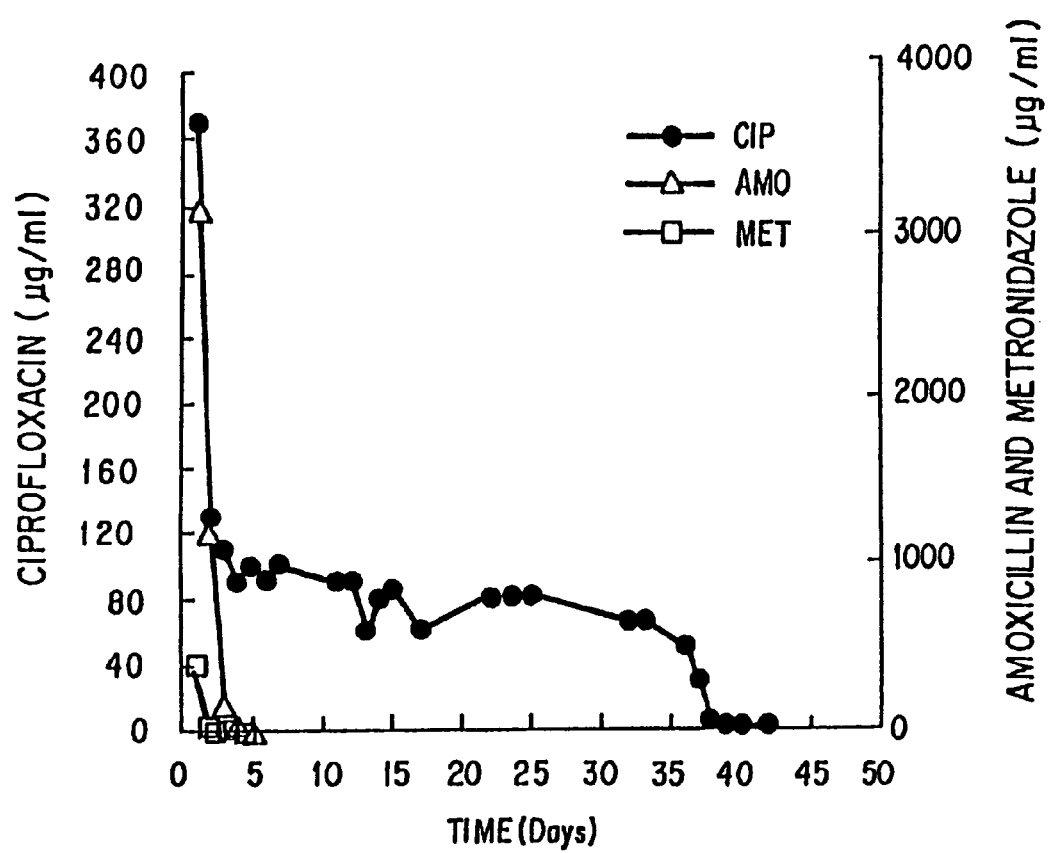

FIG. 28. Graph showing the release of ciprofloxacin, amoxicillin and metronidazole from FG matrices. Individual 3×6 mm diameter disks containing 100 mg/ml of the respective antibiotics were immersed in 2 ml of phosphate-buffered saline at 37° C. The supernatant was replaced daily and the antibiotic concentration was measured spectrophotometrically at 275, 274 and 320 nm, respectively.

Figure 29:
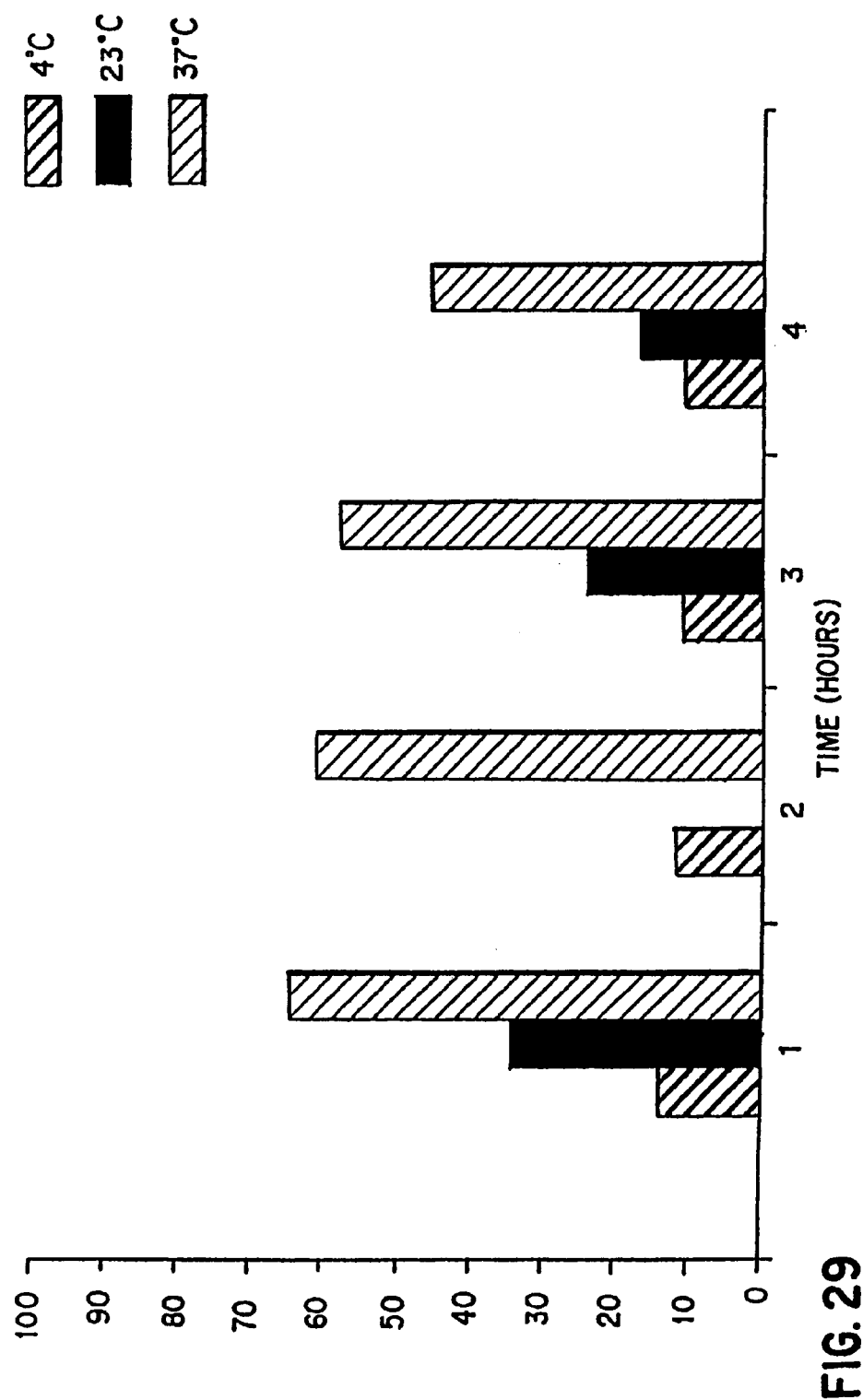

FIG. 29. Graph showing the release of TET from TET-supplemented FG disks was proportional to the temperature of the PBS bathing the TET-FG disks.

Figure 30:
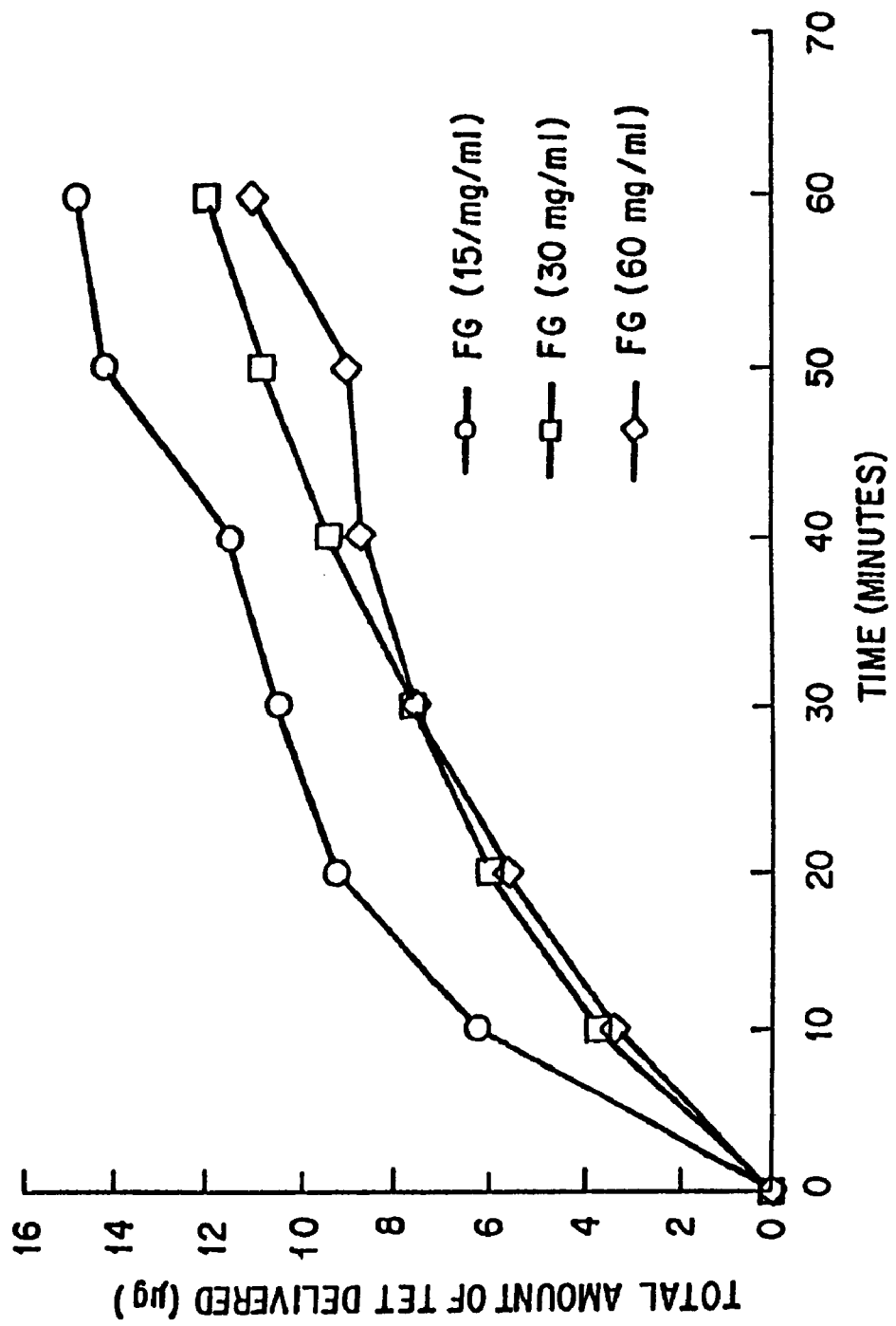

FIG. 30. Graphing showing the effect of FG protein concentration on the release of TET from TET-FG. Note that higher FG protein concentrations resulted in a slower TET release rate from the TET-FG.

Figure 31A:
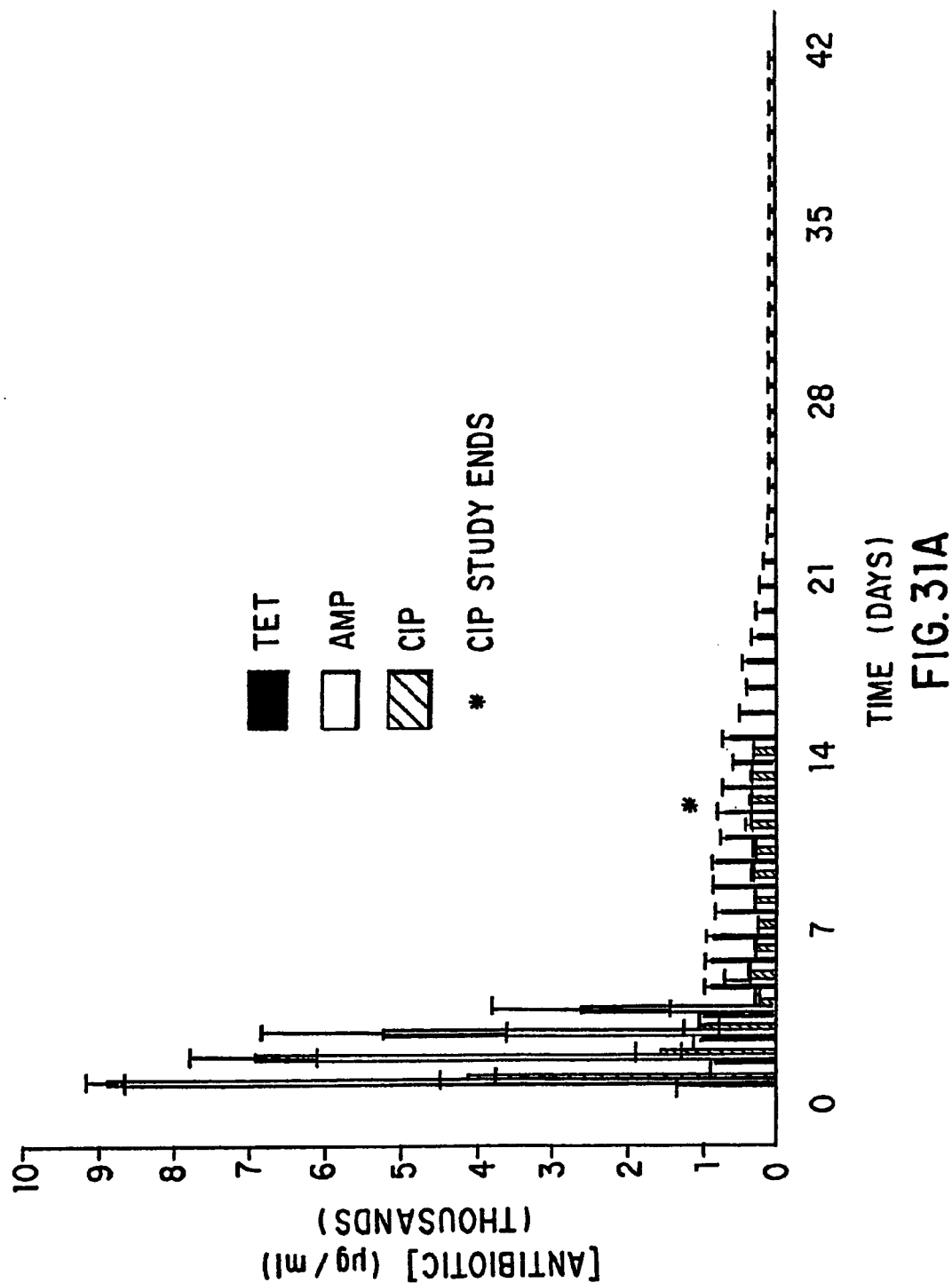

FIG. 31A. Graph showing the elution profile of in vitro release of antibiotic from a supplemented fibrin sealant disks.

Figure 31B:
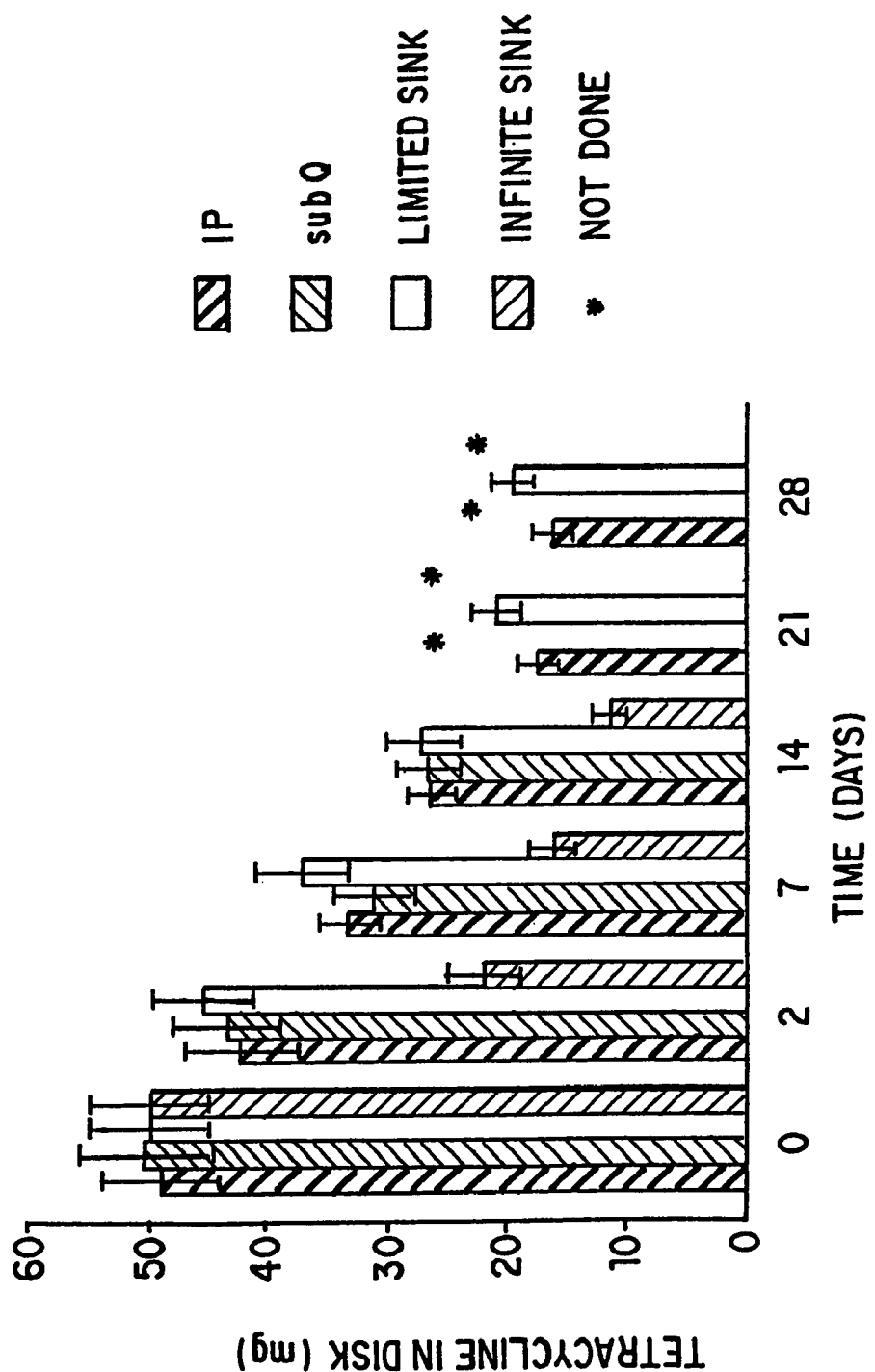

FIG. 31B. Graph showing the elution profile of in vitro vs. in vivo release of tetracycline from supplemented fibrin sealant disks.

Figure 31C:
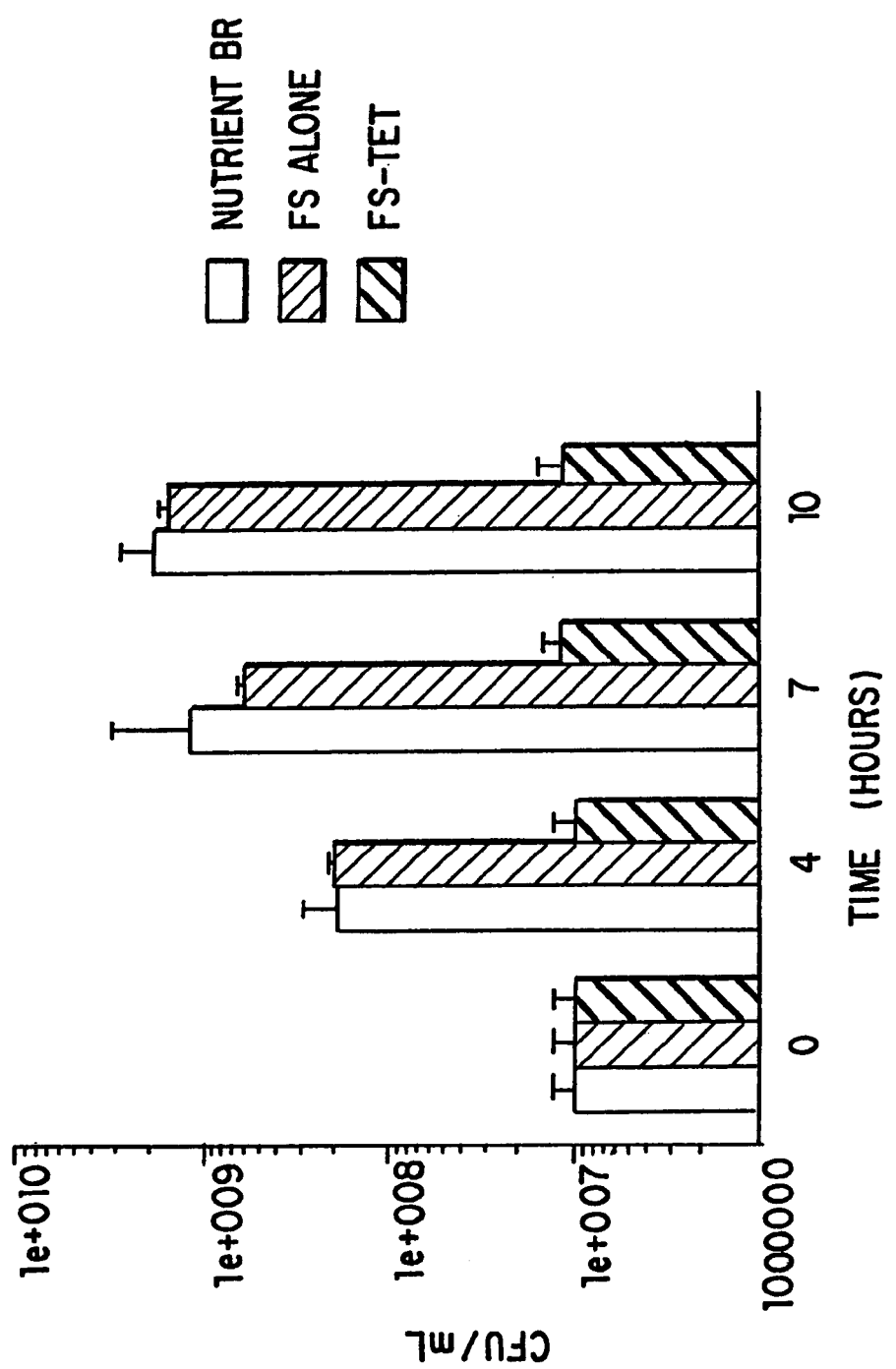

FIG. 31C. Graph showing the inhibition of bacterial growth by tetracycline supplemented fibrin sealant disks as compared to unsupplemented fibrin sealant disks and culture media alone.

Figure 32:
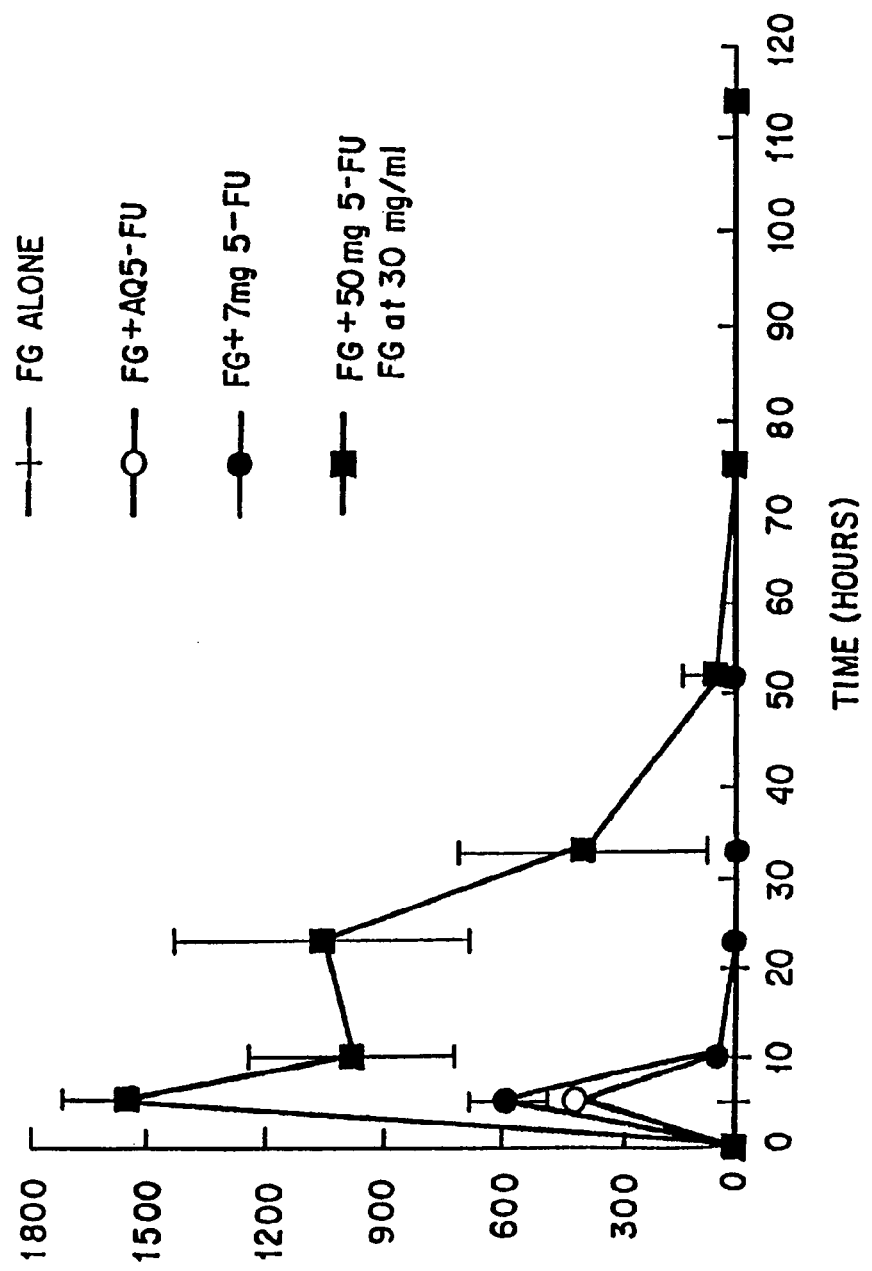

FIG. 32. Graph showing the release of 5-FU from 5-FU-supplemented FG was prolonged by the use of solid forms of 5-FU.

Figure 33:
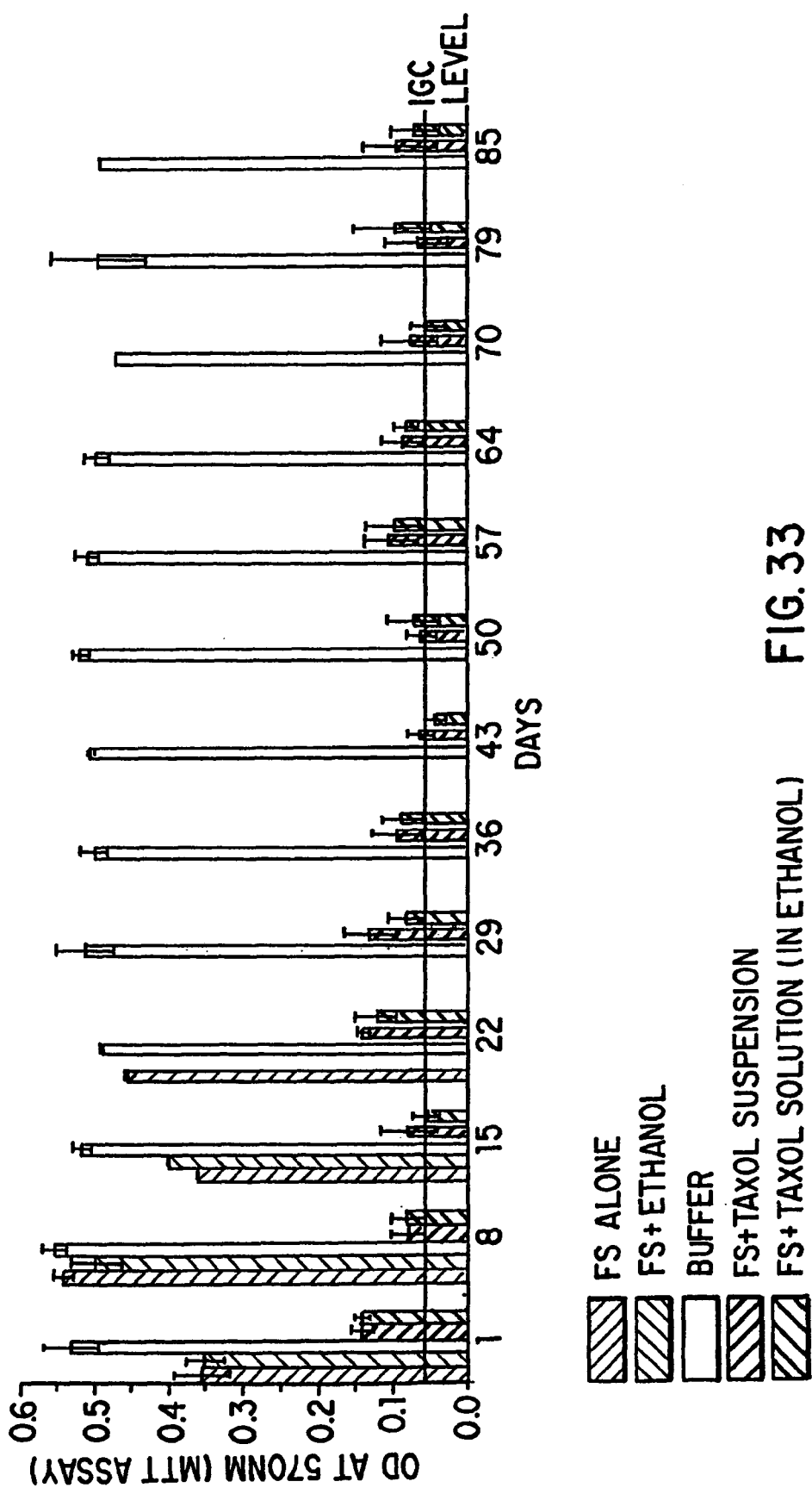

FIG. 33. Graph showing the effect over time of supernatants from taxol-supplemented fibrin sealant composition on rapidly proliferating human ovarian carcinoma cells (OVCAR).

Figure 34:
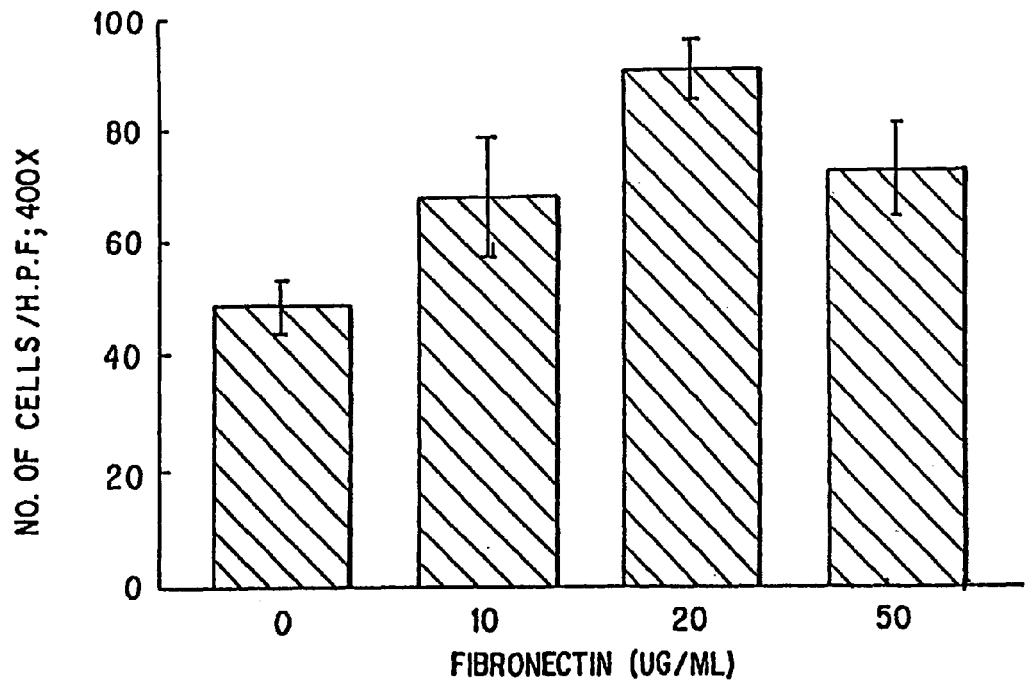

FIG. 34. Graph showing the dose-response relationship of the chemotactic response of NIH 3T3 fibroblasts to Fibronectin. A step gradient of increasing concentrations of Fibronectin was added to the lower wells of the modified Boyden's chambers. The data are expressed as means +/−S.E. of migrated cells per high power field and demonstrate that, as a function of dose, fibronectin induced the chemotaxis of NIH 3T3 cells toward it.

Figure 35:
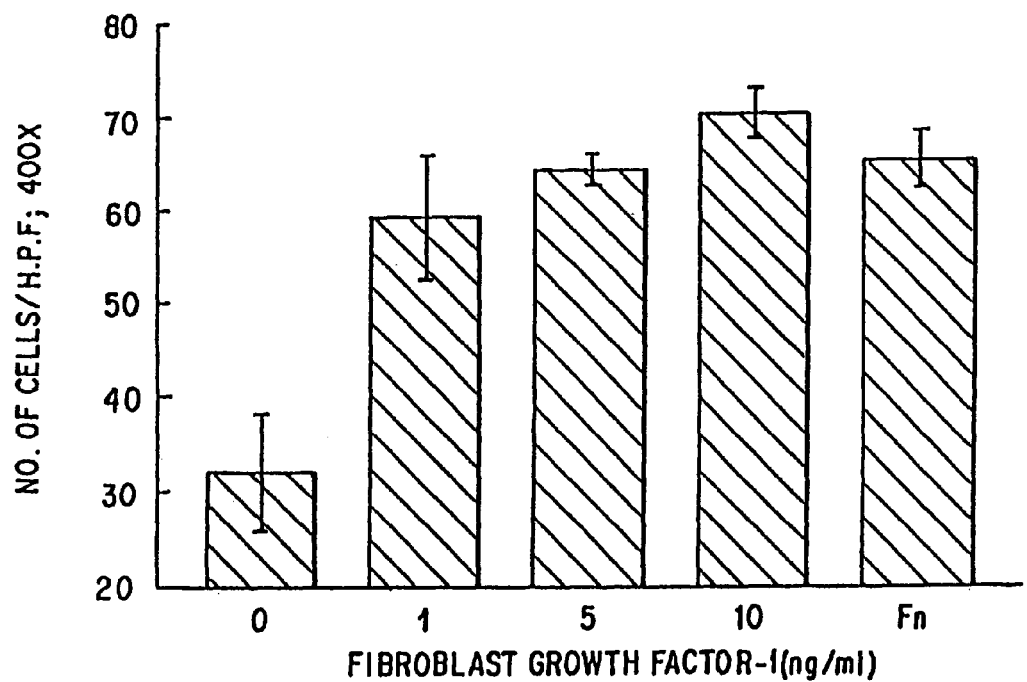

FIG. 35. Graph showing the dose-response relationship of the chemotactic response of NIH 3T3 fibroblasts to FGF-1. A step gradient of increasing concentrations of FGF-1 was added to the lower wells of the modified Boyden's chambers in the presence of heparin. The data are expressed as the means +/−S.E. of migrated cells per high power field and demonstrate that, as a function of dose, FGF-1 induced the chemotaxis of fibroblasts toward it.

Figure 36:
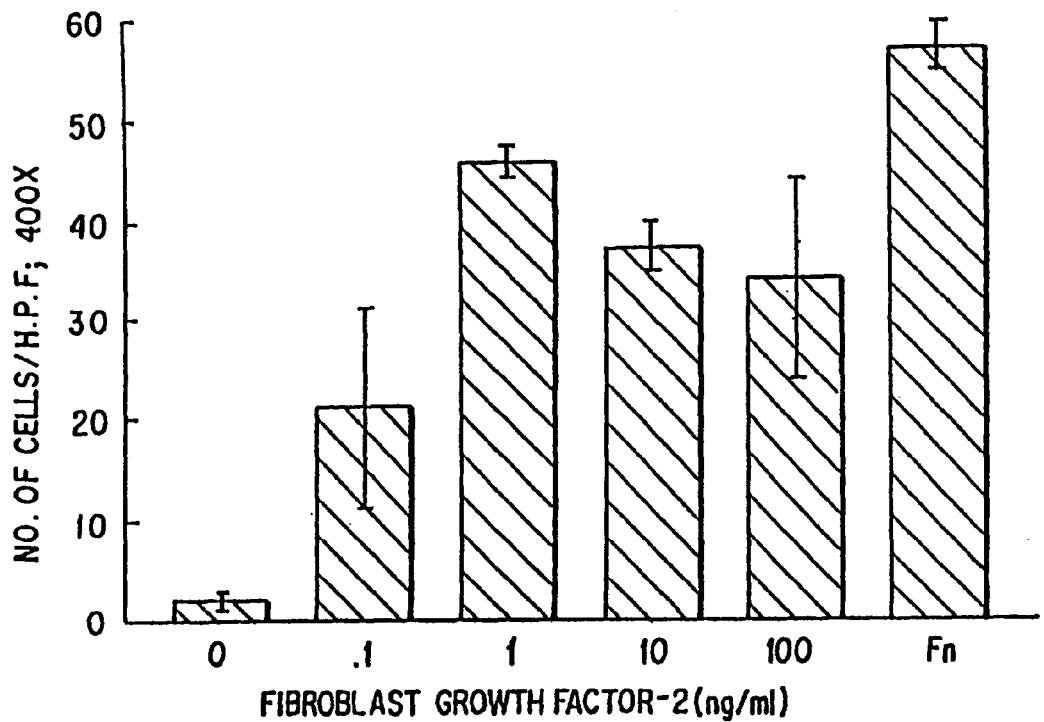

FIG. 36. Graph showing the dose-response relationship of the chemotactic response of NIH 3T3 fibroblasts to FGF-2. A step gradient of increasing concentrations of FGF-2 was added to the lower wells of the modified Boyden's chambers. The data are expressed as the means +/−S.E. of migrated cells per high power field and demonstrate that, as a function of dose, FGF-2 induced the chemotaxis of fibroblasts toward it.

Figure 37:
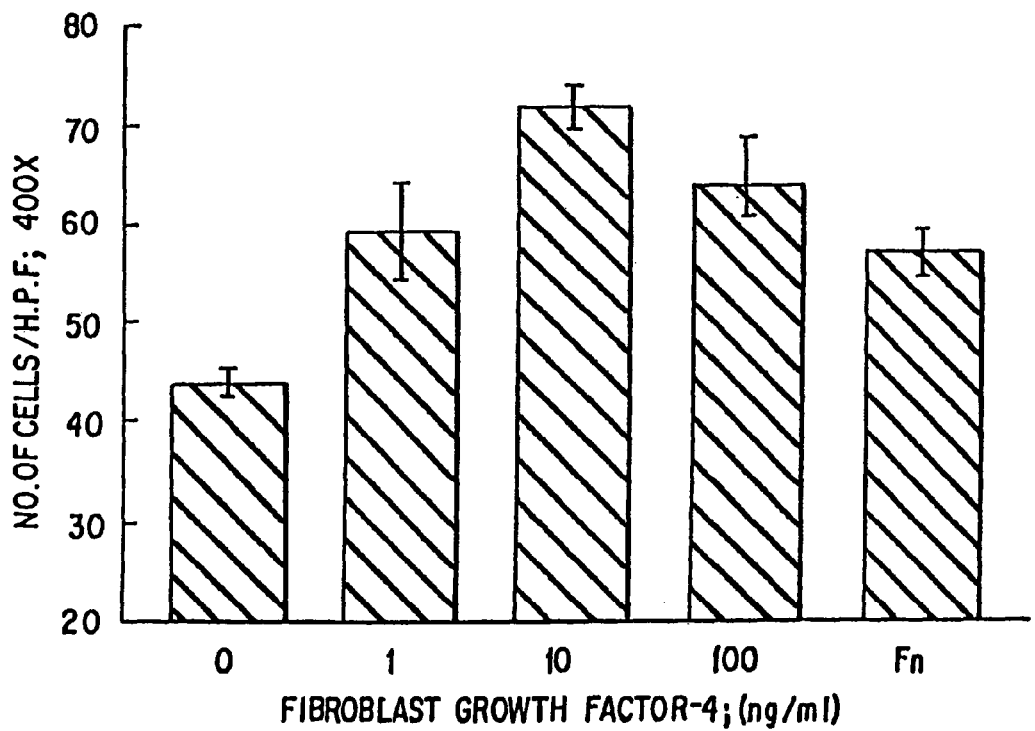

FIG. 37. Graph showing the dose-response relationship of the chemotactic response of NIH 3T3 fibroblasts to FGF-4. A step gradient of increasing concentrations of FGF-4 was added to the lower wells of the modified Boyden's chambers in the presence of heparin. The data are expressed as the means +/−S.E. of migrated cells per high power field and demonstrate that, as a function of dose, FGF-4 induced the chemotaxis of fibroblasts toward it.

Figure 38:
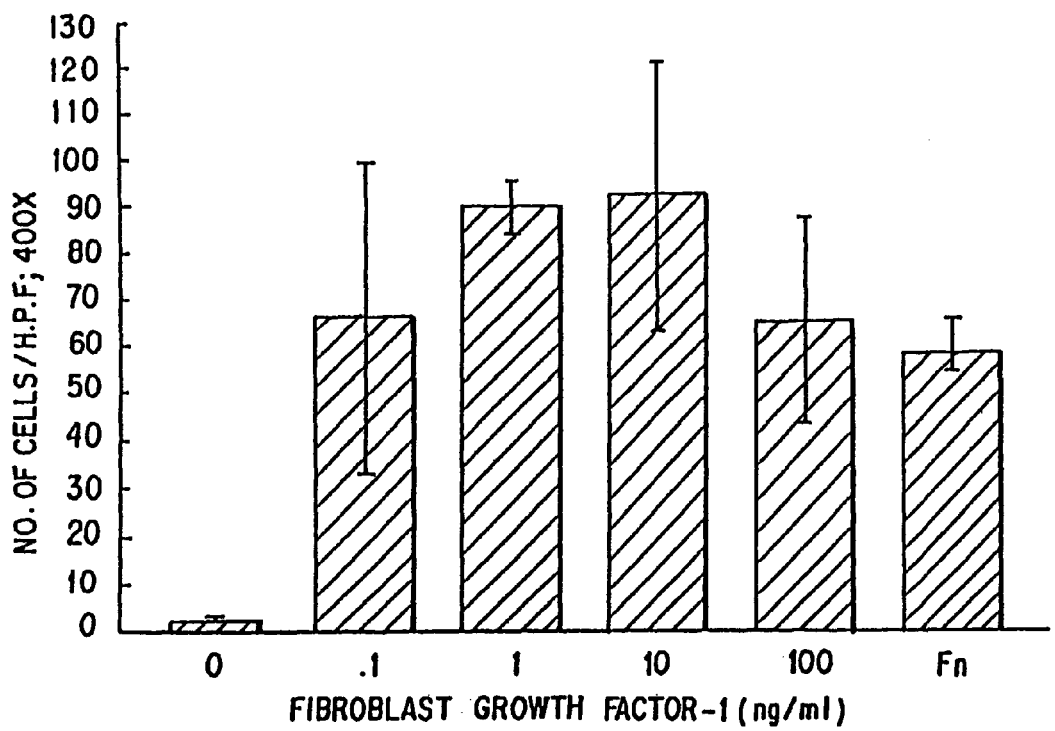

FIG. 38. Graph showing the dose-response relationship of the chemotactic response of human dermal fibroblasts (HDFs) to FGF-1. A step gradient of increasing concentrations of FGF-1 was added to the lower wells of the modified Boyden's chambers in the presence of heparin. The data are expressed as the means +/−S.E. of migrated cells per high power field and demonstrate that, as a function of dose, FGF-1 induced the chemotaxis of HDFs toward it.

Figure 39:
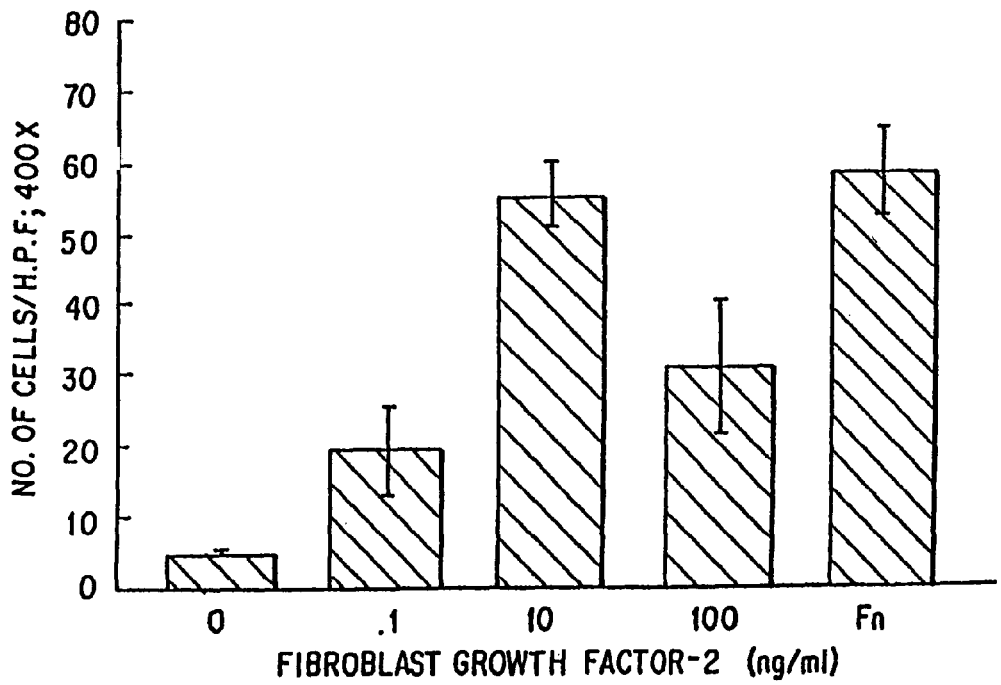

FIG. 39. Graph showing the dose-response relationship of the chemotactic response of HDFs to FGF-2. A step gradient of increasing concentrations of FGF-2 was added to the lower wells of the modified Boyden's chambers. The data are expressed as the means +/−S.E. of migrated cells per high power field and demonstrate that, as a function of dose, FGF-2 induced the chemotaxis of HDFs toward it.

Figure 40:
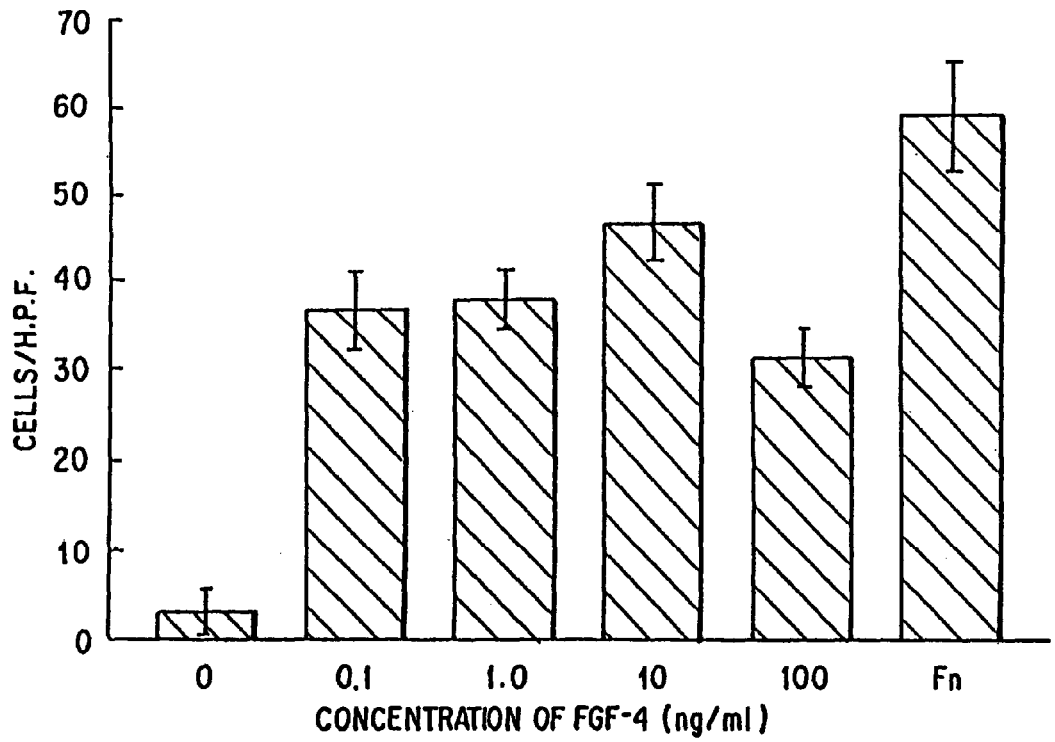

FIG. 40. Graph showing the dose-response relationship of the chemotactic response of HDFs to FGF-4. A step gradient of increasing concentrations of FGF-4 was added to the lower wells of the modified Boyden's chambers. The data are expressed as the means +/−S.E. of migrated cells per high power field and demonstrate that, as a function of dose, FGF-4 induced the chemotaxis of HDFs toward it.

Figure 41:
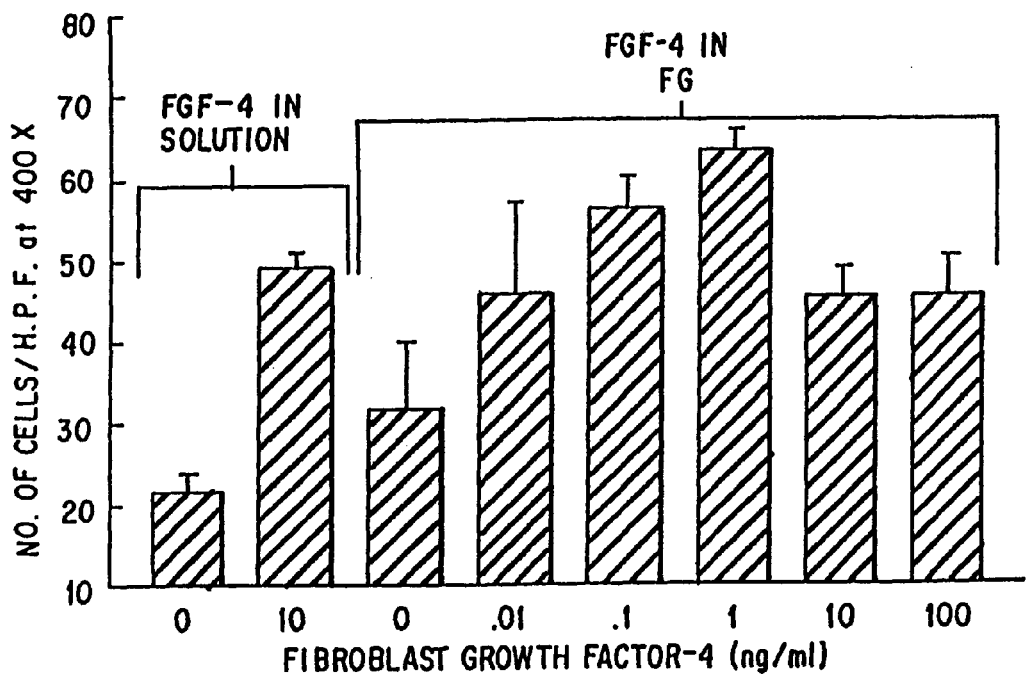

FIG. 41. Graph showing the dose-response relationship of the chemotactic response of HDFs to FGF-4 in solution and in FG. FGF-4 was incorporated into FG and placed in the bottom well of chemotaxis chambers. The amount of FGF in the FG was sufficient to result in the indicated concentrations when evenly distributed throughout the FG and medium in the lower chamber. Negative controls included medium alone and FG without FGF. Medium containing FGF-4 at a concentration of 10 ng/ml in the lower chamber was utilized as a positive control. The data are expressed as the means +/−S.E. of migrated cells per high power field and demonstrate that, as a function of dose, FGF-4 released from FG induced the chemotaxis of HDFs toward the FG.

Figure 42:
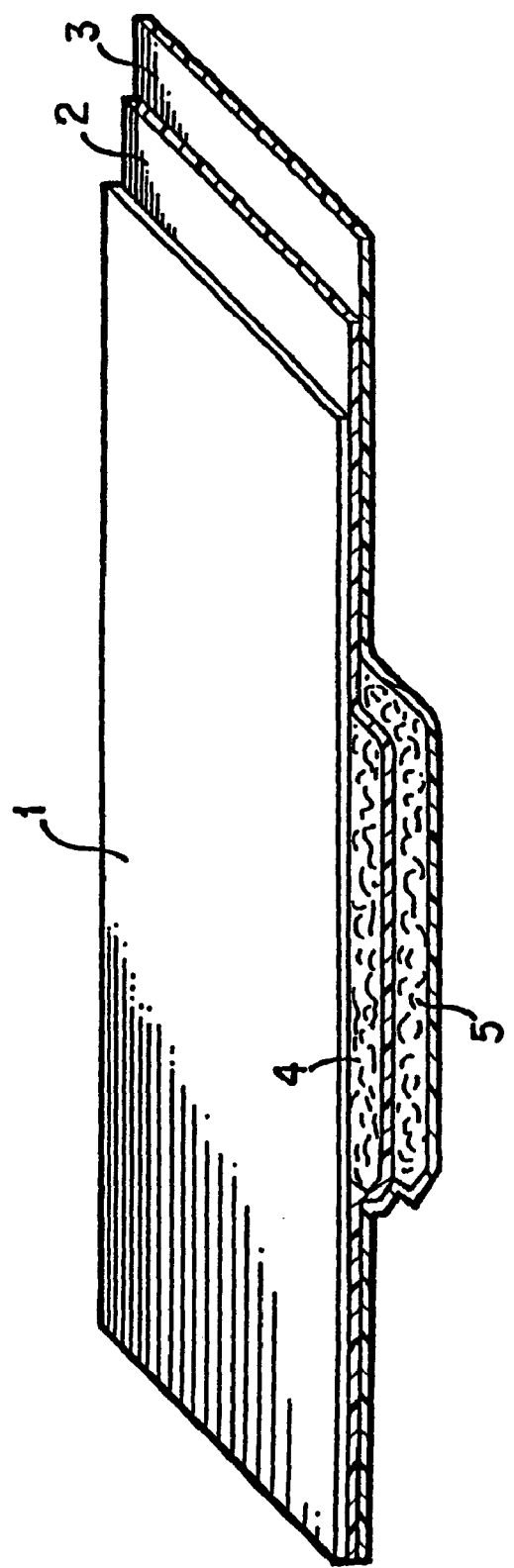

FIG. 42. Diagram of a self-contained TS Wound Dressing.

DESCRIPTION OF THE PREFERRED EMBODIMENTS

Definitions

Unless defined otherwise, all technical and scientific terms used herein have the same meaning as is commonly understood by one of skill in the art to which this invention belongs. All patents and publications mentioned herein are incorporated by reference.

As used herein, a wound includes damage to any tissue in a living organism. The tissue may be an internal tissue, such as the stomach lining or a bone, or an external tissue, such as the skin. As such a wound may include, but is not limited to, a gastrointestinal tract ulcer, a broken bone, a neoplasia, and cut or abraided skin. A wound may be in a soft tissue, such as the spleen, or in a hard tissue, such as bone. The wound may have been caused by any agent, including traumatic injury, infection or surgical intervention.

As used herein, TS is a substance or composition that, upon application to a wound, seals the wound, thereby reducing blood loss and maintaining hemostasis. As used herein, FG is a composition, prepared from recombinant or plasma proteins, that upon application to a wound forms a clot, thereby sealing the wound, reducing blood loss and maintaining hemostasis. FG, supra, is a form of TS.

As used herein, supplemented TS includes any TS that, without substantial modification, can serve as a carrier vehicle for the delivery of a growth factor, drug or other compound, or mixtures thereof, and that, by virtue of its adhesive or adsorptive properties, can maintain contact with the site for a time sufficient for the supplemented TS to produce its desired effect, for example to promote wound healing.

As used herein, a growth factor-supplemented TS is a TS to which at least one growth factor has been added at a concentration that is effective for its stated purpose. The growth factor can, for example, accelerate, promote or improve wound healing, or tissue (re)generation. The growth factor-supplemented TSs may also contain additional components, including drugs, antibodies, anticoagulants and other compounds that: 1) potentiate, stimulate or mediate the biological activity of the growth factor(s) in the TS; 2) decrease. the activities of components of the growth factor-supplemented TS which would inhibit or destroy the biological activities of the growth factor(s) in the sealant; or 3) allow prolonged delivery of the supplement from the TS; 4) possess other desirable properties.

As used herein, a potentiating compound is a compound that mediates or otherwise increases the biological activity of a growth factor in the TS. Heparin is an example of a compound that potentiates the biological activity of HBGF-1.

As used herein, an inhibiting compound is a compound that inhibits, interferes with, or otherwise destroys a deleterious activity of a component of the TS that would interfere with or inhibit the biological activity of a growth factor or factors in the TS. Inhibiting compounds may exert their effect by protecting the growth factor from degradation. An inhibiting compound does not, however, inhibit any activities that are essential for the desired properties, such as, for example, wound healing of the growth factor-supplemented TS. An example of an inhibiting compound is heparin.

As used herein, a growth factor includes any soluble factor that regulates or mediates cell proliferation, cell differentiation, tissue regeneration, cell attraction, wound repair and/or any developmental or proliferative process. The growth factor may be produced by any appropriate means including extraction from natural sources, production through synthetic chemistry, production through the use of recombinant DNA techniques and any other techniques, including virally inactivated, growth factor(s)-rich platelet releasate, which are known to those of skill in the art. The term growth factor is meant to include any precursors, mutants, derivatives, or other forms thereof which possess similar biological activity(ies), or a subset thereof, to those of the growth factor from which it is derived or otherwise related.

As used herein, HBGF-1, which is also known to those of skill in the art by alternative names, such as endothelial cell growth factor (ECGF) and FGF-1, refers to any biologically active form of HBGF-1, including HBGF-1β, which is the precursor of HBGF-1α and other truncated forms, such as FGF. U.S. Pat. No. 4,868,113 to Jaye et al., herein incorporated by reference, sets forth the amino acid sequences of each form of HBGF. HBGF-1 thus includes any biologically active peptide, including precursors, truncated or other modified forms, or mutants thereof that exhibit the biological activities, or a subset thereof, of HBGF-1.

Other growth factors may also be known to those of skill in the art by alternative nomenclature. Accordingly, reference herein to a particular growth factor by one name also includes any other names by which the factor is known to those of skill in the art and also includes any biologically active derivatives or precursors, truncated mutant, or otherwise modified forms thereof.

As used herein, biological activity refers to one or all of the activities that are associated with a particular growth factor in vivo and/or in vitro. Generally, a growth factor exhibits several activities, including mitogenic activity (the ability to induce or sustain cellular proliferation) and also non-mitogenic activities, including the ability to induce or sustain differentiation and/or development. In addition, growth factors are able to recruit or attract particular cells from which the proliferative and developmental processes proceed. For example, under appropriate conditions HBGF-1 can recruit endothelial cells and direct the formation of vessels therefrom. By virtue of this activity, growth factor-supplemented TS may thereby provide a means to enhance blood flow and nutrients to specific sites.

As used herein, extended longevity means at least a two fold increase in the visually observable, useful in vitro lifespan of a TS.

As used herein, demineralized bone matrix (DBM) means the organic matrix of bone that remains after bone is decalcified with hydrochloric or another acid.

As used herein, bone morphogenetic proteins (BMPs) mean a group of related proteins originally identified by their presence in bone-inductive extracts of DBM. At least 8 related members have been identified and are designated BMP-1 through BMP-8. The BMPs are also known by other names. BMP-2 is also known as BMP-2A. BMP-4 is also known as BMP-2B. BMP-3 is also known as osteogenin. BMP-6 is also known as Vgr-1. BMP-7 is also known as OP-1. Bone morphogenetic proteins is meant to include, but is not limited to BMP-1 through BMP-8.

As used herein, augmentation means using a supplemented or unsupplemented TS to change the internal or external surface contour of a component of an animal's body.

As used herein, a damaged bone is a bone which is broken, fractured, missing a portion thereof, or otherwise not healthy, normal bone.

As used herein, a deficient bone is a bone which has an inadequate shape or volume to perform its function.

As used herein, bone or DBM which is to be used to supplement a TS can be in the form of powder, suspension, strips or blocks or other forms as necessary to perform its desired function.

As used herein, organoid means a structure that may be composed of natural, artificial, or a combination of natural and artificial elements, that wholly or in part, replaces the function of a natural organ. An example would be an artificial pancreas consisting of a network of capillaries surrounded by cells transfected with an expression vector containing the gene for insulin. Such an organoid would function to release insulin into the bloodstream of a patient with Type I Diabetes.

Preparation of Supplemented TS

As a first step when practicing any of the embodiments of the invention disclosed herein, the supplement and TS must be selected. The supplement and TS may be prepared by methods known to those of skill in the art, may be purchased from a supplier thereof, or may be prepared according to the methods of this application. In a preferred embodiment, growth factor, drug- or DBM-supplemented FG is prepared.

In any of the embodiments of the present invention the supplement may be added to the fibrinogen, the thrombin, the calcium and/or the water component(s) before they are mixed to form the TS. Alternatively, the supplement(s) can be added to the components as they are being mixed to form the TS.

In embodiments of the present invention, the calcium and/or thrombin may be supplied endogenously from body fluids as, for example, those in a wound.

Preparation of TSs

In certain embodiments of this invention such as, but not limited to, vascular prostheses, and in bone and cartilage augmentation, TS which allows cells to migrate into and/or through it may preferably be used.

Any TS, such as commercially available FG, may be used in some embodiments of this invention. For example, FGs which are well known to those of skill in the art (see, e.g., U.S. Pat. Nos. 4,627,879; 4,377,572; and 4,298,598, all herein incorporated by reference) may be purchased from a supplier or manufacturer thereof, such as IMMUNO AG (Vienna, Austria) and BEHRINGWERKE AG (Germany). For these uses, such as localized drug delivery, the particular composition of the selected TS is not critical as long as it functions as desired. Commercially available FGs may be supplemented with growth factors, antibiotics and/or other drugs for use in the embodiments of this invention including, but not limited to: in vitro cellular proliferation and/or differentiation; drug delivery; growth factor delivery, etc.

For the experiments exemplified herein, FG was prepared from cryoprecipitate from fresh frozen plasma. The components of the FG that were used included: fibrinogen concentrate; thrombin; and calcium ions.

In a preferred embodiment of this invention, the total protein concentration in the prepared FG is from about 0.01 to 500 mg/ml of FG. In a more preferred embodiment, the total protein concentration in the prepared FG is from about 1 to 120 mg/ml FG. In the most preferred embodiment, the total protein concentration in the prepared FG is from about 4 to 30 mg/ml FG.

In a preferred embodiment of this invention, the fibrinogen concentration used to prepare the FG is from about 0.009 to 450 mg/ml of solution. In a more preferred embodiment, the fibrinogen concentration in this preparatory solution is from about 0.9 to 110 mg/ml. In the most preferred embodiment, the fibrinogen concentration in this preparatory solution is from about 3 to 30 mg/ml.

In a preferred embodiment, the thrombin concentration used to prepare the FG is 0.01–350 U/ml. In a more preferred embodiment, the thrombin concentration is 1–175 U/ml. In the most preferred embodiment, the thrombin concentration is 2–4 U/ml.

It is important that the calcium ion concentration be sufficient to allow for activation of the thrombin. In a preferred embodiment, the USP calcium chloride concentration is 0–100 mM. In a more preferred embodiment, the USP calcium chloride concentration is 1–40 mM. In the most preferred embodiment, the USP calcium chloride concentration is 2–4 mM. In some embodiments of this invention, the calcium may be supplied by the tissue or body fluids as, for example, in the wound dressing embodiment.

In preparing the TS, sterile water for injection should be used.

Although the concentration(s) of growth factor(s), drugs and other compounds will vary depending on the desired objective, the concentrations must be great enough to allow them to be effective to accomplish their stated purpose. In a preferred embodiment of this invention, the growth factor concentration is from about 1 ng/ml to 1 mg/ml of FG. In a more preferred embodiment, the growth factor concentration is from about 1 μg/ml to 100 μg/ml of FG. In the most preferred embodiment, the growth factor concentration is from about 5 μg/ml to 20 μg/ml of FG. In a preferred embodiment of this invention the TET or CIP concentration is from 0.01 to 300 mg/ml FG. In a more preferred embodiment of this invention the TET or CIP concentration is 0.01–200 mg/ml. In the most preferred embodiment of this invention the TET or CIP concentration is 1–150 mg/ml. The amount of the supplements to be added can be empirically determined by one of skill in the art by testing various concentrations and selecting that which is effective for the intended purpose and the site of application.

Preparation of Growth Factors

The growth factor(s), or mixture thereof, may be prepared by any method known to those of skill in the art or may be purchased commercially. Any growth factor may be selected including, but not limited to, for example, growth factors that stimulate the proliferation and/or attraction of certain cell types, such as endothelial cells, fibroblasts, epithelial cells, smooth muscle cells, hepatocytes, and keratinocytes, and/or growth factors which inhibit the growth of the same cell types and smooth muscle cells. Such selection may be dependent upon the particular tissue site for which the growth factor-supplemented TS will be applied and/or the type of effect desired. For example, an EGF-supplemented TS may be preferred for application to wounds in the eye and for treating gastric ulcers while an osteogenin-supplemented TS may be preferred for application to bone fractures and bone breaks in order to promote healing thereof.

In another preferred embodiment HBGF-1β was prepared and added to FG. HBGF-1β, or HBGF-1α, or any other active form of HBGF-1, can be purified from natural sources, from genetically engineered cells that express HBGF-1 or a derivative thereof, or by any method known to those of skill in the art.

HBGF-1β has been prepared using recombinant DNA methodology (Jaye et al., U.S. Pat. No. 4,868,113; Jaye et al., *J. Biol. Chem.* 262:16612–16617 (1987)). Briefly, DNA encoding HBGF-10 was cloned into a prokaryotic expression vector, a pUC9 derivative, and expressed intracellularly in *E. coli*. The expressed peptide was then released from the cells by pressure, using a cell disrupter operated on high compression-decompression cycles. After disruption, cell debris was removed by filtration and HBGF-1β was purified from the supernatant using standard methods of protein purification including affinity chromatography on heparin Sepharose™ followed by ion-exchange chromatography on CM-Sepharose™.

In addition to HBGF-1, described above, other growth factors that may be added to the FG include, but are not limited to, HBGF-2, IGF-1, EGF, TGF-β, TGF-α, any platelet-derived growth factor or extract, BMPs, and mixtures of any growth factors. For example, platelet-derived extracts, which serve as rich sources of growth factors, may be added to the TS in addition to or in place of other growth factors, such as HBGF-1.

In a preferred embodiment, a platelet-derived extract, prepared by any method known to those of skill in the art, is added to a TS. Such an extract has been prepared from plasma derived platelets for use with FG.

Platelet-Derived Wound Healing Factor (PDWHF) may be prepared and added to FG (Knighton et al., *Ann. Surg.* 204:322–330 (1986)). Briefly, to prepare PDWHF, blood is drawn into anticoagulant solution and platelet-rich plasma is prepared by refrigerated centrifugation. The platelets are isolated and stimulated with thrombin, which releases the contents of the alpha granule contents. The platelets are removed and an effective concentration of the remaining extract is added to a TS.

Additional Components of Growth Factor-Supplemented TS

Since they are essentially plasma fractions, the TSs contemplated for use with growth factors contain numerous components, some of which may interfere with the biological activity of the selected growth factor(s). For example, thrombin, which is an essential component of FG, can act as a proteolytic enzyme and specifically cleave HBGF-1β. Therefore, it may be necessary to include additional compounds, such as protease or other inhibitors, that protect the selected growth factor(s) from the action of other components in the TS which interfere with or destroy the biological activity of the growth factor(s).

Selection of the particular inhibiting compound(s) may be empirically determined by using methods, discussed below, that assess the biological activity of the growth factor(s) in the TS. Methods to assess biological activity are known to those of skill in the art.

In addition, in order for certain growth factors to exhibit their biological activities, it may be necessary to include compounds that potentiate or mediate the desired activity. For example, heparin potentiates the biological activity of HBGF-1 in vivo (see, e.g., Burgess et al., *Annu. Rev. Biochem.* 58:575–606 (1989)).

The supplemented TS of the present invention may contain compounds such as drugs, other chemicals, and proteins. These may include, but are not limited to: antibiotics such as TET, ciprofloxacin, amoxicillin, or metronidazole, anticoagulants, such as activated protein C, heparin, prostracyclin ($PGI_2$), prostaglandins, leukotrienes, antithrombin III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers; chemoattractants; local anesthetics such as bupivacaine; and antiproliferative/antitumor drugs such as 5-fluorouracil (5-FU), taxol and/or taxotere. These supplemental compounds may also include polyclonal, monoclonal or chimeric antibodies, or functional derivatives or fragments thereof. They may be antibodies which, for example, inhibit smooth muscle proliferation, such as antibodies to PDGF, and/or TGF-β, or the proliferation of other undesirable cell types within and about the area treated with the TS. These antibodies can also be useful in situations where anti-cancer, anti-platelet or anti-inflammatory activity is needed. In general, any antibody whose efficacy would be improved by site-directed delivery may benefit from being used with this TS delivery system.

Assays for Assessing the Wound Healing Properties of a Growth Factor-Supplemented TS In order to ascertain whether a particular growth factor-supplemented TS promotes wound healing and to select optimal concentrations of the growth factor(s) to do the same, the composition may be tested by any means known to those of skill in the art (see, e.g., Tsuboi et al., *J. Exp. Med.* 172:245–251 (1990); Ksander et al., *J. Am. Acad. Dermatol.* 22:781–791 (1990); and Greenhalgh et al., *Am. J. Path.* 136:1235 (1990)). Any method including both in vivo and in vitro assays, by which the activity of the selected growth factor(s) in the TS composition can be assessed may be used. For example, the activity of HBGF-1β has been assessed using two independent in vitro assays. In the first, the proliferation of endothelial cells that had been suspended in a shallow fluid layer covering a plastic surface which had been impregnated with growth factor-supplemented FG was measured. In the second, the incorporation of $^3H$-thymidine in cultured fibroblasts in the presence of HBGF-1 was measured.

In an in vivo assay, FG that had been supplemented with HBGF-1β has been tested for its ability to promote healing in vivo using mice as a model system. In this method identical punch biopsies were made in the dorsal region of the mice, which were then separated into test, treated control and untreated control groups. The wounds in the mice in the test group were treated with the growth factor-supplemented TS. The wounds in the mice in the treated control group were treated with unsupplemented TS. The wounds in the untreated group were not treated with TS. After a time sufficient for detectable wound healing to proceed, generally a week to ten days, the mice were sacrificed and the wound tissue was microscopically examined to histologically assess the extent of wound repair in each group.

The ability of the growth factor-supplemented TS to induce cell proliferation and to recruit cells may also be assessed by in vitro methods known to those of skill in the art. For example, the in vitro assays described above for measuring the biological activity of growth factors and described in detail in the Examples, may be used to test the activity of the growth factor in the TS composition. In addition, the effects of adding inhibiting and/or potentiating compounds can also be assessed.

Generally, the necessity for adding inhibiting and/or potentiating compounds can be empirically determined. For example, in the experiments described below, the HBGF-1β in HBGF-1-supplemented FG was specifically cleaved in a stochastic manner, suggesting that a component of the FG preparation, most likely thrombin, was responsible. Heparin, which is known to bind to HBGF-1 and protect it from certain proteolytic activities, was added to the HBGF-1-supplemented FG. The addition of relatively low concentrations of heparin protected HBGF-1β from cleavage that would destroy its biological activity in the FG. Therefore, TS compositions that include HBGF-1 may include heparin or some other substance that inhibits the cleavage of HBGF-1 by thrombin or other proteolytic components of the FG.

Similarly, the ability of a selected inhibitor to protect a growth factor from degradation by TS components may be assessed by any method known to those of skill in the art. For example, heparin has been tested for its ability to inhibit cleavage of HBGF-1 by thrombin, which is an essential component of FG. To do so, mixtures of various concentrations of heparin and HBGF-1-supplemented FG have been prepared, and incubated for various times. The biological activity of HBGF-1 in the mixture has been tested and the integrity of the HBGF-1 has been ascertained using western blots of SDS gels. Relatively low concentrations, about a 1:1 molar ratio of heparin:HBGF-1, are sufficient to protect HBGF-1 from degradation in FG.

It can also be empirically determined whether a particular compound can be used to potentiate, mediate or enhance the biological activity of a growth factor(s) in TS.

Topical or Internal Application of the Growth Factor-Supplemented TS to an Internal or External Wound Prior to clinical use, the growth factor and TS, or the growth factor-supplemented TS is pasteurized or otherwise treated to inactivate any pathogenic contaminants therein, such as viruses. Methods for inactivating contaminants are well-known to those of skill in the art and include, but are not limited to, solvent-detergent treatment and heat treatment (see, e.g., Tabor et al., *Thrombosis Res.* 22:233–238 (1981) and Piszkiewicz et al., *Transfusion* 28:198–199 (1988)).

The supplemented TS is applied directly to the wound, other tissue or other desired location. Typically for external wounds it can be applied directly by any means, including spraying on top of the wound. It can also be applied internally, such as during a surgical procedure. When it is applied internally, such as to bones, the clot gradually dissolves over time.

Self-Contained Applications of the Supplemented or Unsupplemented TS for Internal or External Wounds The TSs may be formulated as a self-contained wound dressing, or fibrin sealant bandage, which contains the necessary thrombin and fibrinogen components of the FG. The self-contained dressing or bandage is easy-to-use, requiring no advanced technical knowledge or skill to operate. It can even be self-administered as an emergency first aid measure to preserve life until medical assistance becomes available.

The self-contained TS wound dressing or fibrin sealant bandage is an advancement over the current technology in that the field-ready preparation can be stored for long periods, and be used to provide rapid TS treatment of a hemorrhaging wound without the time delay associated with solubilization and mixing of the components. These characteristics make it ideal for use in field applications, such as in trauma packs for soldiers, rescue workers, ambulance/paramedic teams, firemen, and in early trauma and first aid treatment by emergency room personnel in hospitals and clinics, particularly in disaster situations. A small version may also have utility in first aid kits for use by the general public or by medical practitioners.

The self-contained TS wound dressing or fibrin sealant bandage comprises a tissue sealing composition comprising a tissue sealant or fibrin complex of the type previously described. For example, the composition may be comprised of purified fibrinogen, thrombin and calcium chloride with sufficient Factor XIII to produce a fibrin clot. In one embodiment the fibrinogen and Factor XIII components are supplied in the form of topical fibrinogen complex (TFC).

When used on human patients, the components are most preferably pathogen-inactivated, purified components derived from human sources. In particular, the components of the present invention, including additives thereto, are treated with a detergent/solvent, and/or otherwise treated, e.g., by pasteurization or ultrafiltration to inactivate any pathogenic contaminants therein, such as viruses. Methods for inactivating contaminants are well-known to those of skill in the art and include, but are not limited to, solvent-detergent treatment and heat treatment. Solvent-detergent treatment is particularly advantageous in that the proteinaceous components are not exposed to irreversible heat-denaturation.

The calcium and/or Factor XIII components may be contained in either the thrombin and/or the fibrinogen component(s), and/or absorbed from the patient's endogenous calcium present in the fluids escaping from the wound. Thrombin may also be supplied endogenously. Either or both of the thrombin or fibrinogen components can be, but does not have to be, supplemented in each of the following embodiments with one or more growth factors, drugs, inhibiting compounds (to inhibit the activities of the sealant that may interfere with any of the biological activities of the growth factor or drug), and potentiating compounds (to potentiate, mediate or enhance any of the biological activities of the growth factor or drug), compounds which inhibit the breakdown of the fibrin clot, or dyes.

The growth factor may include, e.g., fibroblast growth factor-1, fibroblast growth factor-2 and fibroblast growth factor-4; platelet-derived growth factor; insulin-binding growth factor-1; insulin-binding growth factor-2; epidermal growth factor; transforming growth factor-α; transforming growth factor-β; cartilage-inducing factors -A and -B; osteoid-inducing factor; osteogenin and other bone growth factors; collagen growth factor; heparin-binding growth factor-1; heparin-binding growth factor-2; and/or their biologically active derivatives.

The drug may be an analgesic, antiseptic, antibiotic or other drug(s), such as antiproliferative drugs which can inhibit infection, promote wound healing and/or inhibit scar formation. More than one drug may be added to the composition, to be released simultaneously, or the drug may be released in predetermined time-release manner. Such drugs may include, for example, taxol, tetracycline free base, tetracycline hydrochloride, ciprofloxacin hydrochloride or 5-fluorouracil. The addition of taxol to the fibrin sealant complex may be particularly advantageous. Further, the drug may be a vasoconstrictor, e.g., epinephrine; or the drug may be added to stabilize the tissue sealant or fibrin clot, e.g., aprotinin. The supplement(s) is at a concentration in the TS such that it will be effective for its intended purpose, e.g., an antibiotic will inhibit the growth of microbes, an analgesic will relieve pain, etc.

Dyes, markers or tracers may be added, for example, to indicate the extent to which the fibrin clot may have entered the wound, or to measure the subsequent resorption of the fibrin clot, or the dye may be released from the tissue sealant in a predetermined, time-release manner for diagnostic purposes. The dyes, markers or tracers must be physiologically compatible, and may be selected from colored dyes, including water soluble dyes, such as toluidine blue, and radioactive or fluorescent markers or tracers which are known in the art. The dyes, markers or tracers may also be compounds which may be chemically coupled to one or more components of the tissue sealant. In addition, the marker may be selected from among proteinaceous materials which are known in the art, which upon exposure to proteolytic degradation, such as would occur upon exposure to proteases escaping from wounded tissue, change color or develop a color, the intensity of which can be quantified.

Moreover, when the TS is used to replace or repair wounded or damaged bone or ossified tissue, the composition may also be supplemented with effective amounts of demineralized bone matrix and/or bone morphogenic proteins, and/or their biologically compatible derivatives.

The concentration of the fibrinogen and/or thrombin components of the self-contained TS wound dressing or fibrin sealant bandage may have a significant effect on the density and clotting speed of the final fibrin matrix. This principle may be used to satisfy specific uses of the self-contained TS wound dressing or fibrin sealant bandage in specialized situations. For example, the treatment of an arterial wound may require the fibrin clot to set very rapidly and with sufficient integrity to withstand pressurized blood flow. On the other hand, when filling deep crevices in a wound, treatment may require the components to fill the wound completely before the fibrin clot sets.

The Gel Pack Embodiments

In the gel pack embodiment of the self-contained dressing, the thrombin and fibrinogen components are individually contained in independent quick-evaporating gel layers (e.g., methylcellulose/alcohol/water), wherein the two gel layers are separated from each other by an impermeable membrane, and the pair are covered with an outer, protective, second impermeable membrane. The bandage may be coated on the surface that is in contact with the gel in order to insure that the gel pad remains in place during use. (See FIG. 42).

In use, the membrane separating the two gel layers is removed, allowing the two components to mix. The outer membrane is then removed and the bandage is applied to the wound site. The action of the thrombin and other components of the fibrinogen preparation cause the conversion of the fibrinogen to fibrin, in the manner previously disclosed for other FS applications. This results in a natural inhibition of blood and fluid loss from the wound, and establishes a natural barrier to infection.

In a similar gel pack embodiment, both the thrombin component, and the plastic film separating the thrombin gel and the fibrinogen gel, may be omitted. In operation, the outer impervious plastic film is removed and the bandage applied, as previously described, directly to the wound site. The thrombin and calcium naturally present at the wound site then induce the conversion of fibrinogen to fibrin and inhibit blood and fluid loss from the wound as above.

This alternative embodiment of the gel pack has the advantage of being simpler, cheaper, and easier to produce. However, there may be circumstances in which a patient's wounds have insufficient thrombin to effectively transform the fibrinogen gel into a fibrin tissue sealant. In those cases, the thrombin component must be exogenously supplied, as in the earlier-described gel pack embodiment of the invention.

The Fibrin Sealant Bandage Embodiments

A fibrin sealant bandage embodiment is formulated for applying a tissue sealing composition to wounded tissue in a patient, wherein the bandage comprises, in order: (1) an occlusive backing; (2) a physiologically-acceptable adhesive layer on the wound-facing surface of the backing; and (3) a layer of dry materials comprising an effective amount, in combination, of (a) dry, virally-inactivated, purified fibrinogen complex, (b) dry, virally-inactivated, purified thrombin, and as necessary (c) effective amounts of calcium and/or Factor XIII to produce a tissue-sealing fibrin clot upon hydration, wherein the layer of dry materials is affixed to the wound-facing surface of the adhesive layer. In one embodiment, the occlusive backing and the physiologically-acceptable adhesive layer are one and the same, if the backing layer is sufficiently adhesive to effectively bind the layer of dry materials.

In another embodiment, a removable, waterproof, protective film is placed over the layer of dry materials and the exposed adhesive surface of the bandage for long-term stable storage. In operation the waterproof, protective film is removed prior to the application of the bandage over the wounded tissue.

The tissue sealant component of the bandage in one embodiment is activated at the time the bandage is applied to the wounded tissue to form a tissue sealing fibrin clot by the patient's endogenous fluids escaping from the hemorrhaging wound. Preferably, the tissue sealant is hydrated and fluid loss from the wound will be significantly diminished within minutes of application of the bandage to the wounded tissue. Although the speed with which the fibrin clot forms and sets may be to some degree dictated by the application, e.g., rapid setting for arterial wounds and hemorrhaging tissue damage, slower setting for treatment of wounds to bony tissue, preferably the fibrin clot will form within twenty minutes after application. More preferably, this effect will be evident within ten minutes after application of the bandage. Most preferably, the fibrin clot will form within two to five minutes after application. In the embodiment comprising the most rapidly forming fibrin clot, the tissue seal will be substantially formed within 1–2 minutes, more preferably within 1 minute, and most preferably within 30 seconds after application.

It may be necessary to use pressure in applying the fibrin sealant bandage until the tissue sealing fibrin clot has formed over the wound site.

In the alternative, in situations where fluid loss from the wound is insufficient to provide adequate hydration of the dry tissue sealant materials, or where time is of the essence, as in a life-threatening situation, the tissue sealant components are hydrated by a suitable, physiologically-acceptable liquid prior to application of the bandage to the wounded tissue.

To construct the bandage, the dry materials may be obtained, for example, by lyophilization or freeze-drying, or suitable, commercially-available materials may be utilized. Anhydrous $CaCl_2$ may also be added to the dry TS components to accelerate the speed of fibrin formation upon hydration of the fibrin sealant bandage. The binding of the dry materials to the adhesive or backing layer may be enhanced by adding a binder, preferably a water soluble binder, to the dry components.

The backing of the fibrin sealant bandage may be of conventional, non-resorbable materials, e.g., a silicone patch or plastic material; or it may be of biocompatible, resorbable materials. The backing material may act as more than a delivery device. Its preferred composition is determined by the desired application of the fibrin sealant bandage. For example, a non-resorbable backing is appropriate for many external uses, where it provides strength and protection for the fibrin clot. In an alternative embodiment, the non-resorbable backing is reinforced, e.g., with fibers, to provide extra strength and durability for the protective covering over the fibrin clot.

Subsequent removal of the clot with the backing is acceptable in many situations, such as when the fibrin sealant bandage is used as a first aid measure until medical assistance becomes available. In such a situation, the clot will have served its purpose to prevent life threatening loss of fluid, and it will be desirable to remove the clot without causing additional tissue damage to permit proper treatment or surgical repair of the wound.

In the alternative, the non-resorbable backing may be used to provide strength to the tissue sealing fibrin clot during its formation, e.g., when the hemorrhaging fluids are escaping under pressure, as in an arterial wound. Yet, if such a wound is internal, it is advantageous to remove the backing from the fibrin clot without disturbing the tissue seal. Therefore, a fibrin sealant bandage is provided in which the adhesive layer is of a material having a lower shear strength than that of the fibrin clot, permitting removal of the backing without damage to the fibrin clot or the tissue surrounding the wound.

By comparison, certain internal applications mandate the use of a resorbable backing to eliminate the need for subsequent removal of the dressing. A resorbable material is one which is broken down spontaneously or by the body into components which are consumed or eliminated in such a manner as to not significantly interfere with healing and/or tissue regeneration or function, and without causing any other metabolic disturbance. Homeostasis is preserved. Materials suitable for preparing the biodegradable backing include proteinaceous substances, e.g., fibrin, collagen, keratin and gelatin, or carbohydrate derived substances, e.g., chitin, chitosan, carboxymethylcellulose or cellulose, and/or their biologically compatible derivatives.

The adhesive layer, if separate from the occlusive backing layer, is selected on the basis of the intended application of the fibrin sealant bandage, and may comprise conventional adhesive materials. Antiseptic may be added to the adhesive layer.

If the tissue sealing fibrin clot is to be removed from the wound with the occlusive backing, such as prior to surgery, the adhesive must be sufficient to affix the dry material layer to the occlusive backing, and to maintain an adhesive capability after hydration which is greater than the sheer strength of fibrin.

If the tissue sealing fibrin clot is to remain in position over the wound, but the occlusive backing must be removed after application, the adhesive must be sufficiently sticky to affix the dry material layer to the occlusive backing, but yet have an adhesive capability after hydration which is less than the sheer strength of the fibrin clot. In the alternative, the adhesive layer may be of a material which becomes solubilized or less sticky during hydration of the dry materials, permitting removal of the backing from the fibrin clot. In the alterative for such purposes, the dry material layer may be affixed directly to the occlusive bandage.

In another embodiment, the adhesive layer comprises two different adhesives to permit removal after hydration of the occlusive layer without disturbing the tissue sealing fibrin clot. Typically, in such a situation the dry, tissue-sealant component materials are affixed to a specific region of the backing, the "inner region," e.g., the center, with an unencumbered area of adhesive extending beyond the area of dry material, the "outer region."

The outer region of adhesive is affixed directly to the skin or tissue surrounding or adjacent to the wound in such a way that the dry material region of the bandage forms a fibrin clot directly over the wound. The adhesive layer on the region of backing which is not covered by the dry material layer of the bandage is sufficient to affix the fibrin sealant bandage to the tissue surrounding the wound until its physical removal. The adhesive on the outer region must be sufficient to hold the bandage in place, even if fluids are hemorrhaging from the wound under pressure, e.g., an arterial wound.

The inner region of adhesive is sufficiently sticky to affix the dry material layer to the occlusive backing, but yet have an adhesive capability after hydration which is less than the sheer strength of the fibrin clot. In the alternative, the inner region of adhesive is of a material which becomes solubilized or less sticky during hydration of the dry materials, permitting removal of the backing from the fibrin clot. In the alterative for such purposes, the dry material layer may be affixed in the inner region directly to the occlusive bandage, with an adhesive layer added only to the outer layer.

Thus, in the two adhesive embodiment, the backing of the fibrin sealant bandage remains in place affixed to the tissue surrounding the wound until the bandage is physically removed. But upon removal, the backing separates from the tissue sealing fibrin clot without disturbing the tissue seal.

The Dual-Encapsulated Embodiments of the Fibrin Sealant Bandage

In yet another embodiment of the fibrin sealant bandage, an independent hydrating layer comprising an effective amount of carbonated water or physiologically-acceptable buffered hydrating agent, such as PBS, or comparable gel, is contained within a rupturable, liquid-impermeable container. The rupturable, liquid-impermeable container encapsulating the hydrating layer is affixed directly to the above-described occlusive bandage layer or to the above-described adhesive layer adjacent to the occlusive bandage. Affixed to the exposed side (the side which is not attached to the backing or adhesive layer) of the rupturable, liquid-impermeable container encapsulating the hydrating layer is a dry layer of finely-ground, powdered fibrin components, as described above. The layer of dry components includes powdered fibrinogen or fibrinogen complex, thrombin, and as necessary sufficient calcium and/or Factor XIII to, upon hydration, form a fibrin clot.

The dual layers (the dry layer and the hydrating layer) are together covered on all surfaces not in contact with the occlusive backing or adhesive material affixing the layers to the occlusive backing, with an outer, protective, second impermeable membrane. Thus, in this dual-layer embodiment, the contents are entirely encapsulated within an impermeable container, wherein one side is the occlusive backing material and the other side and all edges are formed by the outer, protective, second impermeable membrane.

In operation, the inner liquid-impermeable container encapsulating the hydrating layer is physically ruptured to release the hydrating material contained therein into the dry fibrin component layer, resulting in a fully-hydrated tissue sealing fibrin clot to inhibit blood and fluid loss from the wound, and to provide a natural barrier to infection. The outer, second impermeable membrane retains the released hydrating material in contact with the dry components until a malleable fibrin complex forms, at which time the outer membrane is physically removed and the bandage placed over the wound to form a tissue sealant.

In the alternative, the outer membrane may be physically removed, and the dual layers forcefully applied to the wound area in a manner which ruptures the inner liquid-impermeable container and releases the hydrating agent into the dry fibrin components so that the tissue sealing fibrin clot is formed directly on the wounded tissue.

As in other embodiments of the fibrin sealant bandage, the selected adhesives and backing materials may be determined by the intended application of the bandage. The backing may be removable or resorbable, and the adhesive may have the intended purpose upon removal of the bandage of removing the tissue sealant from the wound, or of leaving the tissue sealing fibrin clot undisturbed. The adhesive may be a separately bound layer, or the backing may itself act as an adhesive to affix the dry fibrin components.

The thrombin, calcium and Factor XIII components which are necessary to form the fibrin complex may be affixed as dry material(s) in the dry material layer, or they may be included in liquid or gel form in the hydrating layer. Moreover, they may be divided between the two layers, so long as all of the necessary fibrin-forming components are present, and the dry layer remains non-hydrated until the bandage is used. In addition, additives, such as the previously disclosed growth factors, antibiotics, antiseptics, antiproliferative drugs, etc. may also be included in this embodiment of the fibrin sealant bandage.

If the hydrating layer contains a liquid supersaturated with gas, the dry material layer will be hydrated as an expandable, foaming, fibrin tissue sealant. In the alternative, the dry material layer may be supplemented with materials which produce gas, and hence foaming, upon contact with the hydrating agent.

If the hydrating layer is in the form of a gel, such as a quick-evaporating gel layers (e.g., methylcellulose/alcohol/water), the rupture of the surrounding impermeable barrier permits the dry material fibrin components to directly contact the hydrating layer as disclosed above to produce the tissue sealing fibrin clot. The gel layer, in the manner described for a liquid hydrating layer, may comprise any one, or all, of the thrombin, calcium or Factor XIII elements of the fibrin complex, and/or any one of the above-disclosed additives.

In an alternate dual layer embodiment, the tissue sealant is delivered as a wound sealing dressing, which need not be affixed to a backing. The components are organized essentially as a capsule within a capsule, wherein the term capsule is used to define a broad concept, rather than a material. The above-described encapsulated hydrating layer is itself contained within a second encapsulating unit, which contains both the dry fibrin component materials and the encapsulated hydrating layer.

In operation, the inner, liquid-impermeable container encapsulating the hydrating layer is physically ruptured to release the hydrating material contained therein into the dry fibrin component layer, both of which remain completely contained within the outer, second encapsulating unit. The integrity of the outer, second encapsulating unit is not broken when the inner container encapsulating the hydrating layer is physically ruptured.

The mixing of the hydrating layer with the dry fibrin components within the outer encapsulating unit results in a fully-hydrated tissue sealing fibrin clot, which is then released or expelled onto wounded tissue to form a tissue seal. To release the fibrin mass, the outer encapsulating unit is physically cut or torn, either randomly or at a specific location on the surface, e.g., to form a pour spout to direct the flow of the malleable fibrin mass onto the wound site.

If the hydrating layer is a agent supersaturated with gas, the mixing of the hydrating agent with the dry fibrin components results in an expandable foaming mixture, which is then applied to the wounded tissue. The foaming may, in the alternative, be achieved by hydration of the dry component layer.

The Self-Foaming Fibrin Sealant Embodiments

A self-foaming fibrin sealant dressing embodiment for treating wounded tissue in a patient is formulated as an expandable foam comprising a fibrin-forming effective amount, in combination, of (1) virally-inactivated, purified fibrinogen, (2) virally-inactivated, purified thrombin, and as necessary (3) calcium and/or Factor XIII; wherein said composition does not significantly inhibit full-thickness skin wound healing. The previously described TS components are stored in a canister or tank with a pressurized propellant, so that the components are delivered to the wound site as an expandable foam, which will within minutes form a fibrin seal.

Acceptable formulations of the expandable foam embodiment provide the hydrated components of a fibrin clot, which in operation expand up to twenty-fold. The extent of expansion of the tissue sealing fibrin clot, however, is determined by its intended application.

For example, use of the expandable foam fibrin sealant dressing within the abdomen provides a fibrin tissue sealant to significantly diminish or prevent blood or fluid loss from injured internal tissues organs or blood vessels, while also providing a barrier to infection. However, at the same time the expansion of the foam must be controlled to prevent harmful pressure on undamaged tissue, organs or blood vessels. Such a situation may warrant the use of an expandable foam dressing in which the expansion is limited to only 1- or 2-fold, and not more than 5–10 fold.

By comparison, use of the expandable foam fibrin sealant dressing to fill gaps within bone, may warrant the use of material which expands at a much greater rate to produce a tight and firm seal over the wounded area. Arterial wounds may also respond well to a highly pressurized foam tissue sealant dressing. The extent of the expansion of such material may be in the range of above 20-fold, although preferably 10–20 fold, or more preferably 5–10 fold. An expansion of less than 5-fold, including 1- to 2-fold may also be applicable to repair of blood vessels or injured bone, for example in small areas, such as the inner ear.

Like the expansion rate, the set-up time for the formation of the fibrin seal using the expandable foam fibrin dressing is also related to its intended application. In certain situations loss of life may be imminent, such as in a patient who has suffered arterial wounds or damaged heart tissue. In such a situation the fibrin dressing must expand very rapidly and form the fibrin tissue seal as quickly as possible, necessarily before exsanguination. Preferably the seal will set-up and significantly diminish the patient's fluid loss within 2 minutes or less, more preferably in 1–2 minutes, and most preferably in less than 1 minute.

On the other hand, not all wounds are immediately life threatening. For example, the strength of the tissue sealant repair of bony tissue is more important than a rapid set-up time. In such situations, the composition of the tissue sealing fibrin clot may be modified to permit greater cross-linking or thickening of the fibrin fibrils, or to permit delivery of a more dilute composition which will continue to expand for a longer period of time. Such formulations may either permit or require a slightly longer time to set-up the tissue sealing fibrin clot. Although a set-up time of under 1 minute is appropriate for such applications, set-up times of 1–2 minutes, or up to 5 minutes would be acceptable. In circumstances recognizable to one of ordinary skill in the art, a long set-up time of 5–10 minutes, or even up to twenty minutes, may be acceptable in non-life threatening situations.

The delivery devices, e.g., canister, tank, etc., may be developed especially for the present application, or they may be commercially available. The canister may comprise either a single or multiple reservoirs. Separate reservoirs, although more expensive, will advantageously permit the hydrated components to remain separated and stable until they are mixed upon application.

The propellant must be physiologically acceptable, suitable for pharmacological applications, and may include conventionally recognized propellants, for example, $CO_2$, $N_2$, air or inert gas, such as freon, under pressure. In the alternative, the dry fibrin components may be supplemented with material(s) which produce gas, and hence foaming, upon contact with the hydrating agent.

Since delivery pressure of the expandable foam fibrin dressing from the delivery device, when combined with the composition of the fibrin clot itself and its set-up time, determines the extent of expansion of the dressing, the delivery pressure is determined by the nature of the wound being treated. As described above, certain wounds require immediate formation of the tissue sealing fibrin clot to prevent loss of life, while others wounds require slow delivery or time to form extensive cross-links to strengthen the tissue sealing composition. Therefore, delivery pressure may ideally be situation specific.

Pressure of 1 atmosphere, or less (14.7 lbs/inch$^2$) will provide a low level of expansion and a slower rate of delivery. However, certain life threatening situations may warrant a delivery pressure of 1–5 atmospheres, or more. In most cases, the delivery pressure chosen corresponds to that of commercially available canister devices. As an addition factor, the delivery pressure may be important to keep the tissue sealant material from clogging delivery lines or devices.

Combined Embodiments of the Self-Contained Wound Dressing and Fibrin Sealant Bandage Finally, certain traumatic injuries will be best treated by combining several embodiments of the self-contained fibrin sealant dressing. For example, in serious car accidents or injuries caused by antipersonnel-mines or explosives, the wounds may be not only life-threatening but extensive, involving large, jagged openings in tissue or bone with significant internal damage, often with accompanying serious burns. Such wounds may present numerous severed arteries and blood vessels in addition to extensive areas of wounded tissue. In such wounds, it may be advantageous to first liberally apply a rapidly setting expandable fibrin foam dressing to quickly control hemorrhaging, and then to wrap the entire area in an embodiment of the fibrin sealant bandage to support and protect the wounded area and seal slow fluid loss from, for example, burned tissue, until the victim can be transported to a medical facility, or until professional medical assistance can be administered. In most instances, additional formulations of the fibrin sealant dressing will then be applied by the trained personnel for the long-term repair, treatment and protection of the injured tissue.

The following examples are included for illustrative purposes only and are not intended to limit the scope of the invention.

EXAMPLE 1

Preparation of HBGF-1 For Supplementation of FG

An 800 ml culture of recombinant *E. coli* containing a plasmid that included DNA encoding HBGF-1β was prepared. After induction and culturing for 24 hours at 37° C., the cells were centrifuged and the supernatant was discarded. The cell pellet was resuspended in 25 mls of 20 mM phosphate buffer, containing 0.15 M NaCl, pH 7.3. The suspended cells were disrupted with a cell disrupter and the cell debris was separated from the resulting solution by centrifugation at 5000 g for 20 min.

The pellet was discarded and the supernatant containing the solubilized HBGF-1β and other bacterial proteins was loaded onto a 2.6 cm diameter by 10 cm high column of Heparin-Sepharose™ (Pharmacia Fine Chemicals, Upsala, Sweden). The column was washed with 5 column volumes of 0.15 M NaCl in 20 mM phosphate buffer, pH 7.3, and then was eluted with a 0.15 M NaCl in 20 mM phosphate buffer to 2.0 M NaCl gradient.

The eluate was monitored by UV absorption at 280 nm. Three peaks of UV absorbing material eluted and were analyzed by SDS polyacrylamide gel electrophoresis. Peak number three electrophoresed as a single band at about 17,400 daltons and contained substantially pure HBGF-1β.

In order to further insure that the HBGF-1β was free of contaminating bacterial proteins, peak number three, which contained the growth factor activity, was dialyzed overnight against 20 mM histidine, 0.15 M NaCl, pH 7.5. Two mg of protein was loaded onto a 1 ml CM-Sepharose™ (Pharmacia, Upsala, Sweden) ion exchange column. The column was washed with 10 bed volumes (0.5 ml/min) of 20 mM histidine, 0.15 M NaCl, pH 7.5 and eluted with a gradient of 0.15 M NaCl to 1.0 M NaCl in 20 mM histidine, pH 7.5. The eluate was monitored by UV absorption at 280 nm and HBGF-1β was identified by SDS polyacrylamide gel electrophoresis.

This purified HBGF-1 was used to supplement FG in subsequent examples.

EXAMPLE 2

Stability of HBGF-1

It was necessary to add an ingredient to the FG that would inhibit or prevent the digestion of HBGF-1β by thrombin (Lobb, *Biochem.* 27:2572–2578 (1988)), which is a component of FG. Heparin, which adsorbs to HBGF-1, was selected and tested to determine whether it could protect HBGF-1 from digestion by thrombin and any other proteolytic components of the FG. The stability of HBGF-1 in the presence of increasing concentrations of heparin was assessed.

Solutions containing HBGF-1β (10 μg/ml), thrombin (250 U/ml), and increasing concentrations of heparin (0, 0.5, 5, 10, 20, and 50 U/ml) were incubated at 37° C. Aliquots were periodically removed from the incubating solutions and were frozen and stored at −70° C. for further testing.

After the incubation was complete, the samples were thawed and separated on 15% SDS polyacrylamide gels under reducing conditions according to the method of Laemmli (*Nature* 227:680 (1970)). The gel was then electroblotted onto nitrocellulose and the band corresponding to HBGF—I was identified using an affinity-purified polyclonal rabbit antiserum to HBGF-1. The Western blots are shown in FIG. 1 on which the HBGF-1β band at 17,400 mw can be seen. The results indicated that in the presence of concentrations of heparin as low as 5 U/ml, HBGF-1β was protected from digestion by thrombin. In addition, as described in Example 3, its biological activity was not altered.

EXAMPLE 3

The Biological Activity of HBGF-1β after Incubation in the Presence of Heparin and Thrombin The biological activity of HBGF-1 in the incubation mixture that contained 5 U/ml of heparin, and was described in Example 2, was measured using an $^3$H-thymidine incorporation assay with NIH 3T3 cells.

NIH 3T3 cells were introduced into 96 well plates and were incubated at 37° C. under starvation conditions in Dulbecco's Modified Medium (DMEM; GIBCO, Grand Island, N.Y.) with 0.5% fetal bovine serum (BCS; GIBCO, Grand Island, N.Y.) until the cells reached 30 to 50% confluence. Two days later, varying dilutions of HBGF-1 from the samples prepared in Example 2 were added to each well without changing the medium. Diluent (incubation buffer) was added in place of growth factor for the negative controls and DMEM with 10% BCS, which contains growth factors needed for growth, was added in place of the HBGF-1 sample for the positive controls.

After incubation at 37° C. for 18 hours, 0.25 μCi of $^3$H-thymidine, specific activity 6.7 μCi/mol, was added to each well and the incubation was continued at 37° C. for an additional 4 hours. The plates were rinsed with phosphate-buffered saline (PBS) and fixed with 0.5 ml cold 10% trichloracetic acid (TCA) for 15 min at 4° C. The TCA was removed, the plates were rinsed with PBS and the acid-precipitable material was solubilized with 0.5 ml/well of 0.1 N sodium hydroxide for 1 hour at room temperature. The samples were transferred to scintillation vials and 10 ml of scintillation fluid (New England Nuclear, Aquasure™) was added per vial.

The results, which are shown in FIG. 2, demonstrated that HBGF-1, which had been incubated in the presence of thrombin and heparin, retained its biological activity. The observed concentration dependence of thymidine incorporation was independent of incubation time and was typical of that expected for the dependence of the proliferation of cells as a function of growth factor concentration. Growth factors typically exhibit an optimal concentration at which cell proliferation is maximal.

The biological activity of HBGF-1 in the presence of thrombin and heparin was also measured by observing endothelial cell proliferation. The surfaces of petri dishes were impregnated with the HBGF-1 supplemented FG. A shallow layer of endothelial cells was added and the number of cells was measured. Over time the number of cells increased. In addition, the cells appeared to be organizing into vessels.

Therefore, HBGF-1 retains its biological activities in FG that includes heparin, which protects HBGF-1 from the degradative activity of thrombin and may also potentiate the biological activity of the HBGF-1 in the growth factor-supplemented FG.

EXAMPLE 4

HBGF-1 Diffusion from a FG Clot

A FG clot was formed in a 5 ml plastic test tube by mixing 0.3 ml of the fibrinogen complex containing 10 U/ml heparin and thrombin and 40 mM $CaCl_2$. Four test tubes were set up as follows:

(A) 0.5 U/ml thrombin and 10 μg/ml HBGF-1;
(B) 0.5 U/ml thrombin and 50 μg/ml HBGF-1;
(C) 5 U/ml thrombin and 10 μg/ml HBGF-1; and
(D) 5 U/ml thrombin and 50 μg/ml HBGF-1.

Each clot was covered with 0.2 M histidine buffer, pH 7.3. Thirty μl samples of the overlying buffer were removed from each tube every two hours and were run on a western blot.

The results of the experiment demonstrated that HBGF-1 diffusion out of the clot is a function of time and its concentration in the clot, and that the concentration of thrombin in the clot does not affect the rate at which HBGF-1 is released from the clot.

EXAMPLE 5

The Behavior of Human Umbilical Vein Endothelial Cells in Growth Factor-Supplemented FG: The Effect of Wild Type and Mutant FGF-1

To study the in vitro effects of acidic fibroblast growth factor (FGF-1)-supplemented FG on human endothelial cells, suspensions of these cells were added to 10 cm diameter petri dishes that contained evenly spread layers of 2.5 ml of FG containing approximately 9 mg of fibrinogen per ml and 0.25 NIH units of thrombin per ml. The FG was supplemented in the following ways:

(A) No added growth factor;
(B) Supplemented with 100 ng/ml of active, wild-type FGF-1;
(C) Supplemented with 100 ng/ml of inactive, mutant FGF-1; or
(D) Supplemented with 10 ng/ml of active, wild-type FGF-1.

The cells seeded onto the FG layer were maintained for 7 days in DMEM containing 10% fetal bovine serum (FBS).

The cells became elongated and proliferated efficiently when in contact with FG supplemented with biologically active FGF-1 (FIGS. 3 and 4). In contact with unsupplemented FG (FIG. 5) or with FG supplemented with biologically inactive mutant FGF-1 (FIG. 6), the cells become elongated but proliferated relatively slowly.

EXAMPLE 6

The Behavior of Human Umbilical Vein Endothelial Cells in FGF-1-Supplemented FG

To study their growth, human umbilical endothelial cells, $10^5$ or more cells per ml, were embedded in FG, the protein concentration of which was 4 mg/ml. The concentration of thrombin in the FG was adjusted to 0.6 NIH U/ml. The culture medium used in all of the experiments was M199 (Sigma Chemical Co., St. Louis, Mo.) supplemented with 10% fetal bovine serum, 10 µg/ml streptomycin, 100 U/ml penicillin, 1 ng/ml FGF-1 and 10 U/ml heparin.

Within 24 hours in FG the cells became elongated, multipodial and formed a cellular network when they came in contact with each other (FIG. 7). This growth continued for at least 5 days. FIG. 8 shows this situation at 48 hours.

As a control, an identical cell suspension was cultured on a surface coated with fibronectin at 10 µg/cm$^2$. Control cells acquired a cobblestone shape and maintained this morphology for at least 5 days. FIGS. 9 and 10 show this situation at 24 and 48 hours, respectively.

EXAMPLE 7

The Behavior of PMEXNEO-3 T3-2.2 Cells In FG

PMEXNEO-3T3-2.2 cells are fibroblast cells that contain a modified genome with the potential to express genetically engineered proteins (Forough et al., *J. Biol. Chem.* 268: 2960-2968 (1993)). To determine the behavior of these cells in FG, $10^5$ cells per well were cultured under three conditions: (1) embedded in FG; (2) on the surface of FG; and (3) in the absence of FG (controls). The experiments were carried out in duplicate in 24-well plates in DMEM media (Sigma Chemical Co., St. Louis, Mo.) supplemented with 10% FBS. The FG protein concentration was 4 mg/ml. In identical experiments the medium was supplemented with 1.5% FBS was used as negative controls.

In the presence of media supplemented with 10% FBS, the cells in all 3 groups grew and became confluent. In the negative control experiments in which the media was supplemented with 1.5% FBS, the cells grew and survived for at least five days in the presence of FG, but not without it. However, their growth was faster in FG supplemented with 10% FBS than in that supplemented with 1.5% FBS. In the absence of FG, in the media supplemented with 1.5% FBS, the cells died within 48 hours. The criteria for survival was the ability of the tested cells to proliferate upon transfer to fresh media supplemented with 10% FBS.

EXAMPLE 8

The Endothelializadon of Expanded PTFE Vascular Grafts by HBGF-1 Pretreatment

Two studies demonstrated that pretreatment of blood-contacting biomaterials with endothelial cell (EC) mitogens enhanced endothelialization. The first study examined the in vivo washout characteristics of HBGF-1-supplemented FG suspension applied to expanded PTFE grafts implanted into rabbit aortas. In the second study similar grafts were implanted into the aortaileac position in dogs. HBGF-1, an angiogenic factor, was used in studies. Other growth factors such as a FGF, FGF-4 and/or OP-1 can also be used as a supplement(s) for the vascular grafts.

A. Washout Study

In general, the modified FG was sterilely prepared by adding approximately 1 ng/cm$^2$ area of the inner and outer graft surfaces of human recombinant $^{125}$I-HBGF-1, 20 µg/cm$^2$ porcine intestinal mucosal heparin, and 2.86 mg/cm$^2$ fibrinogen to $2.86 \times 10^{-2}$ U/cm$^2$ reconstituted, commercially available, human thrombin (1000 U/ml) to induce polymerization.

The $^{125}$I-HBGF-1 was specifically prepared as follows. Fibrinogen was reconstituted by adding 500 mg of fibrinogen into 25 ml of PBS to produce a fibrinogen concentration of 20 mg/ml of PBS. Three ml of this solution which contained 60 mg fibrinogen were placed into 12 Eppendorf plastic tubes and maintained at −70° C. Each of these aliquots was used individually.

The thrombin was reconstituted by diluting a commercially available preparation thereof (Armour Pharmaceutical Co., Kankakee, IL) at a concentration of 1000 U/ml by a factor of 1:10 in sterile solution to produce a concentration of 100 U/ml. This thrombin solution was again diluted 1:10 to produce a solution of 10 U/ml.

The bovine heparin (Upjohn, Kalamazoo, Mich.) was reconstituted by diluting the preparation at a concentration of 1000 U/ml by a factor of 1:1000 using normal saline.

One and 48/100 (1.48) ml of the reconstituted fibrinogen, 63 µL of the reconstituted heparin, plus 15.66 µL of $^{125}$I-HBGF-1 were mixed in a glass scintillation tube. This mixture was then aspirated into a 3 ml plastic syringe. Five ml of the reconstituted thrombin was placed into a glass scintillation tube.

One end of the expanded PTFE graft was placed over a plastic 3-way stopcock nozzle and was secured there with a 2-0 silk tie. The PTFE was then encircled with a 3×3 cm square of Parafilm™ which was then crimped there with a straight hemostat to establish a watertight seal. A second 2-0 silk tie was positioned over the parafilm adjacent to the stopcock to form another seal. A straight hemostat was then used to clamp the distal 2 mm of the PTFE/parafilm to seal this end.

Equal volumes of fibrinogen and thrombin solution prepared as described above were mixed and allowed to react for approximately 30 seconds which is when polymerization occurs. The thrombin-polymerized fibrin is then opaque. (This time factor is approximate and varies from one thrombin lot to another. The appropriate length of time to polymerization can be determined by viewing the opacity of the mixture). The fibrin/thrombin mixture was aspirated into a one cc syringe. (NOTE: The volume of this graft was 0.42 ml. For a graft with a larger volume one needs to use a larger syringe.) The syringe was attached to the stopcock and the mixture was injected by hand over a period of 5 seconds until the liquid was seen to "sweat" through the PTFE interstices and filled the space between the PTFE and the Parafilm™. The 3-way stopcock was closed to the PTFE graft for 3 minutes and a scalpel blade was used to cut the ligature at the end of the PTFE over the stopcock. The PTFE graft/parafilm was removed from the stopcock and a hemostat was used to remove the PTFE from the parafilm envelope. To clear residual growth factor-supplemented FG from the graft lumen, a number 3 embolectomy catheter was passed through the graft five times until the graft lumen was completely clear. The growth factor-supplemented FG-treated PTFE graft was allowed to dry overnight for about 12 hours under a laminar flow hood. The treated graft was then ready for implantation.

Alternatively, this HBGF-supplemented FG was pressure perfused into a 34 mm (24 mm+5 mm at each end)×4 mm (internal diameter) thin-walled, expanded PTFE graft thereby coating the graft's luminal surface and extending through the nodes to the graft's outer surfaces. The lumen of the graft was cleared as stated above. These grafts were then interposed into the infrarenal abdominal aortas of 24, 3–5 Kg New Zealand white rabbits. In the first study, the animals were sacrificed and specimens were explanted at 0 time (to correct for losses due to surgical manipulation) and after 5, 30, and 60 min, and 1, 7, 14, and 30 days. Residual radioactivity was determined by gamma counting. Remaining $^{125}$I-HBGF-1, corrected for spontaneous decay, is expressed as a percentage of the zero time value.

The washout of $^{125}$I-HBGF-1 followed classic kinetics with a rapid initial loss with the reestablishment of circulation (%/min=−24.1 between 5 and 60 minutes) followed by a slow loss after 1 hr (%/min=−0.03) with 13.4%+6.9% remaining after 1 week and 3.8%±1.1% remaining after 30 days.

B. In Vivo Endothelialization Study

The second study evaluated the effects of the applied HBGF-1-supplemented FG suspension on: the rate of endothelialization of widely expanded 60 μm internodal distance expanded PTFE grafts implanted into canine aorta-iliac positions; the proliferative activity of these endothelial cells as a function of time; and the relative contributions of the HBGF-1 and the FG in stimulating the observed endothelial cell proliferation. Three groups of 50×4 mm non-reinforced expanded PTFE grafts were implanted in the aortailiac position of 12 dogs. Group 1 (n=6) contained 20 μg/cm$^2$ heparin, 2.86 mg/cm$^2$ fibrinogen and 2.86×10$^{-2}$ U/cm$^2$ of human thrombin plus 1 ng/cm$^2$ of HBGF-1. Group 2 (n=3) contained the same FG without HBGF-1. Group 3 (n=3) consisted of identical but untreated control grafts. Tritiated thymidine (3H-TdR; 0.5 μCi/kg) was injected in 10 hours before explantation. Grafts were explanted at 7 and 28 days for light and electron microscopy, Factor VIII immunohistochemistry, and en face autoradiography for endothelial cell proliferation in random high power fields. Each graft was viewed by three observers who did not know from which treatment group the graft came. Differences in endothelial cell proliferation were statistically analyzed by two-way ANOVA and independent t-tests.

At 7 days 33% of both the FG and HBGF-1-supplemented FG grafts demonstrated non-contiguous foci of endothelial cells (FIG. 11). The surface of the control grafts remained a fibrin coagulum. At 28 days, every HBGF-1-supplemented FG showed extensive capillary ingrowth and confluent endothelialized blood contacting surfaces, which were not seen in any specimen of the other two groups (FIGS. 11 and 12). FIG. 12 demonstrates that untreated grafts at 28 days had few visible endothelial cells on their surface (Panel G). Grafts treated with FG alone had about 33% of their surface covered with endothelial cells indicating that FG treatment alone encouraged some reendothelialization (Panel H). However, grafts treated with FG supplemented with HBGF-1 (Panel I) appeared to be completely (>95%) covered with endothelial cells which display the characteristic cobblestone morphology of endothelial cells. Thus, the combination of growth factors delivered by FG was able to encourage essentially the complete covering of the vascular graft with a non-thrombogenic endothelial cell lining. En face autoradiography revealed a statistically significant increase (p<0.05) in $^3$H-TdR incorporation into the DNA of endothelial cells in the HBGF-1-supplemented FG grafts at 28 days vs. all other groups both as a function of time and of graft treatment.

These data demonstrate that pressure perfusion of an HBGF-1-supplemented FG suspension into 60 μ internodal distance expanded PTFE grafts promotes endothelialization via capillary ingrowth and increased endothelial cell proliferation.

These studies demonstrate enhanced spontaneous re-endothelialization of small diameter vascular grafts, and also a method for stimulating a more rapid confluence of transplanted endothelial cells.

EXAMPLE 9

Delivery of Tributyrin from Fibrin Sealant

The induction of endothelialization of artificial vascular grafts by FGF-1 delivered in fibrin sealant represents an important therapeutic application of the use of supplemented fibrin sealant as a delivery vehicle. Hyperproliferation of smooth muscle cells in arterial walls is a significant component of arteriosclerosis, and in restenosis following angioplasty (Cercek et al., *Amer. J. Cardiol.* 68:24C (1991)). Therefore, delivery of an anti-proliferative or differentiating agent suitable for intravascular treatment from a supplemented fibrin sealant delivery system was considered to prevent or treat this condition.

In choosing an agent to prevent smooth muscle cell hyperproliferation, a drug with extremely low toxicity was selected as it was important not to induce cell damage that might exacerbate the underlying condition. Butyric acid has been shown to prevent the hyperproliferation of retinoblastoma cells (Kyritsis et al., *Anticancer Res.* 6:465 (1986)), Swiss 3T3 cells (Toscani et al., *J. Biol. Chem.* 265:5722 (1990)) and other cell types (Prasad et al., *Life Sci.* 27:1351 (1980)) by inducing a differentiation program.

An induced prevention of hyperproliferation also has been achieved in smooth muscle cells by a related compound, tributyrin. This effect on smooth muscle cells requires a concentration of tributyrin that is close to saturation, making systemic therapy difficult. Therefore, the following experiment was conducted to demonstrate the efficacy of delivering tributyrin directly to the lesion from a supplemented fibrin sealant composition.

Tributyrin was mixed with thrombin, which was then mixed with fibrinogen to form a fibrin sealant matrix. The supplemented fibrin sealant was placed into 24-well culture plates. Culture medium (2 ml) was then placed in wells containing the tributyrin supplemented fibrin sealant, and these were incubated at 37° C. The medium from a new set of three wells was harvested daily, and the supernatant used to culture proliferating smooth muscle cells (10,000 rat or rabbit smooth muscle cells per well, which had been allowed to attach overnight). After incubation for two days (48 hours), the number of cells in each smooth muscle cell culture was measured using the MTS assay (a bioreduction of the tetrazolium compound MTS (Promega, Madison, Wis.) into a soluble formazan chromatophore detected by spectrophotometry at 490 nm.)

As shown in FIG. 13, the medium harvested from wells containing fibrin sealant alone supported the growth of the smooth muscle cells, while the medium from wells with fibrin sealant containing tributyrin significantly inhibited smooth muscle cell proliferation. As the number of days of tributyrin diffusion into the medium increased, the degree of inhibition increased. These results indicated that a cell regulatory drug, tributyrin, can be delivered from fibrin sealant for extended periods and that it retains the sustained ability to inhibit the proliferation of a specific cell type.

EXAMPLE 10

Formulation and Delivery of TGF-β2 from Fibrin Sealant

Fibrinogen and thrombin were prepared per instruction of the American Red Cross, Rockville, Md. Upon reconstitution, the protein concentration of the Topical Fibrinogen Complex, (TFC) was 120 mg/ml (the standard formulation for hemostasis). The human thrombin was reconstituted with 40 mM $CaCl_2$ to yield a solution at 300 units/ml.

To evaluate the compatibility of transforming growth factor β2 (TGF-P2) in Topical Fibrinogen Complex, TGF-β2 (purified recombinant human protein provided by Genzyme Corp., Framingham, Mass.) was spiked into TFC at 10 and 1 μg/ml. Samples were incubated for two weeks at 2–8° C. TGF-β2 was extracted for analysis by passing the gel-like material through a narrow bore stopcock connected to two syringes. The ELISA data indicated full recovery of TGF-β2 from the TFC. Analysis in the in vitro bio-assay indicated that the extract was bioactive.

TGF-β2 was then spiked into the TFC solution at a concentration of 1 μg/ml or 100 ng/ml. 50 μl aliquots were placed into sterile test tubes and 50 μl of the thrombin solution was added to form the fibrin clot. Clot formation occurred within a few seconds. These samples were allowed to sit overnight at 2–8° C. Test sample tubes were then overlaid with 400 μl of PBS/0.1% human serum albumin pH 7.0, with or without 10 μg/ml plasmin. The test samples were incubated for two days at 37° C. to evaluate the release and recovery of the TGF-β2. Complete resolution of the clot was observed in the plasmin treated samples. The clot remained intact in the non-plasmin treated samples. The diffusion supernatant was analyzed by ELISA. The data are summarized in Table 1.

TABLE 1

| TGF-β2 Concentration in Fibrin Clot | % Recovery in Diffusion Supernatant (by ELISA) | |
|---|---|---|
| | With Plasmin | Without Plasmin |
| 500 ng/ml | 100% | 2.5% |
| 50 ng/ml | 100% | (not detectable) |

Theoretical concentrations of components in the final clot based on dilution:

TFC protein=60 mg/ml; thrombin activity=150 units/ml; TGF-β2=500 ng/ml or 50 ng/ml.

The data indicate not only that TGF-β2 is stable in TFC, but that the delivery of TGF-β2 from fibrin sealant by diffusion can be sustained in low amounts. Moreover, the release of TGF-β2 from fibrin sealant requires dissolution of the fibrin clot by plasmin indicating that in vivo delivery of TGF-β2 from the supplemented tissue sealant composition would be mediated by resolution of the fibrin clot. Thus, the mechanism of delivery from the TGF-β2 supplemented tissue sealant composition is readily distinguished from simple diffusion kinetics.

EXAMPLE 11

The Preparation of a Platelet-Derived Extract for Use with FG

Plasma reduced platelets were prepared and pelleted. The supernatant plasma was removed. The pelleted platelets were washed, suspended in buffer containing 50 mM histidine and 0.15 M sodium chloride at pH 6.5, and treated with bovine thrombin. After treatment, the supernatant was collected by centrifugation and aliquots were frozen at −80° C. The extract was thawed and mixed with FG or other TSs.

The platelet extract obtained in this manner was biologically active since it increased the incorporation of radioactive labeled thymidine into the DNA of proliferating NIH3T3 fibroblasts compared to the controls.

To evaluate the effect of platelet extract on wound healing, experiments identical to those carried out below in Example 12 with HBGF-1β were carried out with platelet extract in diabetic mice. From the results of these experiments is clear that, given the low concentration of growth factors in the platelet extract, a dose larger than 100 μg of platelet extract protein per wound needs to be used to promote wound healing.

EXAMPLE 12

The Effect of FG on Skin Wound Healing in Vivo

A. Unsupplemented FG

Animals

Female C57BL/$K_S$J-db/db mice were obtained from Jackson Laboratories (Bar Harbor, Me.) and were 8 to 12 weeks old at the start of the experiment. They were housed in separate cages after surgery in an animal care facility.

These mice are used as a model of impaired wound healing in diabetic humans because the metabolic abnormalities seen in these mice are similar to those found in human diabetics. In addition, the healing impairment characterized by markedly delayed cellular infiltration, granulation tissue formation, and time required for wound closure suggest that healing in this mouse model may be relevant to the healing impairment seen in human diabetes.

Fibrin Sealant

The concentrated topical fibrinogen complex (TFC) used in this study was produced from fresh frozen pooled human plasma. The TFC product (American Red Cross—Baxter Hyland Division, Los Angeles, Calif.) was supplied in lyophilized form. After reconstitution with 3.3 ml of sterile water, the protein characteristics of the TFC solution used in this study were: total protein, 120 mg/ml; fibrinogen, 90 mg/ml; fibronectin, 13.5 mg/ml; Factor XIII, 17 U/ml; and plasminogen, 2.2 μg/ml.

Topical bovine thrombin (5000-unit vial, Armour Pharmaceutical Co., Kankakee, IL) was reconstituted with 5 ml sterile water and was serially diluted in 80 mM calcium chloride solution (American Reagent Laboratories, Shirley, N.Y.) to a concentration of 15 U/ml.

Equal volumes of TFC and reconstituted thrombin were mixed to produce FG. In order to fill a round 6-mm-diameter full thickness wound, 0.015 ml of TFC was mixed with 0.015 ml of thrombin. The FG that was produced had a protein concentration of approximately 60 mg/ml.

A diluted FG with a protein concentration of approximately 1 mg/ml was also used.

Surgery

The mice were anesthetized with a mixture consisting of 7 ml ketamine hydrochloride (100 mg/ml; Ketaset, Aveco Co., Inc., Fort Dodge, Iowa), 3 ml xylazine (20 mg/ml; Rompun, Mobey Corp., Shawnee, Kans.), and 20 ml physiological saline, at a dose of 0.1 ml per 100 g body wt, administered intramuscularly. The dorsal hair was clipped, and the skin was washed with povidone-iodine solution and wiped with 70% alcohol solution. Two full-thickness, round surgical wounds (6 mm diameter) were made on the lower back of the mouse, one on each side, equidistant from the midline. The medial edges of the two wounds were separated by a margin of at least 1.5 cm of unwounded skin.

Immediately after the wounding had been performed, FG and/or a dressing was placed over the designated wound. The dressing was a transparent semipermeable adhesive polyurethane dressing (Opsite™, Smith and Nephew, Massillon, Ohio). Tincture of Benzoin compound (Paddock Laboratories, Minneapolis, Minn.) was applied at the periphery of the wound area prior to application of the dressing. There was a margin of at least 0.5 cm of skin surrounding the wound edge over which no tincture of benzoin was applied to avoid the possible inflammatory effects of benzoin on the raw wound. No further treatments were applied to the wound for the duration of the experiment.

Treatment Groups

The mice were divided into 4 treatment groups, with each mouse serving as its own control:

Group I: The wound on one side of the animal was treated with FG (60 mg/ml) while the contralateral wound received no treatment. Both wounds were covered with Opsite™.

Group II: Diluted FG (1.0 mg/ml) was topically applied to the wound on one side while the contralateral wound received no treatment. Both wounds were covered with Opsite™.

Group III: FG (60 mg/ml) was topically applied over both wounds. The wound on one side was left uncovered while the contralateral wound was covered with Opsite™.

Group IV: No topical treatment was applied over the wounds. The wound on one side of the animal was left uncovered while the wound on the contralateral side was covered with Opsite™.

Wound Analysis

The animals were euthanized on Day 9 of the experiment. The wounds were excised down to the muscle layer, including a margin of 0.5 mm of unwounded skin, and were placed in buffered 10% formalin solution. The specimens were submitted to a histology laboratory for processing. Specimens were embedded in paraffin, and the midportion of the wound was cut in 5-μm sections. The slides were stained with hematoxylin and eosin, or with Masson's trichrome for histologic analysis.

Each slide was given a histological score ranging from 1 to 15, with 1 corresponding to no healing and 15 corresponding to a scar with organized collagen fibers (Table 2). The scoring scale was based on scales used by previous investigators. The criteria used previously were modified and were further defined to more precisely reflect the extent of: reepithelialization, degree of cellular invasion, granulation tissue formation, collagen deposition, vascularity, and wound contraction. The histologic score was assigned separately by at least three analysts. The code describing the wound treatment was broken after the scoring was completed by all observers.

TABLE 2

Criteria for Scoring of Histologic Sections

| Score | | Criteria |
|---|---|---|
| 1–3 | Epithelialization | None to very minimal |
| | Cellular content | None to very minimal (mainly inflammatory cells) |
| | Granulation tissue | None to sparse amount at wound edges |
| | Collagen deposition | None |
| | Vascularity | None |
| 4–6 | Epithelialization | Minimal (less than half of wound diameter) to moderate (more than half of wound diameter) |
| | Cellular content | Predominantly inflammatory cells, few fibroblasts |
| | Granulation tissue | None to thin layer at wound center, thicker at wound edges |
| | Collagen deposition | Few collagen fibers |
| | Vascularity | Few capillaries |
| 7–9 | Epithelialization | Completely epithelialized; thin layer |
| | Cellular content | More fibroblasts, still with inflammatory cells |
| | Granulation tissue | 7, sparse at wound center, mainly adipose tissue underneath epithelium |
| | | 8, thin layer at wound center; few collagen fibers |
| | | 9, thicker layer; more collagen |
| 10–12 | Epithelialization | Thicker epithelial layer |
| | Cellular content | Predominantly fibroblasts |
| | Granulation tissue | Uniformly thick |
| | Collagen deposition | Moderate to extensive collagen deposited, but less mature when compared to collagen of unwounded skin margin |
| | Vascularity | Moderate to extensive neovascularization |
| 13–15 | Epithelialization | Thick epithelium |
| | Cellular content | Fewer number of fibroblasts in dermis |
| | Granulation tissue | Uniformly thick |
| | | Dense, organized, oriented collagen fibers |
| | | Few well-defined capillary systems |

(Continued on next page)

Statistical Analysis

The values of the histological scores of the analysts were averaged and were expressed as the mean ±standard error of the mean.

The paired t test was used for comparison of paired means in the different treatment groups. The analyses were performed using the RS/1 Release 3.0 statistical software package (BBN Software Products Corporation).

The sample mean differences were tested for analysis of variance using the Statistical Analysis Software (SAS) System.

Results

The Effect of FG on Wound Closure (Group I)

In Group I both wounds on each mouse were covered with Opsite™. Under these conditions, the topical application of FG with a protein concentration of 60 mg/ml to only one side of the animal resulted in statistically lower mean histological scores (3.06) for the FG side compared to the untreated wounds (5.26) (P<0.005) (Table 3).

TABLE 3

The Effect of FG (60 mg/ml)
on Wound Closure (Group I)

| Treatment | Histologic score | N |
|---|---|---|
| FG + Opsite ™ | 3.06 ± 0.7 | 15 |
| Opsite ™ alone | 5.26 ± 2.21 | 15 |

The Effect of Dilute FG on Wound Closure (Group II)

In this group, both paired wounds which were covered with Opsite™, topical application of dilute FG (protein concentration of 1 mg/ml) resulted in a mean histological score (4.0) that was not statistically different from that for untreated wounds (4.36) ($P=0.17$) (Table 4).

TABLE 4

The Effect of Dilute FG (1 mg/ml)
on Wound Closure (Group II)

| Treatment | Histologic score | N |
|---|---|---|
| Dilute FG + Opsite ™ | 4.00 ± 0.77 | 11 |
| Opsite ™ alone | 4.36 ± 0.67 | 11 |

The Effect of Opsite™ on FG-Treated Wounds (Group III)

In this group of paired wounds both treated with FG with a protein concentration of 60 mg/ml, the application of Opsite™ to one side resulted in a mean histological score (4.2) which was not statistically different from that for wounds which were left uncovered (4.93) ($P=0.11$) (Table 5).

TABLE 5

The Effect of Opsite ™ on Paired Wounds
Treated with FG (Group III)

| Treatment | Histologic score | N |
|---|---|---|
| Opsite ™ + FG | 4.20 ± 1.93 | 15 |
| FG but no Opsite ™ | 4.93 ± 1.09 | 15 |

Effect of Opsite™ on the Closure of Paired Untreated Wounds (Group IV)

In this group of paired wounds which did not receive topical treatment of FG, application of Opsite™ to one side resulted in a significantly lower mean histological score (4.92), as compared to that for wounds which were left uncovered (6.31) ($P<0.0005$) (Table 6).

ANOVA of the treatment effects on sample mean differences was significant at <0.0001.

TABLE 6

The Effect of Opsite ™ on the Closure of Paired
Untreated Open Wounds (Group IV)

| Treatment | Histologic score | N |
|---|---|---|
| Opsite ™ (no FG) | 4.92 ± 1.26 | 13 |
| No Opsite ™ (no FG) | 6.31 ± 1.25 | 13 |

Discussion

The results of this study indicated that in mice (1) when applied over open wounds, FG at a concentration formulated for hemostasis (60 mg/ml) resulted in lower histological scores at Day 9 which indicated slower rates of wound healing compared to that of untreated wounds; (2) dilution of the FG protein concentration to 1 mg/ml resulted in a higher histological score at Day 9 which indicated a faster rate of wound healing; and (3) application of a semipermeable dressing (Opsite™) per se significantly retarded wound closure in this animal model by itself.

The total protein concentration of FG is an important variable when comparing the results of studies using FG. Beneficial effects of fibrin in promoting wound healing and tissue repair have been reported, but lower concentrations of fibrinogen have been used in the present studies than is commonly found in commercial preparations.

FG at a concentration of 60 mg/ml delayed wound closure (Group I). The total protein concentration of FG which is commercially available in Europe, after mixture of the fibrinogen and thrombin components, is 37.5 to 57.5 mg/ml. These data indicate that FG as presently formulated for hemostatic and adhesive indications retards healing when applied to open skin wounds. This effect may be due to (1) mechanical obstruction to the migration or proliferation of cellular elements that actively participate in the wound healing process, (2) mechanical inhibition of wound contraction or (3) a chemical inhibitory effect of one or more FG components on wound healing. Mechanical obstruction and inhibition of wound closure may be the more likely explanation, since at Day 9 there is persistence of a solid fibrinogen-based clot on the wound surface.

In order to help determine if this was the cause, the total protein concentration of FG was diluted to 1 mg/ml. Topical application of this dilute FG resulted in a histological score that was not significantly different from that for untreated wounds (Group II), suggesting that lower total protein concentrations do not significantly inhibit the wound healing process.

It is also worth noting that the mean histological score for covered wounds treated with the same concentration of FG (60 mg/ml) but belonging to different treatment groups (Groups I and III) had significantly different values (3.06 for Group I vs. 4.2 for Group III). These data demonstrated that animal to animal variation makes it difficult to derive definitive conclusions from different animals subjected to the same treatment variables because some animals may heal faster or slower than the others despite receiving the same treatment. This is reflected in the range of standard errors for the mean scores. For this reason each animal served as its own control, e.g. wounds in the same animal were compared to each other. By having the control wounds in the same animal as the test wounds, the effects of interanimal variability was minimized. These data also show that an adhesive dressing such as Opsite™ significantly delayed wound closure. It should be noted, however, that in partial thickness skin wounds in pigs the protein concentration of the FG does not appear to be related to the rate of wound healing.

B. Growth Factor-Supplemented FG on Wound Healing In Vivo.

The effect of HBGF-1 B growth factor-supplemented FG on the rate of wound repair in diabetic mice was assessed. The methods used in this experiment were similar to those just described above. Two 6 mm full-thickness skin biopsies on the dorsal part of each of 6 test mice were filled with FG to which 5 μg of HBGF-1β had been added. Identical biopsies in six mice were left untreated, and in six control mice were filled with unsupplemented FG. After 9 days, all of the mice were sacrificed and histological preparations of 5 micron thick slices from each of the wounds and surrounding skin were prepared and stained with hematoxylin and eosin.

The extent of wound repair in each sample, which was not identified as to the treatment group from which it came, was "blindly" evaluated by each of three trained analysts, who assessed collagen deposition, reepithelialization, thickness of the granulation tissue and the density of inflammatory cells, fibroblasts and capillaries. Each sample was scored from 1 to 15, ranging from no to complete repair. The samples from the wounds treated with unsupplemented FG were consistently given the lowest scores and those from the untreated wounds or wounds treated with the growth factor-supplemented FG were given the highest scores.

EXAMPLE 13

FG as a Delivery Vehicle of Osteoinductive Substances In Vivo

Fibrin Sealant

Concentrated human TFC (Baxter Hyland Division, San Pedro, Calif.) and human thrombin (Baxter Hyland Division, Glendale, Calif.) were produced for the American Red Cross from screened fresh frozen pooled human plasma. Both components underwent viral inactivation using the solvent detergent method (New York Blood Center) during their production and were supplied in lyophilized form. After reconstitution with 3.3 ml of sterile water, the protein characteristics of the TFC solution were: total protein=120 mg/ml; fibrinogen=90 mg/ml; fibronectin=13.5 mg/ml; Factor XIII=17 U/ml; and plasminogen=2.2 μg/ml.

Human thrombin (1000 U vial) was reconstituted with 3.3 ml sterile water, and was serially diluted in 40 mM calcium chloride solution (American Regent Laboratories, Shirley, N.Y.) to a concentration of 15 U/ml. Human thrombin was used for preparing disks implanted which were onto calvarial defects.

Topical bovine thrombin (5000 U vial, Armour Pharmaceutical Co., Kankakee, Ill.) was reconstituted with 5 ml sterile water, and was serially diluted in 40 mM calcium chloride solution to a concentration of 15 U/ml. Bovine thrombin was used for preparing implants for intramuscular bioassay.

In practicing this embodiment of this invention the fibrinogen should be present at a concentration of 1 to 120 mg/ml FG, more preferably from 3 to 60 mg/ml FG, most preferably from 10 to 30 mg/ml FG. DBM should be present at an approximate concentration of about 1 to 1000 mg/ml FG, more preferably from 50 to 500 mg/ml FG, most preferably from 300–500 mg/ml FG. The particle size of demineralized bone powder should be from 0.01 to 1000 microns, preferably from 20–500 microns and most preferably from 70–250 microns. The osteoinductive growth factor(s) or BMPs should be present at a concentration(s) of about 1 to 100 μg/ml wherein the concentration(s) is effective to accomplish its desired purpose. Growth factors which may be used as osteoinductive substances in this embodiment include, but are not limited to: osteogenin (BMP3); BMP-2; OP-1; HBGF-1; HBGF-2; BMP 2A, 2B and 7; FGF-1; FGF-4; and TGF-β. In addition, drugs, such as antibiotics, can be used to supplement the TS for use in bone repair.

Implant Preparation

Rat DBM was prepared as follows. The epiphyses of the long bones of rats were removed leaving only the diaphyses behind. The diaphyses were split, if necessary, and the bone marrow was then thoroughly flushed with deionized water (Milli-Q Water Purification System™, Millipore Corporation, Bedford, Mass.). The diaphyses were then washed at room temperature. At 4° C., 1000 mls of deionized water was added to 100 g of bone. The mixture was stirred for 30 minutes and the water was decanted. This step was repeated for two hours.

At 4° C., one liter of cold absolute ethanol (Quantum Chemical Corporation, U.S.I. Division, Tuscola, IL) was added for every 100 g of bone. After stirring for 15 minutes, the ethanol was decanted. This was repeated four times for a total of one hour's duration.

Under a fume hood, 500 ml of diethyl ether (Mallinckrodt Speciality Chemicals, Paris, Ky.) was added to the bone to cover it. This was stirred gently for 15 minutes and the ether was then decanted. An additional 500 mls of ether was added to the bone and the mixture was stirred for 15 minutes. The ether was again decanted. The bone was left under the fume hood for the evaporation of the ether to occur. Defatted bone can be stored indefinitely in an ultralow freezer (−135° C.).

The bone was then milled to make bone powder. The powder was sieved and 74 to 420 micron size particles were collected.

Ten gram aliquots of the bone powder were placed in 250 ml centrifuge bottles. Eighty mls of 0.5 N HCl was added to each bottle slowly in order to avoid frothing. The contents of each bottle were then stirred gently. After 15 minutes, an additional 100 mls more of 0.5 N HCl was added to each bottle over the course of 10 minutes. The bottles were then stirred gently for an additional 35 minutes. The total time that the powder was in the HCl did not exceed one hour.

Each mixture was then spun in a centrifuge at 3000 rpm at 4° C. for 15 minutes. The pH of the supernatant was then checked. If the pH was greater than 2, the supernatant was poured down a chemical sink without disturbing the pellet(s). If the pH of the supernatant was less than 2, the supernatant was poured off into a hazardous waste container. If the pellet(s) were loose, the centrifuge time was increased to 30 minutes. These steps were repeated until the pH of the supernatant was equal to 0.5 N HCl.

The pellets were then washed with 180 mls of deionized water by stirring to produce an even suspension. The suspension was then centrifuged for an additional 15 minutes. The supernatant was then decanted as before. The washing was repeated until the pH of the supernatant equaled the pH of the deionized water.

The pellets were then frozen at −180° C. in a freezer. They were then lyophilized using standard procedures.

Disk-shaped implants 1 mm thick and 8 mm in diameter were produced using a 4-piece aluminum mold (FIG. 14). Twenty-five mg of rat DBM powder was added into the mold chamber. Thirty μl of TFC was then pipetted onto the DBM and mixed until the DBM had absorbed all of the solution. The concentrations of TFC which were used were 10, 20, 40, 80, or 120 mg/ml. Thirty μl of thrombin solution (15 U/ml in 40 mM calcium chloride solution) was then added to the DBM-TFC complex, was mixed, and was compressed into a disk-shape using a piston-shaped lid. It was determined that 25 mg of DBM powder had a volume of 20 µl. After DBM had been added to the FG, the final protein concentrations were as follows:

TABLE 7

| TFC (mg/ml) | Thrombin (µ/ml) | DBM (mg) | FG, Total protein conc. (mg/ml) |
|---|---|---|---|
| 120 | 15 | 25 | 45 |
| 80 | 15 | 25 | 30 |
| 40 | 15 | 25 | 15 |
| 20 | 15 | 25 | 8 |
| 10 | 15 | 25 | 4 |

Disk implants composed of DBM alone or FG alone (4, 8, 15 and 45 mg/ml total protein concentrations) were likewise made using the same mold.

Fifty mg of DBM was poured into an aluminum mold, to which 60 µL of TFC was then added to the DBM and mixed until fully absorbed. Sixty µl of thrombin was then added to the DBM-TFC complex, mixed and compressed into a disk-shape with a diameter of 1 cm and a thickness of 2 mm using a piston-shaped lid. The disk was then cut manually into the desired shape (triangle, square or donut).

For the intramuscular bioassay experiment, implants were placed in a sterile nylon bag having a mesh size of 70 microns and measuring 1 cm×1 cm.

Animals

Male Long-Evans rats were obtained from Charles River Laboratories (Wilmington, Mass.). For the intramuscular bioassay, 28 to 35 day old rats were used. Three month old rats were used for the craniotomy experiment.

Surgery

The animals were anesthetized with a mixture consisting of 10 ml ketamine hydrochloride (Vetalar, 100 mg/ml, Parke-Davis, Morris Plains, N.J.), 5 ml xylazine (Rompun, 20 mg/ml, Mobay Corporation, Shawnee, KN), and 1 ml physiologic saline (0.9% NaCl), at a dose of 0.1 ml per 100 gm body weight, administered intramuscularly. The operative site of the animal was prepped with 70% alcohol solution, followed by povidone-iodine solution. The surgical procedure was then performed using aseptic technique.

Intramuscular Bioassay. A midline ventral incision was made and a space was created between the pectoralis muscles with blunt dissection. A nylon envelope containing the designated experimental material was inserted into the intramuscular space and secured with a 3-0 Dexon suture (FIG. 15). The same procedure was then repeated at the contralateral side. The skin was then closed with staples. The implants were harvested after four weeks, were x-rayed and were prepared for histology.

Disk-shaped implants were placed randomly and consisted of the following: DBM alone (n=12); FG alone at different concentrations (4 mg/ml, n=14; 8 mg/ml, n=3; 15 mg/ml, n=3; and 45 mg/ml, n=12), and DBM-FG complex (4 mg/ml, n=12; 8 mg/ml, n=12; 15 mg/ml, n=12; and 45 mg/ml, n=12). There were four each of the square-, triangle- and donut-shaped implants.

Craniotomy Procedure. A linear incision was made from the nasal bone to the mid-sagittal crest. Soft tissues were reflected gently and the periosteum was dissected from the craniotomy site (occipital, frontal, parietal bones). An 8-mm craniotomy was prepared with a trephine in a slow-speed rotary handpiece using copious saline irrigation as needed. The calvarial disk was dissected free while avoiding dural perforations and superior sagittal sinus intrusion. The 8-mm calvarial defect was either left untreated as control or filled with a 1×8-mm DBM or DBM-FG disk (FIG. 16). The skin was then closed with skin staples.

Following surgery, each rat was identified by ear punches and returned to its cage where they were ambulatory within 2–3 hours.

The first set of calvarial implants consisted of DBM alone (25 mg, n=3) or DBM in a FG matrix (15 mg/ml, n=2; 30 mg/ml, n=3; and 45 mg/ml, n=3), and were retrieved after 28 days. The second set of calvarial implants consisted of 25 mg DBM in a 30 mg/ml FG matrix and were retrieved at different postoperative times (28 days, n=10; 3 months, n=9; and 4 months, n=5).

Retrieval of Implants

At the indicated times, the rats were euthanized in a carbon dioxide chamber. A skin incision was made around the experimental recipient bed (i.e., pectoralis major or calvaria) and the soft tissues were reflected from the recipient beds. In orthotopic sites, the craniotomies with 3–4 mm contiguous bone were recovered from the fronto-occipito-parietal complex. In heterotopic sites, sharp and blunt dissection was used to recover the implanted nylon envelopes.

Radiography

The implants were radiographed using X-OMATL™ high contrast Kodak x-ray film (Eastman Kodak Company, Rochester, N.Y.) in a Minishot Benchtop Cabinet x-ray system (TFI Corporation, West Haven, Conn.) at 30 kvp, 3 Ma, and 10 seconds. Gray-level densities of intramuscular and craniotomy site radiographs were analyzed using a Cambridge 920 Image Analysis System™ (Cambridge Instruments Limited, Cambridge, England).

Histological Analysis

All retrieved specimens (soft and hard tissues) were immediately placed into appropriately labeled vials containing preservative solution and were submitted to a histology laboratory for processing. Histologic specimens were 4.5 micrometer-thick sections through the coronal diameter. For each recipient site, one section was prepared with hematoxylin and eosin stain (for photomicrography and examination of cell and stromal detail) and the other section was prepared with a von Kossa stain.

Results

Radiography of Intramuscular Plants

All DBM disks displayed radio-opaque images. Forty-five out of 48 implanted DBM-FG disks (93.75%) were radio-opaque. All DBM-FG disks, regardless of protein concentration (4–45 mg/ml) induced radio-opacity (FIG. 17). Radio-opacity measurements of some DBM disks (FIG. 17) were higher than DBM-FG disks but the other measurements were well within the range of measurements for DBM-FG disks. Thirty out of 32 FG disks which were not supplemented with DBM (93.75%) did not develop radio-opacity.

DBM-FG disks in the form of squares, triangles or donuts were also markedly radio-opaque as compared to FG disks which were not supplemented with DBM. The original shapes of the implants were generally retained.

Histology of Intramuscular Implants

The intramuscular bioassay was positive for DBM and DBM-FG implants, as evidenced by formation of ossicles with a central cavity filled with marrow and resorption of previously implanted DBM particles.

Radiography of Calvarial Implants

X-rays showed DBM implants in a FG matrix to be generally more radio-opaque than DBM implants alone or untreated controls. There was no marked discernible difference between different concentrations of FG used to deliver DBM. The radiographs of untreated 8-mm diameter calvaria defects showed a negligible amount of radio-opacity.

The second set of calvarial implants using DBM in 30 mg/ml FG matrix showed markedly increased radio-opacity within the craniotomy wounds of 3 or 4 month-old calvaria over 28 day calvaria (FIG. 18).

Histology of Calvarial Implants

Non-treated 8 mm craniotomy wounds showed only fibrous connective tissue developing across the craniotomy wound (FIGS. 19A and B). Histology of DBM implants showed DBM particles to be scattered all over the field. Some DBM particles migrated over and under the edges of host bone (FIG. 20). Most DBM particles were, however, within the confines of the craniotomy wound and were surrounded by loose connective tissue that was well vascularized. Active resorption of DBM by osteoclasts was noted. A lot of DBM particles were also noted to be populated by live cells. New osteoid and bone laid down by osteoblasts were quite evident.

The histology of DBM implants in a FG matrix showed DBM particles localized within the craniotomy wound, surrounded by much denser and more cellular connective tissue (FIGS. 19 and 20). Osteoid matrix and bony trabeculae formation were quite evident. More bone marrow was noted to have formed in craniotomy wounds implanted with DBM-FG disks than with DBM implants alone. There was also greater neovascularization with DBM-FG disks than with DBM implants alone or untreated controls. Osteoregeneration was evident at all concentrations of FG used to deliver DBM.

Discussion

The natural biocompatibility and biodegradability of FG are characteristics that make it an ideal delivery vehicle for DBM and BMPs. FG facilitated the shaping of DBM into the desired form to fill bony defects, maintained DBM within the defect, and may have been synergistic with DBM. Furthermore, soft tissue prolapse did not occur and bony contour was maintained. DBM-supplemented FG possessed an appropriate microarchitecture, biodegradation profile and release kinetics to support osteoblast recruitment and osteoregeneration.

Overall, the data indicated that DBM delivered in FG at any of the tested FG protein concentrations induced as much bone formation as the DBM did alone. Moreover, when DBM was configured with FG to a particular pre-operative form, the induced bone closely retained the original shape postoperatively.

Since the shape of the DBM-FG matrix determined the morphology of the newly formed bone, when possible, the DBM-FG matrix should be made of a predetermined shape. However, the DBM-FG matrix in liquid form can be delivered or injected into an irregularly shaped defect where it will polymerize and encourage bone formation in the DBM-FG-filled area.

EXAMPLE 14

The Release of Antibiotics (AB) From FG and Increased Longevity of the AB-Supplemented FG A. Preparation of the AB-FG 1. TET Free Base Three-and-one-half ml of water for injection was injected into a vial of lyophilized human topical fibrinogen concentrate (TFC), supplied by The American Red Cross. The protein concentration of the resulting solution was approximately 120 mg/ml.

Freeze-dried thrombin concentrate, supplied by The American Red Cross/Baxter-Hyland, Inc., Glendale, Calif., was reconstituted with 3.5 ml of a 40 mM solution of calcium chloride prepared in water for injection. The resulting solution contained approximately 250 U/ml.

TET-FG was formulated by mixing the desired weight of TET with 1 ml of reconstituted TFC solution and with 1 ml of reconstituted thrombin solution in the presence of injection quality calcium chloride (purchased from American Reagent, Shirley, N.Y.). The TET was in the free base form and was purchased from Sigma Chemical Company (St. Louis, Mo.). The TET-FG was formed by mixing TFC and thrombin through a Duoflo™ dispenser (Hamaedics, Calif.) onto a Millipore membrane in a 12 mm diameter Millipore culture plate (Millipore Corporation, Bedford, Mass.). The mixture was allowed to set for one hour at 22° C. Six mm diameter disks containing the TET-FG and the Millipore membrane were cut from the latter using a 6 mm punch biopsy. The TET-FG-containing disks were used for the TET release studies.

The release of TET from the TET-FG into phosphate buffered saline (PBS) or saliva was measured using 24-well cell culture plates (Corning Glass Works, Corning, N.Y.) under two different sets of conditions. In one condition, the static mode, 2 ml of PBS or 0.75 ml of saliva was replaced daily in the 24-well cell culture plates. In the other condition, the continuous exchange mode, TET release from the TET-FG was measured with PBS having been exchanged at a rate of approximately 3 ml per day. The samples were stored at −20° C. until analyzed. The saliva had been collected from 10 different people, had been pooled, and clarified by centrifugation at 5000 g. It was then filtered through a 0.45 µm pore sized membrane and was stored at 4° C. for daily use.

In order to measure the concentration and biological activity of the TET which had been released from the TET-FG disks, the eluted TET was thawed and was analyzed spectrophotometrically at 320 nm and/or biologically by the inhibition of *E. coli* growth on agar plates. To calibrate these assays, standard curves covering TET concentrations of from 0 to 50 and 0 to 500 µg/ml, respectively, were used.

2. Ciprofloxacin HCl (CIP)-, Amoxicillin (AMO)- and Metronidazole (MET) Supplemented FG.

FG containing CIP HCl, AMO or MET were prepared as before for TET. To monitor the release of these AB from the corresponding AB-FG into the immediate environment, the AB-FG disks were placed in individual wells in a 24-well cell culture plate and were covered with 2 ml of PBS that was collected, replaced daily and stored at −20° C. as before, until analyzed. The concentrations of CIP, AMO and MET in the eluates were measured spectrophotometrically at 275, 274 and 320 nm, respectively, and were compared to standard curves containing 0 to 50 ug/ml of the corresponding AB.

B. Structural Integrity of AB-FG

The maintenance of the structural integrity of the FG and the TET-FG disks was estimated by visual observation and physical inspection by "poking" the disks with a fine spatula. The porous membrane which had been cut out while making the disks remained attached to the TET-FG and was used to help position the disks during the evaluation of their structural integrity. Pictures of top and lateral views of the disks were also taken and were used in the evaluation.

The structural integrity of FG and TET-FG were measured under both sterile and non-sterile conditions. For the non-sterile experiments, the PBS and saliva were stored frozen until analyzed. For the sterile experiments, the same procedure was used except that the entire process was run under sterile conditions. The sterility of the system was tested by incubating 0.2 ml of sample and 2 ml of broth at 37° C. and the turbidity of the broth was monitored for 48 hours. Lack of turbidity indicated sterility of the system. The stability of the CIP-, AMO-, and MET-FG were studied as above but under non-sterile conditions only.

C. In Vitro Antimicrobial Activity of AB Released from AB-FG

The antimicrobial activity of the AB released from the AB-FG was estimated by measuring the diameters of the zones of inhibition generated by the eluate from the 6 mm diameter disks from the daily collected PBS or saliva surrounding the AB-FG. The eluates from unsupplemented FG served as controls. AB solutions of known concentration were used as standards. *E. coli* cultured on agar plates were used to measure the AB activity of the released TET, CIP and MET. To make the culture plates, 100 µl of the bacterial cell suspension, containing approximately $10^8$ cells/ml, was mixed with 3 ml of top agar at 50° C. and immediately poured onto the plate hard, bottom agar to make a uniform layer of cells. The plates were incubated at 37° C. for 18 hours.

Results

A. TET

1. TET Release Data

The release of TET from TET-FG disks into the surrounding PBS in the "static" experiments was measured spectrophotometrically by determining the TET concentration achieved in the 2 ml of PBS which was replaced daily. The TET concentrations which were obtained for different amounts of TET that had been incorporated into TET-FG are shown in FIG. 23. At TET concentrations in the TET-FG of less than 50 mg/ml, the release of TET was completed in five days or less. However, the release of TET from TET-FG disks which contained TET concentrations of 100 and 200 mg/ml occurred for approximately two weeks, and more than three weeks, respectively. The structural integrity of the TET-FG disks was preserved for three to five weeks. These results demonstrated that the TET release was independent of the FG degradation and that the rate of TET release depended on the amount of TET which remained in the TET-FG disks.

The spectrophotometric data which were collected in the continuous exchange experiment are shown in FIG. 24. These data indicate that a continuous TET release from a TET-FG disk which originally contained a TET concentration of 100 mg/ml FG occurred over a two week period. The FG disk retained its structural integrity during this two week period, infra. The TET release data obtained in the continuous mode experiment also indicated that the rate of TET release opportunity depended on the concentration of TET which remained in the TET-FG disk.

While not wishing to be bound by theory, it is believed that the initial high TET concentrations observed in these experiments were probably a consequence of the diffusion of TET from at or near the disk's surface. That is, as the TET "trapped" at these locations was exhausted, the rate of solubilization and/or diffusion decreased in a fashion that was most probably determined by the TET concentration gradient and by the shape or configuration of the FG.

Temperature and FG protein concentration also played a role in determining the TET diffusion rate from the TET-FG disks (see Examples 13 and 14), but these two parameters were kept constant in these experiments.

The release of TET into saliva from TET-FG containing 50 and 100 mg/ml of TET was measured in static experiments by determining the TET concentration in 0.75 ml of saliva that was replaced daily. These results (FIG. 25) are similar to those obtained in PBS except that the concentration of TET was higher, most probably reflecting the smaller volume of saliva which was used to collect the released TET. In addition, the presence of TET in the FG matrix again unexpectedly prolonged the structural integrity of the TET-FG matrices for at least 15 days compared to that for the control FG disks which had begun to decay by 9 days and were almost completely decayed by 15 days (FIG. 26).

2. TET Antimicrobial Data

The antimicrobial effects on *E. coli* growth of several TET concentrations in PBS are shown in FIG. 27. The lowest TET concentration detectable by this method was approximately 5 µg/ml. These results clearly indicate that the released TET has antimicrobial activity. These TET data corroborate those obtained by spectrophotometry and indicate that the amount of TET incorporated into the FG determines the TET concentration in the solution surrounding the TET-FG. These data also demonstrate that the amount of TET in the FG can be tailored to maintain the desired TET concentration in the medium surrounding the TET-FG at or above the minimum desired TET concentration.

3. TET-FG Matrix Longevity

The longevity of control FG and AB-FG disks was evaluated by visual assessment of the disks. The porous membrane, cut during the making of the disks, remained attached to the FG and helped to position the disks during their integrity evaluation. Top views of disks containing no TET (controls), and 50 or 100 mg of TET per ml of FG are shown in FIG. 26 at days 0, 9 and 15. This figure shows typical results, namely, the FG control disks were degraded within two weeks whereas the TET-FG disks remained intact, or nearly so, for 15 days. In additional experiments TET-FG disks remained intact or nearly so for at least five weeks (date not shown). No significant change in the FG longevity was observed between sterile and non-sterile TET release experiments.

B. CIP, AMO and MET Data

1. CIP, AMO and MET Release Data

The antibiotic released from CIP-, AMO- and MET-FG is shown in FIG. 28. CIP was released at an apparent constant rate for approximately 4 weeks and then the rate decreased gradually for approximately one more week. The release of AMO and MET was complete within 3 days.

2. CIP and MET Antibacterial Activity

The antimicrobial activity of released CIP and MET (data not shown) parallels the profiles determined spectrophotometrically for identical AB-FG disks.

3. Supplemented—FG Matrix Longevity

The results for CIP-FG were similar to those for TET-FG. The results for AMO- and MET-FG were similar to those obtained for the FG control. No significant change in the FG longevity was observed between sterile and non-sterile experiments.

Discussion

The results demonstrated that poorly water soluble forms of CIP and TET provide a combination of factors that increase significantly the maximum AB load, release period and longevity of the FG matrix into which they are mixed. Alternatively, the FG disks can be stabilized by immersing them in solutions of AB such as TET or CIP.

The results also clearly showed that the AB delivered by AB-FG preserved its antimicrobial activity as demonstrated by the inhibition of E. coli growth. These results demonstrated that TET and CIP supplementation of FG and other TS can overcome the degradation of FG as a limiting factor in drug delivery therefrom. That is these ABs stabilized the FG so that their release periods and the released AB concentrations can be controlled using AB concentrations in the FG. Using these procedures TET and CIP can be loaded into FG and their release can be controlled for a period of days or weeks at effective antimicrobial concentrations.

The TET- and CIP-induced FG stabilization can be exploited for controlling the total release time not only for these ABs, but also for other drugs or "supplements" added to FG whose release rate and/or total release duration depends on the integrity of the FG matrix.

These results have clinical applications in periodontal and other conditions where FG can serve as a localized drug delivery system. The TET- or CIP-induced FG stabilization can be exploited for controlling the total release time of TET, CIP and other drugs or supplements which have been added to the TET-FG or CIP-FG matrices.

EXAMPLE 15

Effect of Temperature on the TET Release Rate from TET-Supplemented FG

FG was supplemented with 50 mg/ml of TET free base and was shaped as 6×2.5 mm disks for this study. The protein concentration of FG was adjusted to 60 mg/ml. The disks were placed in 2 ml of PBS, pH 7.3 and were allowed to stand at 4, 23 and 37° C. To wash the disks, the PBS was replaced every 10 minutes, 6 times, with 2 ml of fresh PBS. Thereafter the PBS was replaced every hour for 4 hours. The TET concentrations in the collected samples were determined spectrophotometrically against a standard curve as before.

The results demonstrated that the rate of TET release was proportional to the temperature (FIG. 29).

EXAMPLE 16

Effect of FG Protein Concentration on the TET Release Rate from TET-Supplemented FG FG supplemented with 1 mg/ml of TET HCl solution was prepared and was shaped as 6×2.5 mm disks for this study. The protein concentration of the FG was adjusted to 60, 30 and 15 mg/ml. Each disk was placed in 3 ml of distilled water. The water was replaced with the same volume of water every 10 minutes for a total of one hour. The TET concentration in the collected samples was determined spectrophotometrically against a standard curve as before.

The data (FIG. 30) show that the TET release rate was highest from the FG with the lowest total protein concentration and vice versa. That is, the TET release rate was inversely proportional to the FG protein concentration.

EXAMPLE 17

In Vivo Antimicrobial Activity of AB Released from AB-Supplemented FG

To test the antimicrobial activity of TET and CIP released from TET- and CIP-FG, the capacity of these AB-supplemented FGs to protect mice from induced peritonitis was evaluated. Experimentally, at day 1, each one of 5 animals per group were injected intraperitoneally with 0.5 ml PBS (Group-I), FG (Group-II), TET-FG (Group-III) or CIP-FG (Group IV). FG and AB-FG was administered using a Hamaedics dispenser containing 0.25 ml of TFC at 120 mg/ml and 0.25 ml of human thrombin at 250 U/ml. In the case of TET- and CIP-FG, the thrombin solution contained 50 mg of the respective AB. At day 2, all the animals were injected intraperitoneally with $2\times10^8$ (Experiment 1) or $4\times10^8$ (Experiment 2) colony forming units (cfu) of S. aureus 202A. Results: (Experiment 1, Experiment 2. Animals surviving at 48 hours after infection): Group I, 0 and 1 survivors; Group II, 3 and 1; Group III, 3 and 5; and Group IV, 5 and 4 survivors. Most survivors lived through the duration of the experiment (2 weeks) but some died or were intentionally killed because they were sick.

These data demonstrated that TET-FG and CIP-FG protected mice from death caused by S. aureaus 202A for at least 48 hours after the administration of the AB-supplemented FG.

EXAMPLE 18

Therapeutic Applications of Supplemented Fibrin Sealant Compositions

The development of ultrathin microfiberoptic endoscopes has offered the laryngologist unique access to the limited spaces of the temporal bone and skull base. While diagnostic middle ear endoscopy is well documented (Edelstein, D. R. et al., Am. J. Oto. 15:50–55 (1994); Poe, D. S. et al., Laryngoscope 102:993–996 (1992); Poe, D. S. et al., Am. J. Oto. 13:529–533 (1992); Balkany & Fradis, Am. J. Oto. 12:46–48 (1991)), therapeutic microendoscopy offers the exciting advantages to the patient of minimal invasiveness, reduced patient morbidity and lower hospital cost. Microendoscopes of constantly shrinking diameters yield images of good quality and resolution. Coupled to a laser and fibrin sealant applicator, several new surgical applications in the middle ear and skull base are now feasible. Potential therapeutic applications were derived from the fibrin sealant's mechanical properties in soft tissue repair and use as a sustained delivery vehicle for pharmaceuticals and biologic growth factors. Possibilities include ototopical aminoglycoside therapy, using for example gentamycin for the treatment of Ménière's disease, transeustachian CSF leak prophylaxis and tympanic membrane repair.

Preliminary antibiotic "release profiles" were obtained using pooled fibrin sealant (American Red Cross, Rockville, Md.), and either amoxicillin and metronidazole as "water soluble" agents, or tetracycline and ciprofloxacin in the "low solubility" category. For this procedure, four human head specimens were preserved and underwent latex vascular injection using the fresh tissue cadaver protocol actively in progress in the Naval Medical Center San Diego, San Diego, Calif. (The fresh tissue cadaver protocol is advantageous in preserving the specimens without loss of "fresh tissue" qualities.)

Both fiberoptic and rigid systems were used as provided by Xomed Corporation (Jacksonville, Fla.). The Alphascope 8 model was a flexible microfiberoptic endoscope with an outside diameter of 0.8 mm and a 115 degree flexible tip which provides a field of view of 65° with 1.5–15 mm depth of observation. The fiberoptic cable was composed of 3,000 pixels and provides 10 cm of insertion length. The Alphascope 12A model was a rigid endoscope with an outside diameter of 1.2 mm and an obliquely angled shaft of 25° and tip of 45° which provided a field of view of 65° with 2–20 mm depth of observation. The fiberoptic cable was composed of 6,000 pixels and provided 8 cm of insertion length. A 0.28 mm KTP laser (Laserscope, Palo Alto, Calif.) was used for all laser applications.

Limited-sink conditions were created using 6×3 mm fibrin sealant discs mixed with a set concentration of antibiotic. Concentrations in the eluate were measured on a daily basis (μg/ml) and evaluated over time to develop the "release profile" in vitro.

A duo-flow catheter was designed specifically to facilitate endoscopic application of fibrin sealant, having a 0.75 mm inner cannula with a 1.5 mm outer cannula. The 1.5 mm outer diameter allowed coupling to a microfiberoptic endoscope for access to the middle ear space, eustachian tube and cranial cavity. A "coaxial," recessed tip allowed continuous tissue sealant application under visual guidance without clotting of the delivery ports.

Microendoscopic and Laser Techniques

Initial procedures were performed on human temporal bone specimens to document the feasibility of microendoscopic work within the middle ear and temporal bone. Both transtympanic as well as transeustachian tube routes were used to access the middle ear. All surgery in the posterior cranial fossa was performed through "keyhole" incisions in the posterior fossa dura through a suboccipital approach. Procedures utilized standard otologic equipment.

Coupled with the KTP laser, surgical manipulation was safely achieved around the oval window, to include lysis of adhesions and stapedotomy. Through a "keyhole" retrosigmoid approach, the flexible endoscope was introduced into the posterior cranial fossa with ready identification of the 7–8 nerve complex. When a comfortable level of technical competence was reached, the KTP laser was successfully employed for vestibular nerve section in 6 cadaver specimens without structural damage to neighboring neurovascular structures. Although difficulty was encountered in gauging the depth of vaporization in the first two specimens with damage apparent to the anteriorly located facial nerve, the problem was resolved with refinement of the technique and a change in the laser angle. The duo-flow catheter was attached to the endoscope when using the KTP laser to suction laser plume.

Fibrin Sealant Delivery

Coupled to a microfiberoptic endoscope, the Duo-Flow catheter (Hemaedics Corp., Malibu, Calif.) was used to deliver antimicrobial composition-supplemented fibrin sealant under direct view to the eustachian tube and middle ear space. Several routes of delivery were used including transtympanic, transeustachian tube and transmastoid through the facial recess. Successful "sealing" of the middle ear cavity, eustachian tube and mastoid cavities was achieved with each method of delivery. Fibrin sealant was noted to persist in these "static" specimens for over one week following application.

Tetracycline release profiles from the fibrin sealant disks showed a prolonged decay pattern in excess of three weeks. Concentrations above therapeutic Minimum Inhibitory Concentrations (MICs) remained for up to 42 days. Fibrinogen concentrations ranging from 20–76 mg/ml had little effect on the release profile of ciprofloxacin.

This demonstration of a sustained-release capacity of fibrin sealant demonstrated the great potential of the supplemented fibrin sealant composition as a therapeutic delivery system. On the antimicrobial level, topical application of fibrin sealant allows long-term delivery of antibiotic doses at many times the current minimal inhibitory concentration, often avoiding side effects observed in a systemic therapy. In particular, when coupled with the laser, microendoscopic surgery using a fibrin sealant localized-release "bioreservoir" offers great potential in the treatment of a broad spectrum of otolaryngic disorders ranging from ototopical amino-glycoside treatment of Meniere's disease to laser nerve section and topical antimicrobial therapy of acute and chronic sinusitis and otitis.

EXAMPLE 19

Sustained Release of Antimicrobial Compositions From Fibrin Sealant

Fibrin sealant (FS) disks were made by the enzymatic conversion of fibrinogen to fibrin by thrombin, and subsequently cross-linked by Factor XIII. Briefly, 100 mg of human Topical Fibrinogen Complex (TFC, American Red Cross, Rockville, Md.), containing 76% fibrinogen and Factor XIII, was combined with 10 mg human thrombin (American Red Cross, Rockville, Md.) and 0.9 ml 40 mM calcium chloride solution. The crosslinking fibrin clot was quickly placed into a 20×10×3 mm mold and pressed to form a slab. FS disks were then punched from the slab using a 6 mm biopsy punch. Following the same procedure, antibiotics were mixed with the lyophilized TFC and thrombin prior to hydration to form antibiotic-impregnated FS (AB-FS) disks. Tetracycline free-base, ampicillin free-acid and ciprofloxicin hydrochloride (Sigma Chemical Co., St. Louis, Mo.) were added separately as 345 mg to the TFC and thrombin prior to calcium chloride addition (final fibrin concentration was 76 mg/ml; final antibiotic concentration was 50 mg/disk).

Antibiotic release was measured in vitro under two extreme conditions, "limited sink" and "infinite sink." Under limited sink conditions, FS and AB-FS disks were placed individually into wells of a 24-well tissue culture plate with two ml of phosphate buffered saline (PBS, pH 7.4). Tissue culture plates were left at 37° C. without agitation. The total volume of PBS was exchanged daily and the eluates evaluated for antibiotic content. Under infinite sink conditions, FS and AB-FS disks were placed individually into 50 ml conical centrifuge tubes with 45 ml PBS and agitated by inversion (20 times/min). All tubes were maintained at 37° C. The total volume of PBS was exchanged daily and the eluates evaluated for antibiotic content.

Antibiotic concentrations were calculated from linear standard curves of optical density versus concentration (0–200 ug/ml). Tetracycline samples were evaluated spectrophotometrically at 340 nm. Ampicillin was measured by first reacting 0.1 ml of the eluate sample with 2.9 ml BCA reagent (Pierce Chemical Co., Rockford, Ill.) for 30 min at 37° C. The resulting colored product was measured at 560 nm. Ciprofloxicin samples were evaluated directly at 340 nm.

To evaluate antibiotic release in vivo, tetracycline (TET)-supplemented FS disks were implanted into mice at two different locations. Male BALB/c mice (20–25 g) were anesthetized for the subcutaneous (s.c.) or intraperitoneal (i.p.) implantation of disks. Incision sites were closed with resorbable sutures and stainless steel clips. Disks were removed at 2, 7, 14, 21 or 28 days post implantation and enzymatically digested with 0.1% trypsin/0.4 mM EDTA at 37° C. for 4–7 days. TET concentrations of the lysates were measured as above to determine the mass of TET remaining in disks after in vivo incubation.

To assess the bioavailability of the antibiotic in TET-FS disks, TET-FS disks were placed into test tubes containing a log phase culture of S. aureus ($1\times10^7$ CFU/ml). Cultures with FS disks containing no antibiotics served as controls. All cultures were incubated at 37° C. for 10 hr. Bacterial samples (0.1 ml) were serially diluted and plated onto nutrient agar to determine the viable bacterial count during the incubation with the disks. An unmanipulated culture was also monitored for comparison.

The elution profiles for the three antibiotics evaluated under limited sink conditions are presented in FIG. 31A. After an initial burst of antibiotic release, the freely water soluble ampicillin eluted completely from the supplemented FS matrix within 7 days. This contrasts the elution profile of tetracycline free-base which demonstrated a slowly decreasing, steady release over 42 days. Tetracycline elution at day 42 was a sustained, anti-microbially effective amount, 0.03–0.04 mg/ml. The release kinetics for ciprofloxicin parallelled those of tetracycline; although, data were only collected for 14 days. The elution profile for infinite sink conditions demonstrated an enhanced release of antibiotics during the first 7 days for all three antibiotics compared with limited sink conditions. Otherwise the elution profiles paralleled those observed for the limited sink conditions.

Release of tetracycline in vivo was measured by calculating the antibiotic remaining in AB-FS disks after 2, 7, 14, 21 or 28 days of in vivo implantion. The data are presented in FIG. 31B (combined with in vitro data) and show that the elution profile for TET-FS disks parallels the elution profile of the limited sink model in vitro. After 14 days in vivo, TET-FS disks still contained 50% of the starting concentration with no difference observed between the two sites (~20% i.p. at day 28). These data demonstrate that both the s.c. and the i.p. sites facilitated the long-term delivery of TET from the TET-FS disks, and that the in vitro experiments were highly predictive of the demonstrated in vivo therapeutic effect.

Antibacterial activity was determined by the ability of TET-FS disks to inhibit growth of a S. aureus culture in vitro (FIG. 31C). TET-FS disks significantly inhibited bacterial growth in the 10 hr of study as compared with FS disks alone. Release of tetracycline and ciprofloxicin from FS disks was long term in both in vitro models demonstrating the correlation between the long term delivery of antibiotics and solubility. Antibiotics of relatively lower solubility were consistently released over longer time periods than highly soluble preparations. The delivery kinetics in vivo resemble those of the limited sink model suggesting a limited flow of body fluids at the s.c. and i.p. sites of delivery. Supplemented FS disks were shown to provide long-term delivery of concentrations of antibiotic sufficient to effectively inhibit bacterial growth, demonstrating that FS is an ideal, biocompatible, resorbable delivery system capable of releasing efficacious localized doses of antibiotic over an extended period of time.

EXAMPLE 20

Long Term Site-Directed Delivery of Cytotoxic/Antiproliferative Drugs from FG

The fibrinogen was solubilized with sterile water or, for one group with water saturated with 5-FU at a concentration of 17 mg/ml. Thrombin solutions were made with sterile water, and then were diluted in 40 mM $CaCl_2$ to a concentration of 15 U/ml, or Thrombin was dissolved in 40 mM $CaCl_2$ saturated with 5-FU in a concentration of 17 mg/ml.

Control FG clots did not contain 5-FU and were produced by mixing 200 μl of TFC solution (at 60 mg/ml) with 200 μl of Thrombin solution (at 15 U/ml) and allowing 20 minutes to polymerize. These clots were made in 12 by 75 mm test tubes and then were placed in 10 mls of 0.05 M Histidine, 0.15 M NaCl, pH 7.3 (Buffer).

FG clots containing saturated levels of liquid 5-FU were produced by mixing 200 μl of TFC (60 mg/ml+17 mg/ml 5-FU) with 200 μl Thrombin solution (15 U/ml+17 mg/ml 5-FU) and allowing 20 minutes for the clots to fully polymerize. The addition of saturated levels of 5-FU in both the TFC and Thrombin solutions somewhat altered clot formation producing a clot that was translucent, as compared to the control FG clots which were quite opaque. The clots that were formed were physically the same as those made with FG alone except in color. Clots were formed in 12 by 75 mm test tubes and then placed in 10 ml of buffer.

A second group of FG clots were made that contained an amount of solid anhydrous 5-FU equal to the amount included in clots formed with saturated solutions of 5-FU. These clots were formed by the addition of 7 mg of solid anhydrous 5-FU to 200 μl of TFC (60 mg/ml) and 200 μl of Thrombin (15 U/ml). Seven mg of 5-FU was placed in a 12 by 75 mm test tube. Two hundred μl of TFC was then added followed by 200 μl of Thrombin. The 3 components were then mixed by pipetting back and forth until a homogenous mixture was observed and further mixing was inhibited due to the clotting reaction. Clots were then placed in 10 ml of histidine buffer.

The final group contained 50 mg of solid anhydrous 5-FU per clot. Due to the increased mass of 5-FU (50 mg instead of 7 mg) the previously used method did not work. Instead of producing a homogenous clot, a clot was formed with the majority of the 5-FU having settled to the bottom of the test tube. To avoid this problem the bottom of the test tube was first coated with 100 μl of TFC (60 mg/ml) and 100 μl of Thrombin (15 U/ml). This formed a clot which covered the concave bottom of the test tube. Next, 50 mg of solid anhydrous 5-FU was added to the surface of the 200 μl clot. Following this, 100 μl of TFC was added along with 100 μl of Thrombin. The two solutions were mixed using an automatic pipettor until the protein started to gel. When this occurred, the pipetting was ended and the clot was allowed to polymerize for 20 minutes. The final product was a clot that contained a dense core of approximately 50 mg of 5-FU. As with the other clots, these were then placed in 10 mls of buffer. The final total protein concentration of the FG in all groups was 30 mg/ml.

Each group contained 10 replicates. Each duplicate was incubated at 37° C. in 10 mls of buffer. Buffer was exchanged for 10 mls of fresh solution at 5, 10, 22, 33, 52, 75 and 114 hours. Aliquots of the eluate buffer were then examined in a spectrophotometer at a wavelength setting of 260 nm. Previous experiments had demonstrated that 5-FU absorbed strongly at this wavelength, while eluates from control FG clots did not.

The results are shown in FIG. 32. Control clots containing no 5-FU gave no significant readings. Clots made with 7 mg of 5-FU either in the form of saturated solutions of 5-FU or an equivalent amount of solid anhydrous 5-FU completed their delivery of 5-FU between 5 to 10 hours, while the clots containing 50 mg of solid anhydrous 5-FU continued to deliver 5-FU for at least 75 hours. Peak levels in all cases occurred at the 5 hour time point.

While not wishing to be bound by theory, it is believed that the duration of 5-FU delivery appeared to be a function of the mass of 5-FU loaded into the gel. As a result, the amount of 5-FU deliverable from the clots containing 5-FU in solution was limited by the solubility of the drug. Thus the inclusion of amounts of solid anhydrous form equal to the amount present in the clots formed from liquid saturated with 5-FU resulted in nearly identical delivery kinetics, while the inclusion of greater amounts of 5-FU in the solid form than were possible using the liquid form, resulted in a tripling of the total duration of delivery, and typically a 10-fold increase in the duration of delivery of a given concentration of the drug. It would be expected that the inclusion of still greater amounts of the solid anhydrous 5-FU would also result in even greater delivery times. In other experiments, it has been found that the amount of 5-FU included in the clots can be increased at least 5-fold and probably higher, and that the 5-FU-FG mixture can also be formulated into an injectable form (data not shown). It would further be expected that the use of an analog or other form of 5-FU that was less soluble in the surrounding aqueous medium than the anhydrous form, and/or had a slower dissolution rate, would result in a further increase in delivery times.

The result of this process is a sustainable delivery of the antiproliferative/cytotoxic drug 5-FU from fibrin clots for at least 10 times longer than is possible using the drug in the aqueous form. This technology (i.e., the use of a solid form of the drug, preferably one with a low solubility and/or dissolution rate) should be generally applicable regardless of the matrix in which the drug particles are suspended, or the drug itself.

EXAMPLE 21

Delivery of Taxol from Fibrin Sealant

Based upon the successful controlled delivery of 5-FU from a supplemented fibrin sealant matrix, protocols were developed to consider the delivery of other chemotherapeutic compounds. Recently, paclitaxel or taxol has been recognized as a very promising agent for the treatment of ovarian and breast cancers (Nicoletti et al., *Ann. of Oncology* 2:151 (1993)). One problem with administering taxol, systemically is that it is highly insoluble in aqueous systems. This has necessitated the use of a systemic delivery vehicle consisting of an oil and alcohol mixture (Rose, W., *Anticancer Drugs* 3:311 (1992)). Unfortunately, this systemic delivery vehicle causes severe reactions in many patients, and current therapeutic applications call for pre-medication to minimize them (Weiss, et al., *J. Clin. Oncol.* 8:1263 (1990); Arbuck et al., *Seminars in Oncol.* 20:31(1993). The malignancies for which taxol is currently under clinical use are generally slow-growing, suggesting that an extended exposure to taxol from supplemented fibrin sealant would be desirable. Additionally, since the lesion produced by these diseases is often accessible clinically through percutaneous biopsy or laparoscopic procedures, the prolonged delivery of effective local concentrations of taxol from a fibrin sealant matrix appeared therapeutically feasible.

The kinetics of taxol delivery from fibrin sealant were initially evaluated, by incorporating taxol (0.26 mg), either as an anhydrous solid or dissolved in ethanol, into a 400 µl fibrin sealant composition. The resulting supplemented fibrin matrices were then placed in 2 ml histidine buffer, and incubated at 37° C. The buffer was exchanged after two days, and again ten days later. The relative concentration of taxol in the resulting eluates determined by measuring their ability to inhibit the growth of a human ovarian carcinoma cell (OVCAR) in vitro (MacPhee et al., *In Current Trends in Surgical Tissue Adhesives: Proceedings of the First International Symposium on Surgical Adhesives*, R. Saltz and D. Sierra, eds. Springer-Verlag).

Briefly, 1000 OVCAR cells in 100 µl of growth medium were plated into each well of a 96 well culture plate and incubated for 24 hours. A 100 µl volume of various dilutions of the eluates was then placed into the wells (10 wells per dilution), and the plates incubated at 37° C. After five days, the number of cells in each well was measured using the MTT assay (Rapaport et al., *American Journal of Clinical Pathology* 97:84(1992)). In this assay, the effect of an anti-proliferative agent is seen as a decrease in the number of cells in the final cultures, and consequently, as a decrease in the amount of MTT that is converted into a chromaphore. The resulting chromaphore is detected by spectrophotometry at 570 nm. The results of the experiment and the source of each eluate is provided in FIG. 33. ($p<0.001$ relative to the medium control (Dunns test)).

The controls included an initial (cellular) activity control (IAC) showing the amount of substrate produced by the OVCAR cells at the time of addition of the eluates, and the medium control, showing the maximum amount of substrate produced after 5 days in culture. The eluates from unsupplemented fibrin sealant alone did not affect this growth.

The results obtained using taxol in solution in ethanol showed that the taxol was completely delivered for up to 85 days. When taxol was incorporated into the fibrin sealant in the solid anhydrous form, the OVCAR cells were significantly inhibited for up to 85 days. Subsequent eluates recovered after an additional 10 days in culture (day 12 eluates) also significantly inhibited the growth of OVCAR cells equally well at dilutions from 1:200 to 1:20,000. This indicated that when the fibrin matrix is supplemented with the solid form of taxol, delivery was sustained beyond the initial 2 day period, and that the amount of taxol delivered in the period from day 2 to day 12 exceeded that which was delivered in the first 48 hours.

These experiments showed that long term delivery of taxol from a supplemented fibrin sealant composition can be accomplished by loading a mass of drug that exceeds its solubility in the matrix volume. This was possible both by incorporating the taxol in its solid form, as well as by dissolving it in ethanol prior to incorporation. This is because the molecular weight of ethanol is much lower than that of taxol. As a result, ethanol will rapidly diffuse from the matrix leaving the highly water insoluble taxol behind to precipitate into solid form within the matrix.

EXAMPLE 22

Fibroblast Chemotaxis in Response to Fibroblast Growth Factor—Supplemented FG and Fibronectin Dulbecco's Modified Eagle's Medium (DMEM) was purchased from Sigma Chemical Co., St. Louis, Mo. Antibiotic-Antimycotic solution was purchased from GIBCO (Grand Island, N.Y.). Recombinant fibroblast growth factor-1 (FGF-1) and −4 (FGF-4) were a kind gift of Reginald Kidd, Plasma Derivatives Laboratory, American Red Cross, Rockville, Md., and Genetics Institute (Cambridge, Mass.), respectively. Recombinant fibroblast growth factor-2 (FGF-2, also known as basic FGF or bFGF) was purchased from Upstate Biotechnology, Inc. (Lake Placid, N.Y.) All plastic ware required for sterile propagation of cultures as well as the chemotaxis assays were purchased from Fisher Scientific (Newark, DE). Millicell-PCF (12.0 µm) inserts were purchased from Millipore, Inc. (Bedford, Mass.). Heparin was obtained from the UpJohn Company (Kalamazoo, Mich.).

NIH/3T3 fibroblasts at passage 126 were purchased from the American Type Culture Collection, Rockville, Md. Cultures from passages 129–133 were used in the chemotaxis assays. Cultures were propagated in DMEM supplemented with 10% Calf serum and approximately 1% antibiotic antimycotic solution. Human dermal fibroblasts (HDFs) were purchased from Clonetics, Inc. (San Diego, Calif.) at passage 2. Cultures from passages 3–5 were used in the chemotaxis assays. Cultures were cultivated in DMEM supplemented with 20% FBS (Hyclone Laboratories, Inc., Logan, Utah) and approximately 1% antibiotic antimycotic solution (Gibco, Grand Island, N.Y.).

Cell Chemotaxis Assays

The procedure used to determine cellular chemotaxis was a combination of two known methodologies. A modification of Boyden's chamber was used as follows: Millicell-PCF (Millipore, Inc., Bedford, Mass.) (12.0 µm) 12.0 mm diameter inserts were placed in individual wells of 24 well plates to create the upper and lower chemotaxis chambers. Chemotaxis results were arrived at by performing checkerboard analysis for every combination of cells and growth factors. Concentrations ranging from 0.1, 1, 10, 100 ng/ml with/without added heparin (10 U/ml) were used for FGF-1, FGF-2 (no heparin) and FGF-4 with all the cell types mentioned in the materials section. Briefly, cultures were trypsinized and placed in DMEM+0.1% Bovine Serum Albumin (BSA) (Sigma Chemical Co., St. Louis, Mo.) for approximately one hour at 37° C. in a 5% $CO_2$ humidified chamber. Two to $2.5 \times 10^5$ cells in 50 µl were added per insert to the upper chamber of the setup of the 24 well plates. Treatments were added as mentioned above. The assay was kept at 37° C. in a 5% $CO_2$ humidified chamber for 4 hours. All combinations tested were performed in triplicate. At the end of 4 hours, the plates were removed from the incubator and the filters were stained following the protocol for staining included with the Millicell-PCF inserts. Briefly, the fluid surrounding the inside and outside of the Millicell-PCF inserts was removed. Three percent glutaraldehyde (Sigma Chemical Co., St. Louis, Mo.) was added to the outside and inside of the inserts for approximately 20 minutes. Following removal of the 3.0% glutaraldehyde, 0.5% Triton X-100 (E.M. Science, Cherry Hill, N.J.) was added for 5–7 minutes. On removal of the 0.5% Triton X-100, Fisher's Hematoxylin Solution Gill's Formulation (Fisher Scientific, Newark, DE) No. 1 was added for about 10 minutes. This solution was washed off in running distilled water for about 5 minutes. Using a cotton swab the upper side of the filter was swabbed to remove cells which had not migrated. Filters were mounted lower side facing up on slides in Crystal Mount™ (Biomeda, Inc., Foster City, Calif.) solution and 10 random fields were counted per slide both visually at 400× and at 200× using an Image Analyzing System to automate the enumeration of the cells on the underside of the filters.

Checkerboard Analysis

As required, checkerboard analysis was carried out to determine random migration, and positive and negative chemotaxis. Growth factors were added to the upper and/or lower chambers to observe whether cells migrated towards the GF alone (chemotaxis), whether migration was random irrespective of whether the growth factor was added to the upper or lower well (chemokinesis) or whether cell migration was against the chemotactic gradient (negative chemotaxis).

Cell Migration Assay to FGF Released From FG

Chemotaxis chambers and cells were utilized as described above. Fifty µl of 8 mg/ml Topical Fibrinogen Complex (TFC, American Red Cross, Rockville, Md.) was added to the bottom of 24 well plates. Forty µl of test growth factor +/−heparin at a final concentration of 10 U/ml (FGF-1, FGF-4 with heparin, FGF-2 alone) was added to the TFC and thoroughly mixed. Ten µl of bovine Thrombin (Armour Pharmaceutical Company, Kankakee, IL) was added and mixed thoroughly. The components were allowed to gel at room temperature for approximately 30 minutes. Total volume in the lower and upper chambers was made up to 0.5 ml each with DMEM +0.1% BSA. The concentration of the FGF's added to the TFC was adjusted to produce the desired overall concentration as determined by:

$$\text{Overall } FGF \text{ Concentration} = \frac{\text{mg of } FGF \text{ added to } TFC}{\text{Volume of liquid in upper chamber} + \text{Volume of } FG \text{ \& liquid in lower chamber}}$$

The assay was performed at 37° C. in a 5% $CO_2$ humidified chamber for approximately 24 hours. At the end of 24 hours, the filters were removed, fixed and stained and the number of cells on the underside of the filter was enumerated as described above.

Results

Capacity for Migration of Fibroblasts

The ability of NIH 3T3 fibroblasts to migrate towards various well known chemotactic agents was determined to ensure that the cells used in this assay retained this capacity. Fibronectin was the most effective chemotactic agent tested for both NIH 3T3 and HDFs with maximal responses occurring at 20 µg/ml (FIG. 34, Table 8). Thereafter, fibronectin at 20 µg/ml was used as the positive control for migration.

Chemotaxis of NIH 3T3 Fibroblasts Towards FGF-1

Maximum stimulation of migration of NIH 3T3 fibroblasts by FGF-1 was observed at 10 ng/ml in the presence of 10 U/ml of heparin (FIG. 35). Checkerboard analysis revealed that FGF-1 was chemotactic for NIH 3T3 cells (Table 9).

Chemotaxis of NIH 3T3 Fibroblasts Towards FGF-2

Maximum stimulation of migration of NIH 3T3 fibroblasts by FGF-2 was observed at 1 ng/ml of FGF-2 (FIG. 36). Checkerboard analysis showed that FGF-2 was chemotactic for NIH 3T3 cells (data not shown).

Chemotaxis of NIH 3T3 Fibroblasts Towards FGF-4

Maximum stimulation of migration of NIH 3T3 fibroblasts by FGF-4 was observed at 10 ng/ml (FIG. 37). Checkerboard analysis revealed that FGF-4 was chemotactic for NIH 3T3 cells (data not shown).

Chemotaxis of HDFs Towards FGF-1

Maximum stimulation of migration of HDFs by FGF-1 was observed from 1 to 10 ng/ml (FIG. 38). Checkerboard analysis showed that FGF-1 was chemotactic for HDFs (Table 10).

Chemotaxis of HDFs Towards FGF-2

Maximum stimulation of migration of HDFs by FGF-2 was observed at 10 ng/ml (FIG. 39). Checkerboard analysis revealed that FGF-2 was chemotactic for HDFs (data not shown).

Chemotaxis of HDFs Towards FGF-4

Maximum stimulation of migration of HDFs by FGF-4 was observed at 10 ng/ml (FIG. 40). Checkerboard analysis showed that FGF-4 was chemotactic for HDFs (data not shown).

Human Dermal Fibroblast Migration to FGF-1, -2 and -4 Incorporated in FG

Maximal migratory response to FGF released from FG was elicited at an incorporated and total concentration of FGF-4 in FG of 1 ng/ml (FIG. 41). Similar results were also found when FGF-1 and FGF-2 were incorporated into the FG (data not shown) except that the concentration of FGF-2 that elicited the peak chemotactic response was 0.01 mg/ml.

TABLE 8

| Concentration of Fibronectin In Lower Compartment | Concentration of Fibronectin In Upper Compartment | | | |
|---|---|---|---|---|
| | 0 µg/ml | 10 µg/ml | 20 µg/ml | 50 µg/ml |
| 0 µg/ml | 48.53 +/− 4.695 | 62.3 +/− 3.269 | 69.6 +/− 12.25 | 62.0 +/− 2.616 |
| 10 µg/ml | 68.03 +/− 10.793 | 47.53 +/− 5.605 | 64.86 +/− 7.961 | 74.66 +/− 3.946 |
| 20 µg/ml | 90.53 +/− 5.203 | 88.73 +/− 4.152 | 56.9 +/− 3.289 | 76.23 +/− 1.8190 |
| 50 µg/ml | 72.43 +/− 8.276 | 91.3 +/− 1.003 | 63.26 +/− 3.835 | 57.46 +/− 2.287 |

TABLE 9

| Concentration of FGF-1 In Lower Compartment | Concentration of FGF-1 In Upper Compartment | | | |
|---|---|---|---|---|
| | 0 ng/ml | 1 ng/ml | 5 ng/ml | 10 ng/ml |
| 0 ng/ml | 32.1 +/− 6.328 | 53.93 +/− 4.152 | 27.27 +/− 3.873 | 25.96 +/− 4.151 |
| 1 ng/ml | 59.46 +/− 6.89 | 36.9 +/− 5.728 | 22.1 +/− 9.232 | 35.86 +/− 2.074 |
| 5 ng/ml | 64.867 +/− 1.75 | 41.44 +/− 1.866 | 24.84 +/− 4.337 | 41.6 +/− 6.717 |
| 10 ng/ml | 70.83 +/− 2.752 | 39.73 +/− 2.428 | 39.73 +/− 2.428 | 41.83 +/− 6.879 |

TABLE 10

| Concentration of FGF-1 in Lower Compartment | Concentration of FGF-1 In Upper Compartment | | | |
|---|---|---|---|---|
| | 0 ng/ml | 0.1 ng/ml | 1 ng/ml | 10 ng/ml |
| 0 ng/ml | 1.96 +/− .602 | 48. +/− 1.965 | 1.3 +/− 0.351 | 4.6 +/− 2.424 |
| 0.1 ng/ml | 66.46 +/− 3.304 | 3.5 +/− 1.550 | 22.0 +/− 6.621 | 9.7 +/− 7.758 |
| 1 ng/ml | 90.0 +/− 5.776 | 27.7 +/− 8.10 | 52.6 +/− 2.775 | 9.7 +/− 3.553 |
| 10 ng/ml | 92.4 +/− 29.307 | 55.1 +/− 7.151 | 44.2 +/− 11.844 | 16.2 +/− 4.781 |
| 100 ng/ml | 65.4 +/− 22.055 | 53.7 +/− 7.3118 | 54.9 +/− 18.599 | 49.166 +/− 9.152 |

Discussion

The FGFs produced a profound chemotactic response in HDFs. For every chemotactic assay performed with HDFs, a very good distinction was obtained between the negative control and the concentration of FGF which elicited a maximal migratory response: 18, 12 and 10 fold in response to FGF-1, -2 and -4, respectively.

The stimulation of chemotaxis by growth factors was not as high for NIH 3T3 cells as it was for HDFs, possibly due to the high passage number of the available stock cultures of the NIH 3T3 cells as compared to the HDFs.

FGF-1, FGF-2 and FGF-4 were found to be potent stimulators of fibroblast chemotaxis. Directed migration of fibroblasts by one or a combination of the above growth factors could result in fibroblast presence in the site of injury, thereby leading to fibroplasia and the laying down of collagen and an extracellular matrix. Thus, aside from it's well recognized angiogenic properties, FGF's may have a role in wound healing, acting either alone or in a combination with PDGF, IGF-1, TGF-β and/or other factors.

Previous studies into the use of FGF's to speed wound healing have not yielded significant results (Carter et al., 1988). This may be due to a requirement for the prolonged exposure of cells to the factors in vivo for a maximal response (Presta et al., *Cell Regul.* 2:719–726 (1991) and Rusnati et al., *J. Cell. Physiol.* 154:152–161 (1993)). Unfortunately, it is difficult to deliver growth factors to wounds for such long time periods under conditions that would not interfere with the healing process.

The present invention of incorporating FGFs into FG allows for the prolonged exposure of cells to the FGFs and can be applied to a wound. The resulting fibrin coating mimics the natural response to tissue injury, while delivering the growth factor directly to the wound site. In a previous study by the present inventors, FG which contained FGF-1 was used to line artificial vascular grafts (Example 8, herein). When these grafts were placed into the vessels of rabbits, the FGF-1 was released for a period of up to 28 days. In further studies involving canine grafts, the effect of the incorporation of FGF-1 into the graft walls was the total endothelialization of the artificial grafts within the same period (Greisler et al., *Surgery* 112:244–255 (1992)). Thus, this form of application elicits a profound biological effect in vivo. The fibroblasts are attracted towards FGF released from FG. This property will be useful in treating wounds with GF-supplemented TS.

EXAMPLE 23

Site-Directed Angiogenesis Using TS to Deliver Angiogenic Substances

This embodiment permits the directed generation of new blood vessels in a controlled manner within the body. In this embodiment, the TS contains and delivers angiogenic substances, such as Fibroblast Growth Factor-1 (FGF-1), in an amount such that its concentration which is released from the supplemented TS is effective to induce angiogenesis.

This embodiment is used in a controlled manner to revascularize body areas which have been deprived of an adequate blood supply such as cardiac, brain and muscle tissue, and the retina. This embodiment is used to restore or improve circulation to implanted organs or re-attached limbs. This embodiment can be used to generate a vascular network or "vascular bed" for: the generation of artificial organs or organoids, the delivery and/or localization of and/or nourishment of cells used in gene therapy, or as a target of gene therapy, for the nourishment and/or localization of cells for tissue augmentation. This embodiment also precludes the necessity of implantation of a device or substance which may induce a foreign body or other excessive inflammatory reaction which could compromise the blood vessel formation or the function of the underlying organ(s).

The invention consists of a formulation of fibrinogen, (suitable for the formation of fibrin) with or without fibronectin and/or collagen, into which is placed an appropriate concentration of an angiogenic substance, such as FGF-1. The fibrinogen may also contain stabilizers to protect against the proteolytic activity of Thrombin. In the case of FGF-1, heparin sulfate (1–1000 U/ml) may be used as the stabilizer in the range of concentration of from 1 ng/ml to 1 mg/ml. Alternatively the angiogenic substance is contained, in an appropriate concentration, in the thrombin, calcium, or water components. This formation is then mixed with thrombin and rapidly applied within the body in a line connecting the desired sites, or to a single site. The fibrinogen-thrombin mix then polymerizes to form FG. The FGF-1, or other angiogenic substance, remains trapped in the FG matrix, either as a free form or bound to the stabilizer or another component of the mixture. In one embodiment, the concentration of the FGF-1 in the TS should be from 0.1 ng/ml to 1 mg/ml, more preferably from 1 ng/ml to 100 µg/ml, most preferably from 100 ng/ml to 10 µg/ml. The FGF-1, or other angiogenic substance, will induce blood vessel formation within the body of the deposited FG. The FG will be naturally biodegraded leaving the intact blood vessel(s).

EXAMPLE 24

Site-Directed Cartilage Induction

This embodiment permits the controlled generation of new cartilage as well as the guided regeneration of damaged cartilage within the body. In this embodiment the TS contains and delivers a cartilage promoting factor(s), such as cartilage-inducing factors-A and/or -B (CIF-A and CIF-B, respectively, which are also known as $TGF-B_1$ and $TGF-B_2$, respectively) and/or another, factor(s) such as Osteoid-Inducing Factor (OIF) in an amount such that the concentration of the inducing factor(s) which is released from the supplemented TS is effective to induce cartilage formation. In one embodiment the concentration of the inducing factors should be 0.1 ng/ml to 1 mg/ml, more preferably from 1 ng/ml to 500 ng/ml, most preferably from 100 to 250 ng/ml. This embodiment may also contain drugs, such as antibiotics, and other growth factors, such as EGF, PDGF, and bFGF in the TS. The cartilage inducing substance is contained in an appropriate concentration in the fibrinogen or thrombin or calcium or water component(s) which are used to prepare the TS.

The supplemented TS can either be pre-shaped to the desired final cartilage form prior to implantation or it can be implanted into the body of the recipient in the liquid form as the TS is mixed and polymerizes. The resulting form may then be sculpted as desired to produce the required shape of cartilage needed. The Cartilage Inducing TS (CI-TS) mixture can also be used to precoat a conventional implant, with the result being a conventional implant with a coating of living cartilage.

Using any of the techniques described above, the CI-TS is then implanted into the body of the recipient. This implantation can be heterotopic or orthotopic. After an appropriate interval, the CI-TS is be replaced by living cartilage with the form of the original CI-TS implant.

Such implants can be used to replace damaged or lost cartilage, or to improve the tissue integration and/or function of an artificial implant. Examples of such uses include the replacement or reconstruction of nasal or ear tissue, the generation of a functional joint surface on a bone implant grown in vivo, or the generation of a similar surface on an artificial implant. The repair of cartilage damaged by disease, such as rheumatoid arthritis, can also be accomplished using the CI-TS to produce a new and smooth cartilage surface to the arthus. Implants intended for space filling applications in Plastic/Reconstructive surgery can also be either formed from CI-TS, or coated with CI-TS to enhance tissue integration and reduce foreign body reactions.

Since current technology does not permit the guided regeneration of cartilage, this invention is an advancement because it permits the generation of cartilaginous tissue which is required to fully mimic the body's natural make-up. This results in improved joint repair, artificial joints and other implants, both for orthopedic and other applications.

For example, this embodiment can be used: to produce improved orthopedic implants or improved plastic/reconstructive implants: for joint repair for traumatic, congenital or pathologically damaged or dysfunctional cartilage; to produce coatings of pacemaker implants and wires to increase their tissue integration and to reduce foreign body reactions. Similar coatings could also be applied to any implantable device for the similar purposes.

EXAMPLE 25

Supplemented TS as a Surface Coating for Biomaterials

This embodiment uses supplemented TS as a coating for the surfaces of orthopedic devices and other biomaterials which are to be implanted into an animal's body. Examples of these devices are urinary catheters, intravascular catheters, sutures, vascular prostheses, intraocular lenses, contact lenses, heart valves, shoulder/elbow/hip/knee replacement devices, total artificial hearts, etc. Unfortunately, these biomaterials may become sites for bacterial adhesion and colonization, which eventually may lead to clinical infection that will endanger the life of the animal. To minimize this problem, the biomaterial is coated with a supplemented TS.

In this embodiment the TS can be supplemented with: a growth factor(s); a drug(s), such as an antibiotic; BMP; and/or cultured cells, etc. Examples of antibiotics that may be incorporated into the TS include, but are not limited to: the penicillins; cephalosporins; tetracyclines; chloramphenicols; metronidazoles; and aminoglycosides. Examples of growth factors which may be incorporated into the TS include but are not limited to FGF, PDGF, TGF-β. Examples of BMPs which may be incorporated into the TS include, but are not limited to, BMP 1 through 8. DBM can also be added to the TS. Examples of cultured cells which may be incorporated into the TS include, but are not limited to, endothelial cells, osteoblasts, fibroblasts, etc.

The supplement(s) maybe contained in either the thrombin, fibrinogen, calcium or water component(s). The concentration of the supplement in the TS is adequate such that it will be effective for its intended purpose, e.g., an antibiotic will inhibit the growth of microbes on the biomaterial, a growth factor will induce the growth of the desired cell type(s) in the TS and/or on the surface of the biomaterial.

This invention is an improvement for existing biomaterial products, which include titanium and titanium alloy devices (such as fixation plates, shoulder/elbow/hip/knee replacement devices, osseointegrated dental implants, etc), solid silicone products (such as Silastic nasal implants, liquid and/or gel silicone products (such as breast implants and testicular implants), and natural or synthetic polymers used as conventional materials in healing a wound site, which may have various forms, such as monofilaments, fibrous assemblies (such as cotton, paper, nonwoven fabrics), films, sponges, bags, etc.

FG is produced from 3 components: fibrinogen (for example as TFC); and thrombin, both of which may be in the lyophilized form; as well as calcium. The lyophilized fibrinogen is reconstituted with sterile water, while the thrombin component is reconstituted with calcium chloride solution. A supplement may be added to any of the three components prior to mixing. Appropriate volumes of the fibrinogen and thrombin containing calcium are mixed to produce the FG. The FG is then applied to the biomaterial's surface as a coating thereof as, for example, by spraying, painting, etc. Alternatively, the implant is dipped in the FG while it is still liquid. A supplement may also be added to the FG before or after it has been coated on a biomaterial surface. For instance, a FG-coated implant is soaked in an antibiotic solution for a specified period of time so that the antibiotic will diffuse into the TS. Another example is coating a device with TS after which cultured cells are seeded onto the fibrin coating. Coating the surface of biomaterials, which will be implanted into an animal, with supplemented TS will serve several purposes, including: the inhibition of bacterial adhesion to the biomaterial; the inhibition of growth of bacteria adhered to the biomaterial; local immune stimulation and/or normalization; the promotion of would healing; and the promotion of engraftment of the biomaterial to the surrounding tissue.

EXAMPLE 26

Self-Contained, TS Wound Dressing

This embodiment is a self-contained TS wound dressing, or bandage, which contains both the thrombin and fibrinogen components of the FG. The calcium is contained in either the thrombin and/or the fibrinogen component(s). Either or both of the thrombin or fibrinogen components can be, but does not have to be, supplemented with a growth factor(s), such as a FGF or bFGF, or a drug(s) such as, an analgesic, antibiotic or other drug(s), which can inhibit infection, promote wound healing and/or inhibit scar formation. The supplement(s) is at a concentration in the TS such that it will be effective for its intended purpose, e.g., an antibiotic will inhibit the growth of microbes, an analgesic will relieve pain.

The thrombin and fibrinogen are separated from each other by an impermeable membrane, and the pair are covered with another such membrane. The thrombin and fibrinogen are contained in a quick evaporating gel (e.g., methylcellulose/alcohol/water). The bandage may be coated on the surface that is in contact with the gel in order to insure that the gel pad remains in place during use. (See FIG. 42).

In operation, the membrane separating the two components is removed, allowing the two components to mix. The outer membrane is then removed and the bandage is applied to the wound site. The action of the thrombin and other components of the fibrinogen preparation cause the conversion of the fibrinogen to fibrin, just as they do with any application of FS. This results in a natural inhibition of blood and fluid loss from the wound, and the establishment of a natural barrier to infection.

In a similar embodiment, the thrombin component and the plastic film separating the Thrombin gel and the Fibrinogen gel may be omitted. The calcium that was previously in the Thrombin gel may or may not be included in the Fibrinogen gel as desired. In operation, the outer impervious plastic film is removed and the bandage applied, as previously described, directly to the wound site. The Thrombin and calcium naturally present at the wound site then induce the conversion of fibrinogen to fibrin and inhibit blood and fluid loss from the wound as above. This embodiment has the advantage of being simpler, cheaper, and easier to produce. However, there may be circumstances in which a patient's wounds have insufficient thrombin. In those cases, the previous embodiment of the invention should be used.

This embodiment is an advancement over the current technology as it permits the rapid application of TS to a wound without the time delay associated with solubilization and mixing of the components. It also requires no technical knowledge or skill to operate. These characteristics make it ideal for use in field applications, such as in trauma packs for soldiers, rescue workers, ambulance/paramedic teams, firemen, in first aid kits for the general public, and by emergency room personnel in hospitals. A small version may also be useful for use by the general public.

EXAMPLE 27

Additional Self-Contained, TS Wound Dressings

The TSs maybe formulated as a self-contained wound dressing, or fibrin sealant bandage, which contains the necessary thrombin and fibrinogen components of the FG. The self-contained dressing or bandage is easy-to-use, requiring no advanced technical knowledge or skill to operate.

The Fibrin Sealant Bandage

The present inventors have prepared a fibrin sealant bandage for applying a tissue sealing composition to wounded tissue in a patient, wherein the bandage comprises, in order: (1) an occlusive backing; (2) a pharmacologically-acceptable adhesive layer on the wound-facing surface of the backing; and (3) a layer of dry materials comprising an effective amount, in combination, of (a) dry, virally-inactivated, purified tissue fibrinogen complex, (b) dry, virally-inactivated, purified thrombin, affixed to the wound-facing surface of the adhesive layer or backing, and (c) calcium chloride. A removable, waterproof, soft plastic, protective film was placed over the layer of dry materials and the exposed adhesive surface of the bandage for stable storage purposes. In operation the waterproof, protective film is removed prior to the application of the bandage over the wounded tissue. The bandage was applied with pressure until the TS has formed over the target area.

The fibrin sealant bandage was tested using a conventional, adhesive silicone patch measuring 6 cm×5 cm, having a total area of 30 cm$^2$. The dry components were placed over the adhesive patch to a depth of ½ cm, so that the total volume of fibrin formed by the TS upon hydration equaled 15 cc (30 cm$^2$×½ cm). The materials used were: 360 mg of topical fibrinogen complex (TFC), described previously; approximately 340 U thrombin, also described previously; and 88 mg CaCl$_2$ (40 mM).

The binding capacity of the bandage for the dry material layer was, in part, dependent upon applying the dry materials as a uniformly-ground, fine powder. The calcium chloride was ground to a fine powder and mixed with the finely ground lyophilized TFC and thrombin, and applied as a powder to the adhesive side of the silicone patch and allowed to adhere to form the fibrin sealant patch. In additional versions of the fibrin sealant bandage, the dry materials were mixed and ground together.

Significantly more of the finely ground powder adhered to the silicone patch when pressure was applied. However, the quantity of dry material added to the fibrin sealant bandage was quantifiable. It was found, for example, in one application using the silicone patch backing that an area, 2×1 $cm^2$, when completely covered by the dry fibrin components increased in weight by 30 mg. This measurement was extrapolated to a dry fibrin component mass per area covered on the backing of 15 $mg/cm^2$.

The fibrin sealant patch was applied to a damp cellulose sponge, representative of a tissue wound, so that the fibrin sealant component was adjacent to the surface of the sponge. The sponge had been previously dampened with room-temperature distilled $H_2O$.

Fibrin formation began to develop within 30 seconds of application. Within three minutes of application, a fibrin gel had formed affixing the tissue sealing fibrin clot to the sponge. This first patch hydrated by the endogenously available liquid was labeled FSB#1.

The previous steps were repeated to prepare patches FSB#2 through FSB#5, however, prior to placing the fibrin sealant bandage against the dampened cellulose sponge, 8 ml of warm PBS were applied to the dry fibrin components affixed to the patch. Incubation of applied patches FSB#2 through FSB#5 was at 37° C. rather than

TABLE 11

| Ban- | Time | | | | | | | |
|---|---|---|---|---|---|---|---|---|
| dage | 3' | 5' | 10' | 15' | 20' | 30' | 120' | 180' |
| 2 | clotted | clotted | clotted | clotted | clotted | clotted | clotted | clotted |
| 3 | in sol'n | in sol'n | in sol'n | in sol'n | in sol'n | in sol'n | in sol'n | in sol'n |
| 4 | in sol'n | in sol'n | in sol'n | in sol'n | in sol'n | in sol'n | in sol'n | in sol'n |
| 5 | in sol'n | very weak gel | weak gel | | | weak, watery gel | | |

TABLE 12

| Experiment # | TFC | Thrombin | $CaCl_2$ | Volume Carbonated $H_2O$ | Initial Volume Fibrin Mass | Final Volume Fibrin Mass |
|---|---|---|---|---|---|---|
| 1 | 51.4 mg/ml | 57 U/ml | 7.1 mM | 3 mls. | 7 mls. | 35 mls. |
| 2 | 30 mg/ml | 29 U/ml | 7.1 mM | 8 mls. | 12 mls. | |
| 3 | 60 mg/ml | 66.7 U/ml | 8.3 mM | 5 mls. | 12 mls. | |
| 4 | 60 mg/ml | 58 U/ml | 7.1 mM | 10 mls. | 24 mls. | 120 mls. | room temperature. The results, set forth in Table 11, exemplify the an application of the fibrin sealant bandage embodiment wherein the dry materials are exogenously hydrated prior to application.

Patch FSB#3 was prepared the same as FSB#1, but absent the thrombin component. Patch FSB#4 was prepared the same as FSB#1, but absent the TFC component. Patch FSB#5 was prepared the same as FSB#1, but absent the calcium chloride component. The results of each test were evaluated over time. As shown below in Table 11, a clotted gel formed when the fibrin components were hydrated with PBS, but remained in solution when either the fibrinogen or thrombin components were deleted from fibrin sealant bandage composition. Similarly, although a weak, watery gel was formed after 30 minutes when the calcium component was deleted from the fibrin sealant bandage and from the hydrating fluid, the composition was unable to develop into a tissue sealing fibrin clot.

To more clearly visualize the formation of the fibrin clot and the extend to which it bound to adjacent surfaces, a small amount toluidine blue was ground into the powdered fibrin components as a color indicator.

In practice, with sufficient hydration the silicone patch was easily removed from the fibrin clot after hydration of the dry, fibrin component layer.

The fibrin sealant bandage, formulated on silicone patches as described above, were also found to effectively form fibrin seals when tested on gelatin surfaces and in vivo on rat tissue. Based on the successful formation of the fibrin seal to a variety of materials and textures, including basic in vivo testing on an uninjured rat, animal studies will be conducted as described in the previous Examples evaluating the TS composition to optimize the hemostatic utility of the fibrin sealant bandage, and to establish delivery kinetics of supplementary components to be added, e.g., growth hormones, drugs, antibiotics, antiseptics, etc.

The Self-Foaming Fibrin Sealant

The present inventors have prepared a self-foaming fibrin sealant dressing for applying a tissue sealing composition to wounded tissue in a patient, wherein the dressing is applied as an expandable foam comprising an effective amount, in combination, of (1) virally-inactivated, purified fibrinogen complex, (2) virally-inactivated, purified thrombin, (3) calcium, and (4) a physiologically acceptable hydration agent; wherein said composition does not significantly inhibit full-thickness skin wound healing. In practice, the previously described TS components will be stored in a canister or tank with a pressurized propellant, so that the components are delivered to the wound site as an expandable foam, which will within minute(s) form a fibrin seal.

A bench model test system is prepared from standard Amicon pressure chambers to determine optimal particle size. Particle size has proven to be important. Preliminary experiments have revealed that a reduction in particle size of the TFC, fibrin and calcium components results in a significant reduction in the time required to hydrate the reagents.

Testing is also relevant to determining the feasibility of combining all of the reagents within a single reservoir, or whether it is more advantageous to maintain each component in a separate reservoir until application. Although probably more expensive, the latter canister prototype (having multiple separate reservoirs) may prove advantageous, in terms of stability and long-term storage.

The test system consists of one or two pressure vessels driven by a pressurized reservoir containing the pharmaceutically acceptable hydrating agent (e.g., water or PBS), and pressurized compressed gas cylinders. The reagents are placed into the appropriate chamber(s) and the reservoir charged with hydrating agent saturated with the propellant at the desired pressure. Mixing of water and the reagents in their reservoirs is accomplished by opening connecting valves. The output is directed into either a single line, or in the case in which the components remain separated, into the joining piece of a Hemedics Fibrin Sealant Dispenser.

In the present case, the TFC was rehydrated with 3 cc $dH_2O$, and warmed to 37° C. to the concentrations shown in Table 12. The thrombin was rehydrated with 0.5 cc $CaCl_2$ solution (100 mM) to the concentrations shown in Table 12. The hydrated components were mixed and carbonated water (10 cc) was added to produce the volumes shown in Table 12. The resulting foaming mixture was placed in a vacuum jar to increase the foaming. Vacuum pressure was applied until the foam dried. The result was a permanent, integrated, foamy mass of fibrin, which expanded approximately 5-fold, and which was both self-adherent and adherent to adjacent textured surfaces.

The foam was also quantitatively measured in calibrated plastic beakers. After two minutes, the volume of the foam was measured and the mass was gently probed to determine that it had set. The quantitative measurements of the expansion of the self-foaming fibrin sealant is indicated in Table 12. Once set, the expandable foam was no longer adhesive to new surfaces.

Based on the successful formation of the self-foaming fibrin dressing, animal studies will be conducted as described in the previous Examples evaluating the TS composition to optimize the hemostatic utility of the self-foam fibrin sealant dressing, and to establish delivery kinetics of supplementary components to be added, e.g., growth hormones, drugs, antibiotics, etc.

Other embodiments of the invention will be apparent to those of skill in the art from a consideration of this specification or practice of the invention disclosed herein. Since modifications will be apparent to those of skill in the art, it is intended that this invention be limited only by the scope of the appended claims.

What is claimed is:

1. A method for treating wounded tissue in a patient, comprising applying to the wounded tissue a composition in the form of a dry powder comprising fibrinogen in an amount which forms a fibrin matrix in the presence of thrombin, Factor XIII, $Ca^{++}$, and aqueous solution;
   providing to the composition, thrombin, Factor XIII, $Ca^{++}$ and aqueous solution in amounts which form a fibrin matrix in the presence of fibrinogen;
   wherein said aqueous solution is provided to the dry powder composition at the site of the wounded tissue;
   further wherein said composition is free of collagen;
   further wherein said composition contains no added fibrinolysis inhibitor;
   and further forming a fibrin matrix when said fibrinogen is applied to said wounded tissue in the presence of thrombin, Factor XIII, and $Ca^{++}$, said fibrin matrix covering and adhering to said wounded tissue.

2. The method of claim 1, wherein said composition further comprises at least one component selected from the group consisting of Factor XIII, thrombin or other catalyst of fibrin formation, and $Ca^{++}$.

3. The method of claim 1, wherein said composition further comprises at least two components selected from the group consisting of Factor XIII, thrombin or other catalyst of fibrin formation, and $Ca^{++}$.

4. The method of claim 1, wherein said composition further comprises Factor XIII, thrombin or other catalyst of fibrin formation, and $Ca^{++}$.

5. The method of claim 1, wherein said composition further comprises at least one supplement selected from the group consisting of: analgesics, anesthetics, antimicrobial compounds, antibodies, anticoagulants, anti-inflammatory compounds, antiproliferatives, cytokines, cytotoxins, chemotherapeutic drugs, growth factors, hormones, interferons, lipids or lipid-containing structures, polynucleotides or oligonucleotides, osteoinducers, polymers, polysaccharides, proteoglycans, polypeptides, protease inhibitors, steroids, vasoconstrictors, vasodilators, vitamins, nutritional minerals and stabilizers.

6. The method of claim 5, wherein said supplement is at least one antibody and/or at least one antimicrobial compound.

7. The method of claim 5, wherein said supplement is at least one growth factor.

8. The method of claim 7, wherein said growth factor is selected from the group consisting of: fibroblast growth factors; platelet-derived growth factors; insulin-like growth factors; epidermal growth factors; transforming growth factors; cartilage-inducing factors; osteoid-inducing factors; osteogenin and other bone growth factors; heparin-binding growth factors; cytokines; interferons; and vascular endothelial growth factors.

9. The method of claim 7, wherein the composition further comprises at least one antibody and/or antimicrobial compound.

10. The method of claim 7, wherein the composition further comprises at least one cytotoxin or cell proliferation inhibiting compound.

11. The method of claim 5, wherein said supplement is at least one cytotoxin or cell proliferation inhibiting compound.

12. The method of claim 11, wherein said cytotoxin or cell proliferation inhibiting compound is selected from the group consisting of enzyme inhibitors, proliferation inhibitors, and dichloroethylsulfide derivatives.

13. The method of claim 11, wherein said cytotoxin or cell proliferation inhibiting compound is selected from the group consisting of 5-fluorouracil, azaribine, estrogen, hormone analogs, insulins, hydoxyurea, L-asparaginase, prednisilone, prednisone, steroids, testosterone, vinblastine, vincristine, taxol, taxotere, gentamycin, carboplatin, cyclophosphamide, and venoms.

14. The method of claim 11, wherein said composition further comprises at least one antibody and/or antimicrobial compound.

15. The method of claim 5, wherein said supplement is released from said fibrin matrix upon dissolution of the fibrin clot for a sustained period, wherein said sustained period is greater than the period obtained according to simple diffusion kinetics.

16. The method of claim 15, wherein said supplement interacts with said fibrin matrix so as to increase the longevity and/or stability of said fibrin matrix compared to that of an unsupplemented fibrin matrix.

17. The method of claim 15, wherein said supplement is of sufficiently low solubility to permit localized, sustained-release of said supplement from said fibrin matrix, wherein said sustained period is greater than the period obtained according to simple diffusion kinetics.

18. The method of claim 1, wherein said composition further comprises at least one supplement selected from the group consisting of fibrin, gelatin, silk proteins and derivatives of fibrin, gelatin, and silk proteins.

19. A method for forming a supplemented fibrin matrix, the method comprising applying to wounded tissue a composition in the form of a dry powder comprising fibrinogen in an amount which forms a fibrin matrix in the presence of thrombin, Factor XIII, and $Ca^{++}$, providing to the composition, thrombin, Factor XIII, $Ca^{++}$ and aqueous solution in amounts which form a fibrin matrix in the presence of fibrinogen, wherein said aqueous solution is provided to the dry powder composition at the site of the wounded tissue, wherein said composition is free of collagen;

further wherein said composition contains no added fibrinolysis inhibitor, further wherein the composition further comprises at least one supplement selected from the group consisting of: analgesics, anesthetics, antimicrobial compounds, antibodies, anticoagulants, anti-inflammatory compounds, antiproliferatives, cytokines, cytotoxins, chemotherapeutic drugs, growth factors, hormones, interferons, lipids or lipid-containing structures, polynucleotides or oligonucleotides, osteoinducers, polymers, polysaccharides, proteoglycans, polypeptides, protease inhibitors, steroids, vasoconstrictors, vasodilators, vitamins, nutritional minerals and stabilizers; and further forming a fibrin matrix when said fibrinogen is applied to said wounded tissue in the presence of thrombin, Factor XIII, and $Ca^{++}$, said fibrin matrix covering and adhering to said wounded tissue.

20. The method of claim 5, wherein said supplement is an anesthetic.

21. The method of claim 5, wherein said supplement is an anesthetic and an antimicrobial compound.

22. The method of claim 1, wherein said fibrinogen is recombinantly-produced human fibrinogen.

23. The method of any one of claims 2–4, wherein said thrombin is recombinantly-produced human thrombin.

24. The method of any one of claims 2–4, wherein said Factor XIII is recombinantly-produced human Factor XIII.

25. The method of claim 8, wherein said growth factor is selected from the group consisting of: fibroblast growth factor-1, fibroblast growth factor-2 and fibroblast growth factor-4; platelet-derived growth factor; insulin-like growth factor-1, insulin-like growth factor-2; epidermal growth factor; transforming growth factor-β; transforming growth factor-β; cartilage-inducing factor-A, cartilage-inducing factor-B; osteoid-inducing factor; osteogenin; heparin-binding growth factor-1 and heparin-binding growth factor-2.

26. The method of claim 1, wherein said composition further comprises a physiologically acceptable propellant.

27. The method of claim 26, wherein said propellant is selected from the group consisting of carbon dioxide, nitrogen, chlorofluorocarbons and hydrofluorocarbons.

28. The method of claim 5, 7, 9 or 10, wherein said composition further comprises at least one regulatory compound selected from the group consisting of inhibiting compounds and potentiating compounds, wherein said inhibiting compounds inhibit agents that interfere with the ability of said growth factor to regulate or mediate cell proliferation, cell differentiation, tissue regeneration, cell attraction, wound repair and/or any cell developmental or proliferative process, while said potentiating compounds increase and/or mediate the ability of said growth factor to regulate or mediate cell proliferation, cell differentiation, tissue regeneration, cell attraction, wound repair and/or any cell developmental or proliferative process.

29. The method of claim 28, wherein said regulatory compound increases and/or mediates the ability of said growth factor supplement to regulate or mediate cell proliferation, cell differentiation, tissue regeneration, cell attraction, wound repair and/or any cell developmental or proliferative process while also inhibiting agents that interfere with the ability of said growth factor to regulate or mediate cell proliferation, cell differentiation, tissue regeneration, cell attraction, wound repair and/or any cell developmental or proliferative process.

30. The method of claim 28, wherein said regulatory compound is heparin.

31. The method of claim 1, wherein said composition further comprises at least one pharmaceutically acceptable diluent, filler or excipient.

32. The method of claim 31, wherein said at least one pharmaceutically acceptable diluent, filler or excipient increases the solubility of said fibrin sealant composition.

33. The method of claim 1, wherein the composition further comprises at least one antioxidant.

34. The method of claim 26, wherein said physiologically acceptable propellant has a boiling point below physiological temperature.

35. The method of claim 32, wherein said pharmaceutically acceptable diluent, filler or excipient is sucrose.

36. The method of claim 29, wherein said regulatory compound is heparin.

37. A method for forming a fibrin matrix, said method comprising applying to wounded tissue a composition in the form of a dry powder comprising fibrinogen in an amount which forms a fibrin matrix in the presence of thrombin and $Ca^{++}$ and aqueous solution;

providing to the composition thrombin, $Ca^{++}$ and aqueous solution in amounts which form a fibrin matrix in the presence of fibrinogen;

wherein said composition is free of collagen;

wherein said aqueous solution is provided to the dry powder composition at the site of the wounded tissue;

and further wherein said composition contains no added fibrinolysis inhibitor.

38. A method for forming a supplemented fibrin matrix, said method comprising applying to wounded tissue a composition in the form of a dry powder comprising an effective amount of at least one supplement and fibrinogen in an amount which forms a fibrin matrix in the presence of thrombin, Factor XIII, $Ca^{++}$ and aqueous solution; and providing to the composition thrombin, Factor XIII, $Ca^{++}$ and aqueous solution in amounts which form a fibrin matrix in the presence of fibrinogen;

wherein said aqueous solution is provided to the dry powder composition at the site of the wounded tissue;

wherein said composition is free of collagen;

wherein said composition contains no added fibrinolysis inhibitor;

and wherein said supplement is releasable from said fibrin matrix upon dissolution of the clot into the external environment of use for a sustained period, further wherein the amount of said supplement in said composition is greater than the amount of said supplement which is soluble in the fibrin matrix, and further wherein said sustained period is greater than the period obtained according to simple diffusion kinetics.

39. The method of claim 38, wherein said supplement is selected from the group consisting of: analgesics, an anesthetic, an antibiotic, an antimicrobial compound, an antiangiogenin, an anticoagulant, an antifibrinolytic agent, an antifungal agent, an anti-inflammatory compound, an antiseptic compound, an antiparasitic agent, an antiviral compound, a cardiovascular drug, a cytotoxin or cell proliferation inhibiting compound, a chemotherapeutic drug, a lipid or liposome, an osteogenic compound, a cartilage inducing compound, a protease inhibitor, a steroid, a vasoconstrictor, a vasodilator, a vitamin, a nutritional supplement, and a mineral.

* * * * *